(12) United States Patent
Pomper et al.

(10) Patent No.: US 11,911,488 B2
(45) Date of Patent: Feb. 27, 2024

(54) SCAFFOLDS AND MULTIFUNCTIONAL INTERMEDIATES FOR IMAGING PSMA AND CANCER THERAPY

(71) Applicant: The Johns Hopkins University, Baltimore, MD (US)

(72) Inventors: Martin G. Pomper, Baltimore, MD (US); Ronnie C. Mease, Fairfax, VA (US); Sangeeta Ray, Ellicott City, MD (US); Ying Chen, Lutherville-Timonium, MD (US); Xing Yang, Balitmore, MD (US)

(73) Assignee: THE JOHNS HOPKINS UNIVERSTY, Baltimore, MD (US)

( * ) Notice: Subject to any disclaimer, the term of this patent is extended or adjusted under 35 U.S.C. 154(b) by 30 days.

(21) Appl. No.: 16/984,415

(22) Filed: Aug. 4, 2020

(65) Prior Publication Data

US 2020/0360542 A1    Nov. 19, 2020

Related U.S. Application Data

(63) Continuation of application No. 15/521,149, filed as application No. PCT/US2015/056909 on Oct. 22, 2015, now Pat. No. 10,736,974.

(60) Provisional application No. 62/067,185, filed on Oct. 22, 2014.

(51) Int. Cl.

| | | |
|---|---|---|
| *A61K 51/04* | (2006.01) | |
| *A61K 41/00* | (2020.01) | |
| *A61K 49/00* | (2006.01) | |
| *C07D 213/82* | (2006.01) | |
| *C07D 209/12* | (2006.01) | |
| *C07C 271/22* | (2006.01) | |
| *C07C 275/16* | (2006.01) | |
| *C07C 323/62* | (2006.01) | |

(52) U.S. Cl.
CPC ...... *A61K 51/0402* (2013.01); *A61K 41/0057* (2013.01); *A61K 49/0002* (2013.01); *A61K 49/0021* (2013.01); *A61K 49/0032* (2013.01); *A61K 49/0041* (2013.01); *A61K 49/0052* (2013.01); *A61K 51/0455* (2013.01); *C07C 271/22* (2013.01); *C07C 275/16* (2013.01); *C07C 323/62* (2013.01); *C07D 209/12* (2013.01); *C07D 213/82* (2013.01); *A61K 49/0017* (2013.01); *A61K 49/0019* (2013.01)

(58) Field of Classification Search
CPC ............ A61K 49/0017; A61K 49/0019; A61K 49/0021

See application file for complete search history.

(56) References Cited

U.S. PATENT DOCUMENTS

| | | |
|---|---|---|
| 7,109,299 B1 | 9/2006 | Balu et al. |
| 2004/0054190 A1 | 3/2004 | Pomper et al. |
| 2004/0242631 A1 | 12/2004 | Garlich et al. |
| 2008/0193381 A1 | 8/2008 | Babich et al. |
| 2013/0034494 A1 | 2/2013 | Babich et al. |
| 2017/0333576 A1 | 11/2017 | Pomper et al. |

FOREIGN PATENT DOCUMENTS

| | | |
|---|---|---|
| WO | WO2003060523 A1 | 7/2003 |
| WO | WO2009002529 A2 | 12/2008 |
| WO | WO2009026177 A1 | 2/2009 |
| WO | WO2009152353 A2 | 12/2009 |
| WO | WO2010014933 A2 | 2/2010 |
| WO | WO2010045598 A2 | 4/2010 |
| WO | WO2010108125 A2 | 9/2010 |
| WO | WO2011106639 A1 | 9/2011 |
| WO | WO2013028664 A1 | 2/2013 |
| WO | WO2013082338 A1 | 6/2013 |

OTHER PUBLICATIONS

Afshar-Oromieh et al., "PET imaging with a [68Ga]gallium-labelled PSMA ligand for the diagnosis of prostate cancer: biodistribution in humans and first evaluation of tumour lesions," European Journal of Nuclear Medicine and Molecular Imaging, 2013, 40(4):486-495.

Afshar-Oromieh et al., "PET/MRI with a 68Ga-PSMA ligand for the detection of prostate cancer," European Journal of Nuclear Medicine and Molecular Imaging, 2013, 40(10):1629-1630.

Afshar-Oromieh et al., "Comparison of PET imaging with a (68)Ga-labelled PSMA ligand and (18)F-choline-based PET/CT for the diagnosis of recurrent prostate cancer," European Journal of Nuclear Medicine and Molecular Imaging, 2014, 41(1):11-20.

Afshar-Oromieh et al., "The diagnostic value of PET/CT imaging with the (68)Ga-labelled PSMA ligand HBED-CC in the diagnosis of recurrent prostate cancer," European Journal of Nuclear Medicine and Molecular Imaging, 2015, 42(2):197-209.

Al-Darwich et al., "Enantioselective synthesis of no-carrieradded (S)-4-chloro-2-[18F]fluorophenylalanine and (S)-a-methyl)-4-chloro-2-[18F]fluorophenylalanine," Journal of Fluorine Chemistry, 1996, 80(2):117-124.

Bander et al., "Phase I trial of 177lutetium-labeled J591, a monoclonal antibody to prostate-specific membrane antigen, in patients with androgen-independent prostate cancer," Journal of Clinical Oncology, 2005, 23(21):4591-4601.

Banerjee et al., "Synthesis and evaluation of technetium-99m- and rhenium-labeled inhibitors of the prostate-specific membrane antigen (PSMA)," Journal of Medicinal Chemistry, 2008, 51(15):4504-4517.

Banerjee et al., "Sequential SPECT and optical imaging of experimental models of prostate cancer with a dual modality inhibitor of the prostate-specific membrane antigen," Angewandte Chemie International Edition English, 2011, 50(39):9167-9170.

(Continued)

*Primary Examiner* — James W Rogers
(74) *Attorney, Agent, or Firm* — Casimir Jones, SC; Jeffrey W. Childers

(57) ABSTRACT

Carbamate and beta-amino acid urea-based scaffolds that have high binding affinity to PSMA are disclosed. These scaffolds can be radiolabeled and used for imaging cells and tumors that express PSMA or for cancer radiotherapy. These compounds also can comprise a fluorescent dye and be used for imaging cells and tumors that express PSMA or for photodynamic therapy.

4 Claims, 13 Drawing Sheets

(56) References Cited

OTHER PUBLICATIONS

Banerjee et al., "64Cu-labeled inhibitors of prostate-specific membrane antigen for PET imaging of prostate cancer," Journal of Medicinal Chemistry, 2014, 57(6):2657-2669.

Banerjee et al., "Preclinical Evaluation of 86Y-Labeled Inhibitors of Prostate-Specific Membrane Antigen for Dosimetry Estimates," Journal of Nuclear Medicine, 2015, 56(4):628-634.

Banerjee et al., "Effect of chelators on the pharmacokinetics of (99m)Tc-labeled imaging agents for the prostate-specific membrane antigen (PSMA)," Journal of Medicinal Chemistry, 2013, 56(15):6108-6121.

Barinka et al., "Interactions between Human Glutamate Carboxypeptidase II and Urea-based Inhibitors: Structural Characterization," Journal of Medicinal Chemistry, 2008, 51(24):7737-7743.

Barinka et al., "Identification of the N-glycosylation sites on glutamate carboxypeptidase II necessary for proteolytic activity," Protein Science, 2004, 13(6):1627-1635.

Barrett et al., "First-in-Man Evaluation of 2 High-Affinity PSMA-Avid Small Molecules for Imaging Prostate Cancer," Journal of Nuclear Medicine, 2013, 54(3):380-387.

Byun et al., "Drug Design of Zinc-Enzyme Inhibitors: Functional, Structural, and Disease Applications," John Wiley & Sons: Hoboken, 2009, pp. 881-910.

Chang et al., "Five different anti-prostate-specific membrane antigen (PSMA) antibodies confirm PSMA expression in tumor-associated neovasculature," Cancer Research, 1999, 59(13):3192-3198.

Chang et al., "Comparison of anti-prostate-specific membrane antigen antibodies and other immunomarkers in metastatic prostate carcinoma," Urology, 2001, 57(6):1179-1183.

Cheng et al., "Relationship between the inhibition constant (K1) and the concentration of inhibitor which causes 50 percent inhibition (I50) of an enzymatic reaction," Biochemical Pharmacology, 1973, 22(23):3099-3108.

Chen et al., "Radiohalogenated Prostate-Specific Membrane Antigen (PSMA)-Based Ureas as Imaging Agents for Prostate Cancer," Journal of Medicinal Chemistry, 2008, 51(24):7933-7943.

Chen et al., "A low molecular weight PSMA-based fluorescent imaging agent for cancer," Biochemical and Biophysical Research Communications, 2009, 390(3):624-629.

Chen et al., "Synthesis and biological evaluation of low molecular weight fluorescent imaging agents for the prostate-specific membrane antigen," Bioconjugate Chemistry, 2012, 23(12):2377-2385.

Chen et al., "2-(3-{1-Carboxy-5-[(6-[18F]fluoro-pyridine-3-carbonyl)-amino]-pentyl}-ureido)-pen tanedioic acid, [18F]DCFPyL, a PSMA-based PET imaging agent for prostate cancer," Clinical Cancer Research, 2011, 17(24):7645-7653.

Cho et al., "Biodistribution, tumor detection, and radiation dosimetry of 18F-DCFBC, a low molecular weight inhibitor of PSMA, in patients with metastatic prostate cancer," Journal of Nuclear Medicine, 2012, 53(12):1883-1891.

Dekker et al., "Functional comparison of annexin V analogues labeled indirectly and directly with iodine-124," Nuclear Medicine and Biology, 2005, 32(4):403-413.

Dusich, "Imaging prostate cancer: Design, synthesis and biological evaluation of optical and radioactive prostate-specific membrane antigen (PSMA) inhibitors," Johns Hopkins University, 2008, PHD Thesis.

Eder et al., "68Ga-complex lipophilicity and the targeting property of a urea-based PSMA inhibitor for PET imaging," Bioconjugate Chemistry, 2012, 23(4):688-697.

Foss et al., "Radiolabeled small molecule ligands for prostate-specific membrane antigen: in vivo imaging in experimental models of prostate cancer," Clinical Cancer Research, 2005, 11(11):4022-4028.

Foss et al., "GCPII imaging and cancer," Current Medicinal Chemistry, 2012, 19(9):1346-1359.

Garg et al., "N-succinimidyl 5-(trialkylstannyl)-3-pyridinecarboxylates: a new class of reagents for protein radioiodination," Bioconjugate Chemistry, 1991, 2(1):50-56.

Ghosh et al., "Tumor target prostate specific membrane antigen (PSMA) and its regulation in prostate cancer," Journal of Cellular Biochemistry, 2004, 91(3):528-539.

Glaser et al., "Two-step radiosynthesis of [18F]N-succinimidyl-4-fluorobenzoate ([18F]SFB)," Journal of Labelled Compounds and Radiopharmaceuticals, 2009, 52(8):327-330.

Hillier et al., "Preclinical Evaluation of Novel Glutamate-Urea-Lysine Analogues That Target Prostate-Specific Membrane Antigen as Molecular Imaging Pharmaceuticals for Prostate Cancer," Cancer Research, 2009, 69(17):6932-6940.

Hillier et al., "99mTc-labeled small-molecule inhibitors of prostate-specific membrane antigen for molecular imaging of prostate cancer," Journal of Nuclear Medicine, 2013, 54(8):1369-1376.

Jackson et al., "Design, synthesis, and biological activity of a potent inhibitor of the neuropeptidase N-acetylated alpha-linked acidic dipeptidase," Journal of Medicinal Chemistry, 1996, 39(2):619-622.

Jackson et al., "Design and pharmacological activity of phosphinic acid based NAALADase inhibitors," Journal of Medicinal Chemistry, 2001, 44(24):4170-4175.

Kabalka et al., "A facile no-carrier-added radioiodination procedure suitable for radiolabeling kits," Nuclear Medicine and Biology, 2004, 31(7):935-938.

Kratochwil et al., "[Lu]Lutetium-labelled PSMA ligand-induced remission in a patient with metastatic prostate cancer," European Journal of Nuclear Medicine and Molecular Imaging, 2015, 42(6):987-988.

Kularatne et al., "Design, synthesis, and preclinical evaluation of prostate-specific membrane antigen (PSMA)-targeted-99mTc radioimaging agents," Molecular Pharmaceutics, 2009, 6(3):790-800.

Kurth et al., "Site-specific conjugation of a radioiodinated phenethylamine derivative to a monoclonal antibody results in increased radioactivity localization in tumor," Journal of Medicinal Chemistry, 1993, 36(9):1255-1261.

Kozikowski et al., "Design of remarkably simple, yet potent urea-based inhibitors of glutamate carboxypeptidase II (NAALADase)," Journal of Medicinal Chemistry, 2001, 44(3):298-301.

Kozikowski et al., "Synthesis of urea-based inhibitors as active site probes of glutamate carboxypeptidase II: efficacy as analgesic agents," Journal of Medicinal Chemistry, 2004, 47(7):1729-1738.

Lapi et al., "Assessment of an 18F-labeled phosphoramidate peptidomimetic as a new prostate-specific membrane antigen-targeted imaging agent for prostate cancer," Journal of Nuclear Medicine, 2009, 50(12):2042-2048.

Majer et al., "Synthesis and biological evaluation of thiol-based inhibitors of glutamate carboxypeptidase II: discovery of an orally active GCP II inhibitor," Journal of Medicinal Chemistry, 2003, 46(10):1989-1996.

Makarasen et al., "Synthesis of four lysine-linked cereulide analogues showing ionophoric activity towards potassium cations as lead compounds for emetic toxin detection by immunoassays," Synthesis, 2009, (13):2184-2004.

Maresca et al., "A series of halogenated heterodimeric inhibitors of prostate specific membrane antigen (PSMA) as radiolabeled probes for targeting prostate cancer," Journal of Medicinal Chemistry, 2009, 52(2):347-357.

Mease et al., "Synthesis and in vivo evaluation of N-[N-[(S)-1,3-dicarboxypropyl]carbamoyl]-4-[18F]fluorobenzyl-L-cysteine, [18F]DCFBC: a new imaging probe for prostate cancer," Clinical Cancer Research, 2008, 14(10):3036-3043.

Mease et al., "PET imaging in prostate cancer: focus on prostate-specific membrane antigen," Current Topics in Medicinal Chemistry, 2013, 13(8):951-962.

Mesters et al., "Structure of glutamate carboxypeptidase II, a drug target in neuronal damage and prostate cancer," The EMBO Journal, 2006, 25(6):1375-1384.

Pavlicek et al., "Structural characterization of P1'-diversified inhibitors of glutamate carboxypeptidase II," Bioorganic and Medicinal Chemistry Letters, 2014, 24(10):2340-2345.

(56) References Cited

OTHER PUBLICATIONS

Perner et al., "Prostate-specific membrane antigen expression as a predictor of prostate cancer progression," Human Pathology, 2007, 38(5):696-701.
Pinto et al., "Prostate-specific membrane antigen: a novel folate hydrolase in human prostatic carcinoma cells," Clinical Cancer Research, 1996, 2(9):1445-1451.
Maung et al., "Probing for a hydrophobic a binding register in prostate-specific membrane antigen with phenylalkylphosphonamidates," Bioorganic & Medicinal Chemistry, 2004, 12(18):4969-4979.
Pomper et al., "11C-MCG: Synthesis, uptake selectivity and primate PET of a probe for glutamate carboxypeptidase II (NAALADase)," Molecular Imaging, 2002, 1(2):96-101.
Rajasekaran et al., "Is prostate-specific membrane antigen a multifunctional protein?," American Journal of Physiology-Cell Physiology, 2005, 288(5): C975-C981.
Reske et al., "Comment on Afshar-Oromieh et al.: PET imaging with a [68Ga]gallium-labelled PSMA ligand for the diagnosis of prostate cancer: biodistribution in humans and first evaluation of tumour lesions," European Journal of Nuclear Medicine and Molecular Imaging, 2013, 40(6):969-970.
Rowe et al., "18F-DCFBC PET/CT for PSMA-based detection and characterization of primary prostate cancer," Journal of Nuclear Medicine, 2015, 56(7):1003-1010.
Rowe et al., "Imaging of metastatic clear cell renal cell carcinoma with PSMA-target 18F-DCFPyL PET/CT," Annals of Nuclear Medicine, 2015, 29(10):877-882.
Silver et al., "Prostate-specific membrane antigen expression in normal and malignant human tissues," Clinical Cancer Research, 1997, 3(1):81-85.
Slusher et al., "Immunocytochemical localization of the N-acetyl-aspartyl-glutamate (NAAG) hydrolyzing enzyme N-acetylated alpha-linked acidic dipeptidase (NAALADase)," The Journal of Comparative Neurology, 1992, 315(2):217-229.
Stoermer et al., "Design, synthesis, and pharmacological evaluation of glutamate carboxypeptidase II (GCPII) inhibitors based on thioalkylbenzoic acid scaffolds," Journal of Medicinal Chemistry, 2012, 55(12):5922-5932.
Stoermer et al., "Synthesis and biological evaluation of hydroxamate-Based inhibitors of glutamate carboxypeptidase II," Bioorganic & Medicinal Chemistry Letters, 2003, 13(13):2097-2100.
Szabo et al., "Initial Evaluation of [F]DCFPyL for Prostate-Specific Membrane Antigen (PSMA)-Targeted PET Imaging of Prostate Cancer," Molecular Imaging and Biology, 2015, 17(4):565-574.
Tsukamoto et al., "Progress in the discovery and development of glutamate carboxypeptidase II inhibitors," Drug Discovery Today, 2007, 12(17-18):767-76.
Tang et al., "Facile synthesis of N-succinimidyl-4-['F]fluorobenzoate ([18F]SFB for protein labeling," Journal of Labelled Compounds and Radiopharmaceuticals, 2008, 51(1):68-71.
Talanov et al., "Preparation and in vivo evaluation of a novel stabilized linker for 211At labeling of protein," Nuclear Medicine and Biology, 2006, 33(4):469-480.
Vaidyanathan et al., "Synthesis of N-succinimidyl 4-guanidinomethyl-3-[*I]iodobenzoate: a radio-iodination agent for labeling internalizing proteins and peptides," Nature Protocols, 2007, 2:(2):282-286.
Vallabhajosula et al., "99mTc-labeled small-molecule inhibitors of prostate-specific membrane antigen: pharmacokinetics and biodistribution studies in healthy subjects and patients with metastatic prostate cancer," Journal of Nuclear Medicine, 2014, 55(11):1791-1798.
Vargas et al., "Molecular imaging of prostate cancer: translating molecular biology approaches into the clinical realm," European radiology, 2015, 25(5):1294-1302.
Wang et al., "Bioisosterism of urea-based GCPII inhibitors: Synthesis and structure-activity relationship studies," Bioorganic & Medicinal Chemistry Letters, 2010, 20(1):392-397.
Weineisen et al., "Synthesis and preclinical evaluation of DOTAGA-conjugated PSMA ligands for functional imaging and endoradiotherapy of prostate cancer," EJNMMI Research, 2014, 4(1):63.
Winkler et al., "Stereocontrolled total synthesis of the potent anti-inflammatory and pro-resolving lipid mediator resolvin D3 and its aspirin-triggered 17R-epimer," Organic Letters, 2013, 15(7):1424-1427.
Zalutsky et al., "A method for the radiohalogenation of proteins resulting in decreased thyroid uptake of radioiodine," International Journal of Radiation Applications and Instrumentation Part A Applied Radiation and Isotopes, 1987, 38(12):1051-1055.
Zechmann et al., "Radiation dosimetry and first therapy results with a (124)I/(131)I-labeled small molecule (MIP-1095) targeting PSMA for prostate cancer therapy," European Journal of Nuclear Medicine and Molecular Imaging, 2014, 41(7):1280-1292.
Zhong et al., "NAAG peptidase inhibitor reduces acute neuronal degeneration and astrocyte damage following lateral fluid percussion TBI in rats," Journal of Neurotrauma, 2005, 22(2):266-76.
Zhou et al., "NAAG Peptidase inhibitors and their potential for diagnosis and therapy," Nature Reviews Drug Discovery, 2005, 4(12):1015-1026.
International Search Report and Written Opinion for Application No. PCT/US2015/056914 dated Jun. 21, 2016 (16 pages).

| COMPOUND | $K_i$ (nM) | COMPOUND | $K_i$ (nM) |
| --- | --- | --- | --- |
| 8 (WANG, 2013) | >1,000 | 23 | 0.11 |
| 9 (CHEN, 2008) | 0.25 | 24 | 0.21 |
| 10 (CHEN, 2008) | 0.01 | 26 | 0.04 |
| 11 (WANG, 2013) | >10,000 | 27 | 0.02 |
| 12 | 42 | 31 | 0.9 |
| 13 | 9.2 | 32 | 0.04 |

AMINO-PENTANEIOIC ACID (NPA)

A) CARBAMATES

GENERAL STRUCTURE
R = ANY ALKYL, ARYL GROUP SIDECHAINS

HIGH BINDING AFFINITY STRUCTURES
R = ANY ALKYL, ARYL GROUP SIDECHAINS

VERSATILE INTERMEDIATE FOR FUNCTIONALIZATION

B) BETA-AMINOACID UREAS

GENERAL STRUCTURE
R = ANY ALKYL, ARYL GROUP, HETEROATOM SIDECHAINS

HIGH BINDING AFFINITY STRUCTURES
R = ANY ALKYL, ARYL GROUP,
HETEROATOM SIDECHAINS

VERSATILE INTERMEDIATES FOR FUNCTIONALIZATION

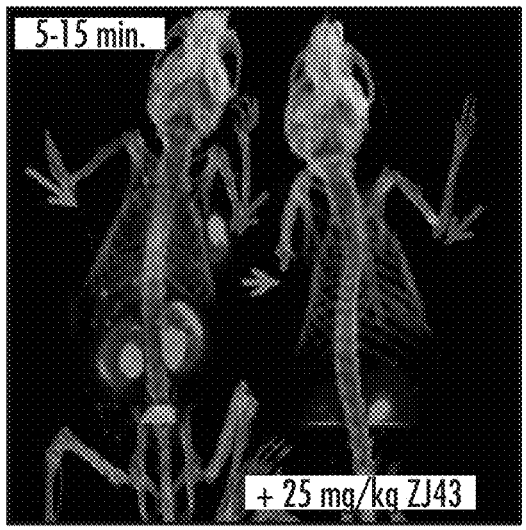 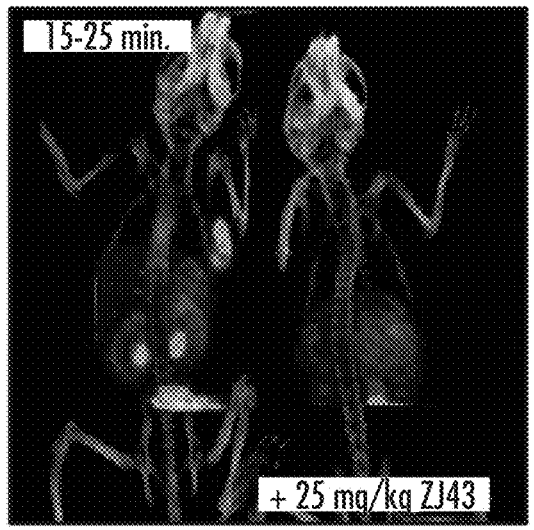 
FIG. 8A    FIG. 8B
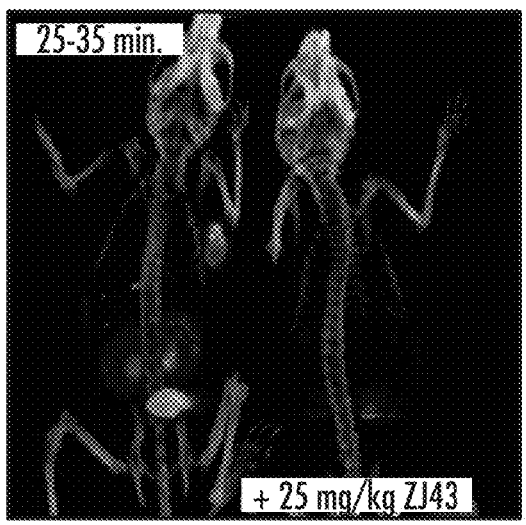 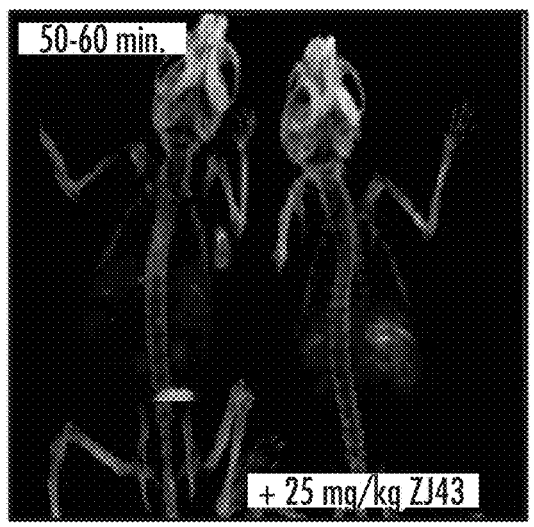
FIG. 8C    FIG. 8D DCMC OR MCG  R = $^{11}CH_3$, n = 1

DCFBC    R = $-CH_2C_6H_5X$, X = $^{18}F$, n = 1

DCIBC    R = $-CH_2C_6H_5X$, X = $^{125}I$, n = 1

SCAFFOLDS AND MULTIFUNCTIONAL INTERMEDIATES FOR IMAGING PSMA AND CANCER THERAPY

CROSS-REFERENCE TO RELATED APPLICATIONS

This application is a continuation of U.S. patent application Ser. No. 15/521,149, filed Apr. 21, 2017, now allowed, which is a § 371 national entry application of PCT/US2015/056909, filed Oct. 22, 2015, which claims the benefit of U.S. Provisional Application No. 62/067,185, filed, Oct. 22, 2014, each of which is incorporated herein by reference in its entirety.

FEDERALLY SPONSORED RESEARCH OR DEVELOPMENT

This invention was made with government support under CA134675 awarded by the National Institutes of Health. The government has certain rights in the invention.

BACKGROUND

Prostate-specific membrane antigen (PSMA) is among the most intensively targeted biomarkers for imaging metastatic prostate cancer. PSMA is a zinc-dependent metallopeptidase that catalyzes the hydrolysis of a series of N-acylpolygammaglutamate derivatives (Mesters, 2006; Barinka, 2004; Pinto, 1996). It is expressed within certain normal tissues, (Ghosh, 2004) but transitions to abundant plasma membrane expression in the epithelium of most prostate cancer and within other solid tumor neovasculature (Rajasekaran, 2005). PSMA membrane expression is associated with metastasis (Chang, 2001), castration resistance (Bander, 2005) and progression of prostate cancer (Perner, 2007).

Several different scaffolds are available for synthesis of small-molecule PSMA inhibitors, and have been reviewed (Byun, 2009; Tsukamoto, 2007; Zhou, 2005). As shown FIG. 1, those potent scaffolds share common features, namely; a) a pentanedioic acid as a glutamate mimic to fit within the S1' binding pocket of the PSMA active site; and b) a zinc-binding group to interact with the catalytic zinc atom at the PSMA active site. A substituent (R) can reside either within the S1 binding pocket or within a void in the protein that extends to the surface. Scaffolds composed of phosphonates or phosphinates, (Jackson, 1996; Jackson, 2000), phosphoramidates (Maung, 2004) and ureas (Kozikowski, 2001; Kozikowski, 2004; Maung, 2004) of general structures 1-3, as well as thiol 4 (Majer, 2003; Stoermer, 2012) and hydroxamate 5 (Stoermer, 2003) have been reported as effective zinc binding groups for PSMA inhibition. However, the presence of a zinc binding moiety and a glutamate mimic residing in the S1' pocket are themselves not sufficient for high binding as demonstrated by gly-urea-glu compound 8 (FIG. 2A and FIG. 2B) (Wang, 2013). Of the reported PSMA binding scaffolds, urea-based inhibitors, first introduced by Kozikowski in 2001 (Kozikowski, 2001) for inhibition of glutamate carboxypeptidase II within the central nervous system, have been utilized the most for targeting PSMA due to their high binding affinity and synthetic simplicity (Kozikowski, 2001; Kozikowski, 2001; Foss, 2012; Mease, 2013; Vargas, 2015; Chen, 200; Barinka, 2008). A variety of low-molecular-weight compounds based on the various scaffolds discussed above, primarily the ureas, have been labeled with radionuclides for positron emission tomography (PET) and single photon emission computed tomography (SPECT), namely, $^{15/124}$I, $^{99m}$Tc, $^{111}$In, $^{18}$F, $^{11}$C, $^{68}$Ga, $^{64}$Cu, and $^{86}$Y, and have demonstrated PSMA-targeted imaging of prostate cancer in experimental models (Foss, 2012; Mease, 2013; Vargas, 2015; Banerjee, 2008; Banerjee, 2015; Banerjee, 2010; Banerjee, 2014; Chen, 2008; Chen, 2011; Eder, 2012; Foss, 2005; Hillier, 2013; Kularatne, 2009; Lapi, 2009; Maresca, 2009; Mease, 2008; Ray Banerjee, 2013; Weineisen, 2014). Several of these have been translated to phase 0-1 clinical trials, where they have enabled visualization of both primary and metastatic bone and soft-tissue lesions due to prostate cancer. (Afshar-Oromieh, 2015; Afshar-Oromieh, 2012; Afshar-Oromieh, 2013; Afshar-Oromieh, 2014; Barrett, 2013; Cho, 2012; Rowe, 2015; Szabo, 2015; Vallabhajosula, 2014). In addition, one agent [$^{18}$F]DCFPyL has also shown a higher sensitivity for detection of metastatic clear cell renal carcinoma compared to conventional imaging methods (S. P. Rowe, 2015).

However, clinical imaging studies also exhibited considerable uptake in non-target PSMA-expressing tissues such as the salivary glands and kidneys, bringing to light potential dose-limiting off-target effects, particularly for radiotherapeutic analogs. Additional PSMA-binding scaffolds that might preserve the positive imaging characteristics of the ureido scaffolds but clear from the non-target organs were sought. The carbamate scaffold was chosen because it would retain the overall geometry of the existing inhibitors, differing only with an O for NH substitution, which eliminates a potential hydrogen bonding donor group present in the ureas. The only PSMA-binding carbamate reported is gly-amino-pentanedioic acid 1 (Wang, 2013) displayed low binding affinity to PSMA, most likely due to the absence of productive binding within the S1 pocket, similar to ureido compound 8. Herein a new class of potent PSMA inhibitors based on the carbamate scaffold to maintain glutamate and S1 pocket side chain geometry and for putative binding to zinc have been reported. Carbamate scaffolds may complement the existing urea and other scaffolds upon which inhibitors, imaging and therapeutic agents targeting PSMA have been based.

Because of the favorable pharmacokinetic profile of this class of compounds, i.e., low nonspecific binding, lack of metabolism in vivo and reasonable tumor residence times, it has been reasoned that urea and carbamate-based agents could also be used for molecular radiotherapy. This will be in analogy with radioimmunotherapy (RIT), which has proved remarkably successful in the treatment of lymphoma with two commercial products routinely integrated into clinical practice. However, (RIT) is fraught with difficulties inherent in the use of radiolabeled antibodies for imaging, including prolonged circulation times, unpredictable biological effects and the occasional need for pre-targeting strategies. Furthermore, antibodies may have less access to tumor than low molecular weight agents, which can be manipulated pharmacologically. Therefore a need remains for low molecular weight compounds with high binding affinity to PSMA for the imaging and radiotherapy of tumors.

Further, for the aforementioned reasons, fluorescent-linker-carbamate based PSMA inhibitors have also been investigated. Targeted fluorescent PSMA binding compounds may find utility in fluorescence guided surgery and biopsy of PSMA positive tumors and tissues, the former providing visual confirmation of complete removal of PSMA containing tissue. Moreover, carbamate conjugates of photosensitizing dyes also provide PSMA targeted photodynamic therapy agents.

SUMMARY

In some aspects, the presently disclosed subject matter provides a compound of formula (I) or formula (II):

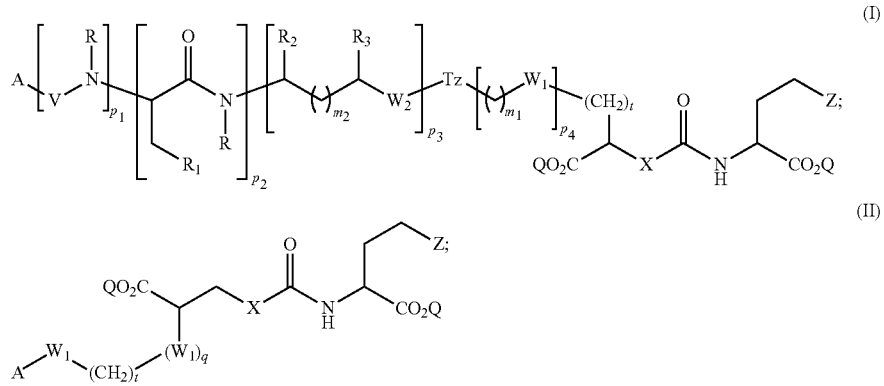

wherein the subunits associate with elements $p_1$, $p_2$, $p_3$ and $p_4$ may be in any order; Z is tetrazole or $CO_2Q$; Q is H or a protecting group; X is O or NH; q is an integer selected from the group consisting of 0 and 1; t is an integer selected from the group consisting of 1, 2, 3, and 4; $p_2$ is an integer selected from the group consisting of 0, 1, 2, and 3, and when $p_2$ is 2 or 3, each $R_1$ is the same or different; $p_1$, $p_3$, and $p_4$ are each independently 0 or 1; $m_1$ and $m_2$ are each an integer independently selected from the group consisting of 0, 1, 2, 3, 4, 5, and 6; $W_1$ is selected from the group consisting of a bond, —S—, —C(=O)—NR—, and —NR—C(=O)—; $W_2$ is selected from the group consisting of a bond, —S—, —CH$_2$—C(=O)—NR—, —C(O)—, —NRC(O)—, —NR'C(O)NR—, —NRC(S)NR'$_2$—, —NRC(O)O—, —OC(O)NR—, —OC(O)—, —C(O)NR—, —NR—C(O)—, —C(O)O—, —(O—CH$_2$—CH$_2$)$_q$— and —(CH$_2$—CH$_2$—O)$_q$—, wherein q is selected from the group consisting of 1, 2, 3, 4, 5, 6, 7, and 8; each R is independently H, $C_1$-$C_6$ alkyl, $C_2$-$C_{12}$ aryl or $C_4$-$C_{16}$ alkylaryl; Tz is a triazole group that can be present or absent and is selected from the group consisting of

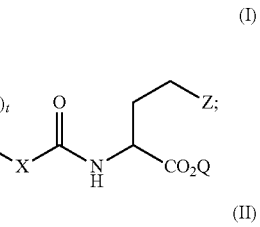

each $R_1$ is independently H, $C_1$-$C_6$ alkyl, $C_2$-$C_{12}$ aryl or $C_4$-$C_{16}$ alkylaryl; $R_2$ and $R_3$ are each independently H and $CO_2R_4$, wherein $R_4$ is selected from the group consisting of H, $C_1$-$C_6$ alkyl, $C_2$-$C_{12}$ aryl, and $C_4$-$C_{16}$ alkylaryl, wherein when one of $R_2$ or $R_3$ is $CO_2R_4$, then the other is H; V is selected from the group consisting of —C(O)—, —C(S)—, —NRC(O)—, —NRC(S)—, and —OC(O)—; A is selected from the group consisting of naphthyl, biphenyl, substituted or unsubstituted aryl, substituted or unsubstituted heteroaryl, each of which can optionally comprise one or more radioactive isotope suitable for imaging and/or radiotherapy, or a photosensitizing dye suitable for imaging and/or photodynamic therapy; and stereoisomers and pharmaceutically acceptable salts thereof.

In certain aspects, the compound of formula (I) or formula (II) further comprises a radioactive isotope suitable for imaging and/or radiotherapy, or a photosensitizing dye suitable for imaging and/or photodynamic therapy.

In other aspects, the presently disclosed subject matter provides a method for imaging one or more prostate-specific membrane antigen (PSMA)-expressing tumors or cells, the method comprising contacting the one or more tumors or cells with an effective amount of a compound of formula (I) and/or formula (II), including compounds of formula (Ia), (Ib), (Ic), and (IIa), and making an image, wherein the compound of formula (I) further comprises a radioactive isotope or a photosensitizing dye suitable for imaging.

In yet other aspects, the presently disclosed subject matter provides a method for treating or preventing a disease or condition associate with one or more PSMA expressing tumors or cells, the method comprising administering at least one compound of formula (I) and/or formula (II), including compounds of formula (Ia), (Ib), (Ic), and (IIa), to a subject in an amount effective to treat or prevent the disease or condition wherein the compound of formula (I) and/or formula (II) further comprises a radioactive isotope suitable for radiotherapy or a photosensitizing dye suitable for photodynamic therapy.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
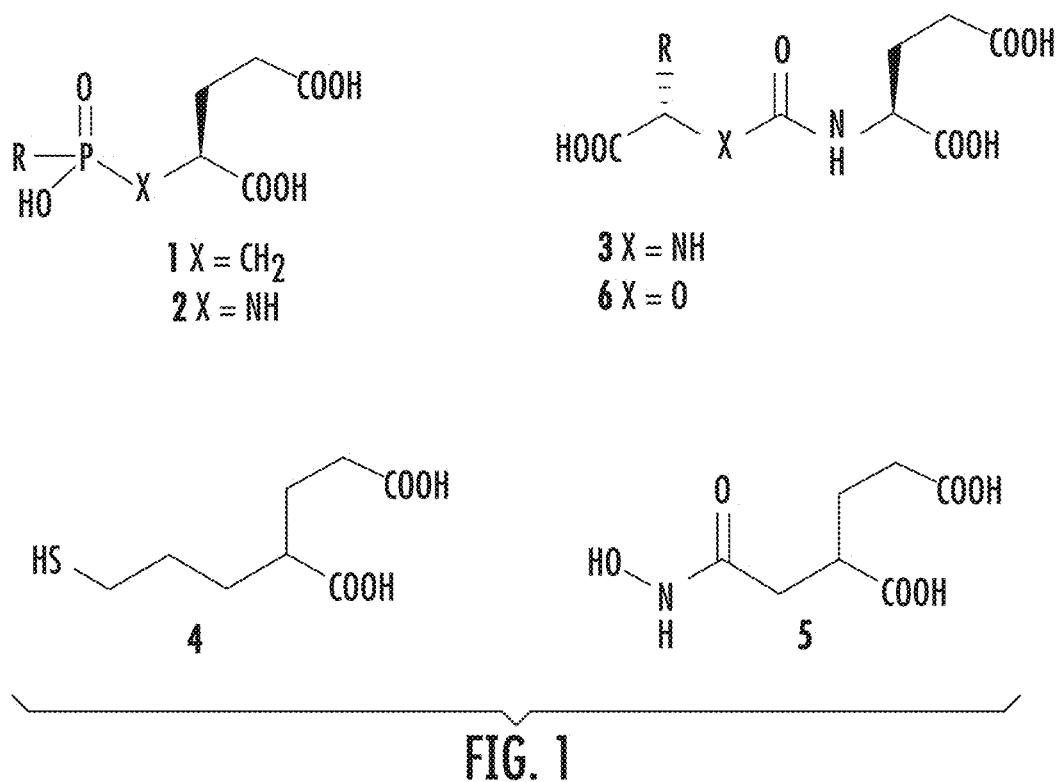
Figures 2A, 2B:
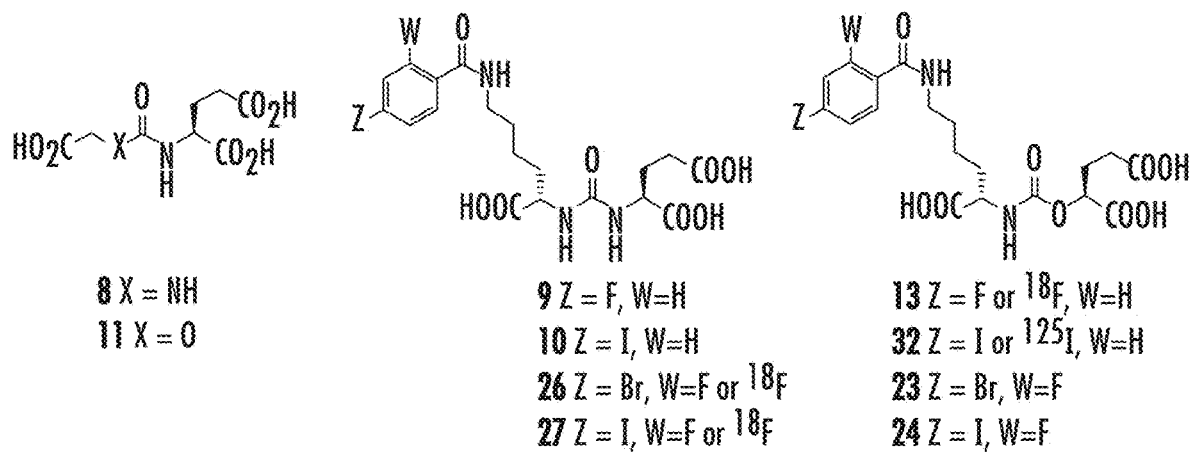
Figure 3A:
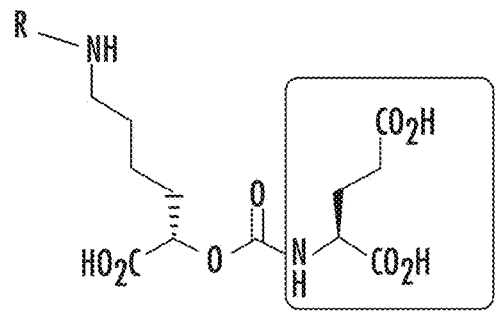
Figure 3B:
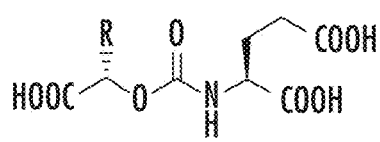
Figure 3B:
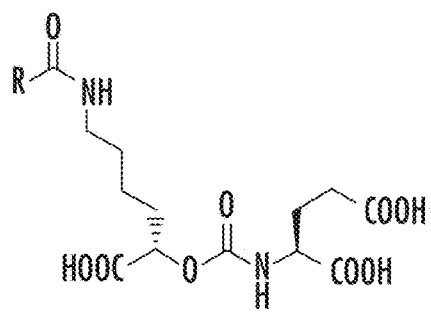
Figure 3B:
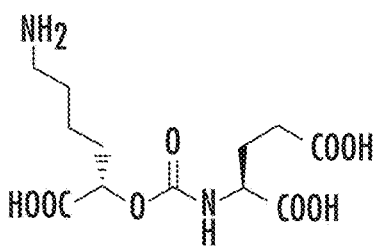
Figure 4:
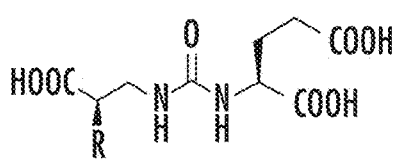
Figure 4:
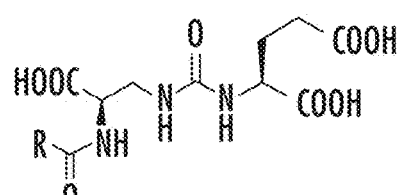
Figure 4:
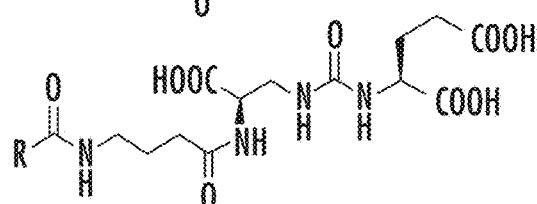
Figure 4:
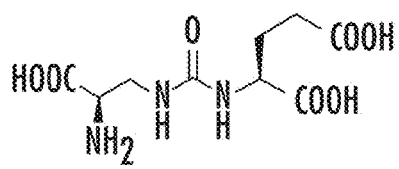
Figure 4:
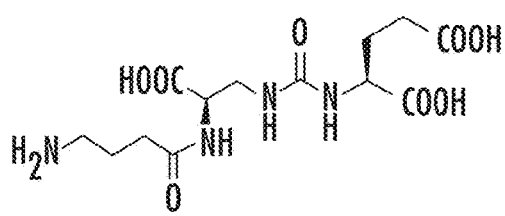
Figure 5:
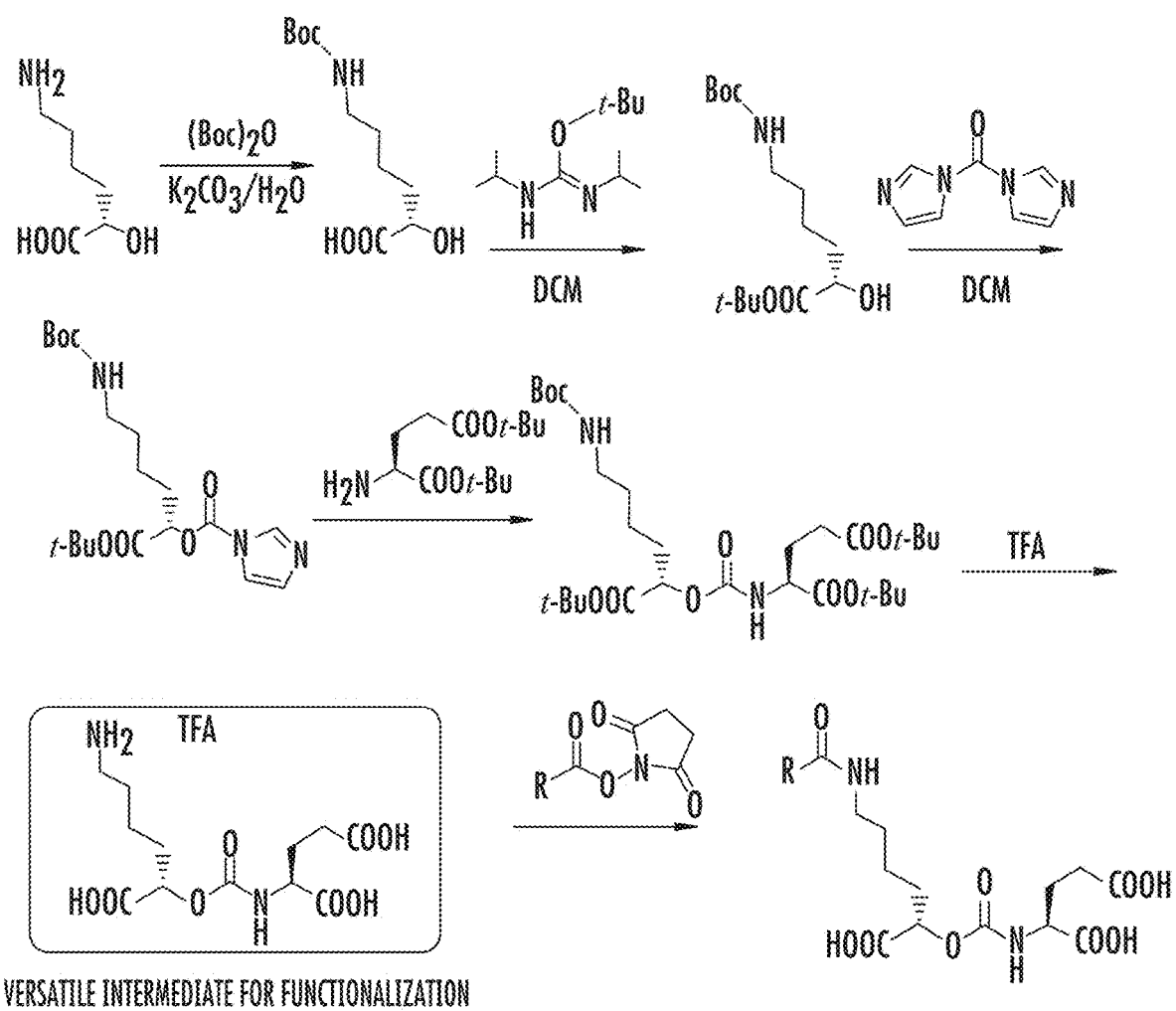
Figure 6:
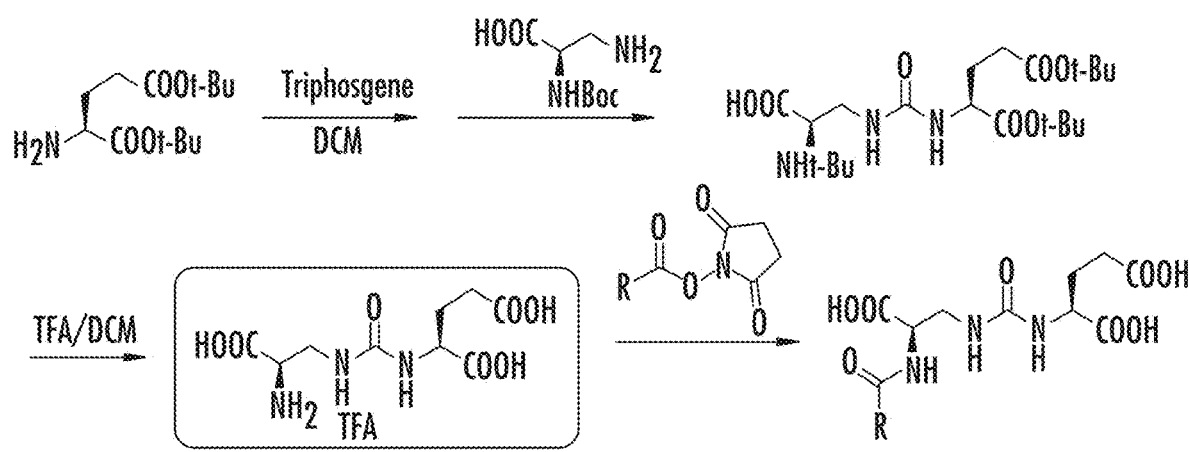
Figure 9:
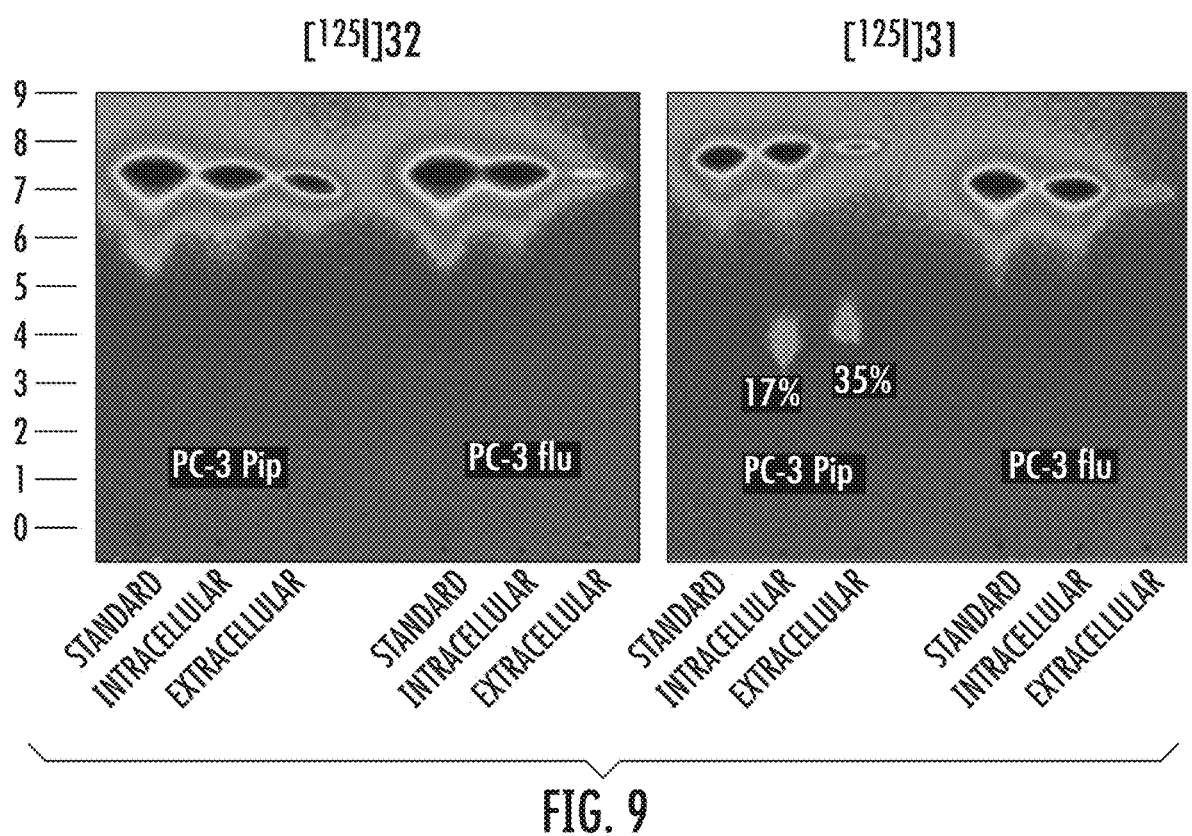
Figure 10:
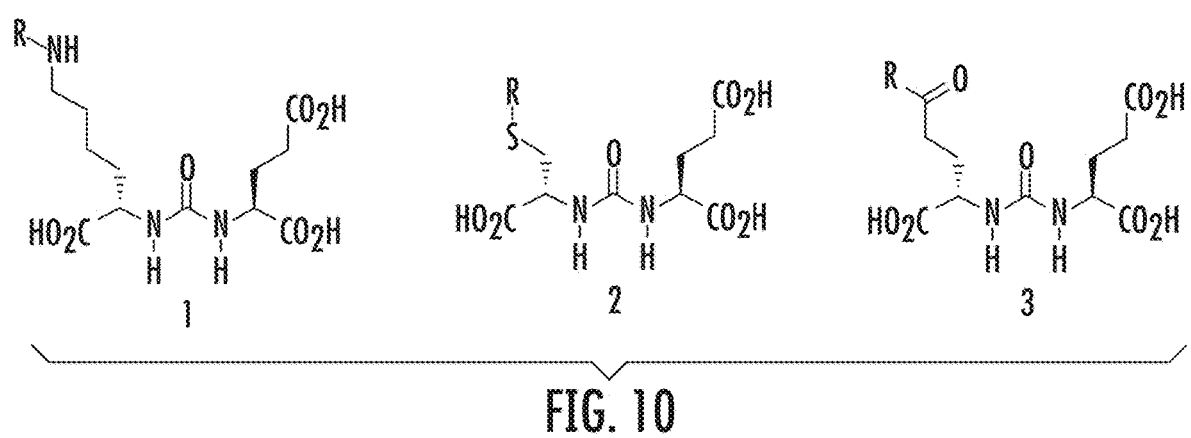
Figure 11:
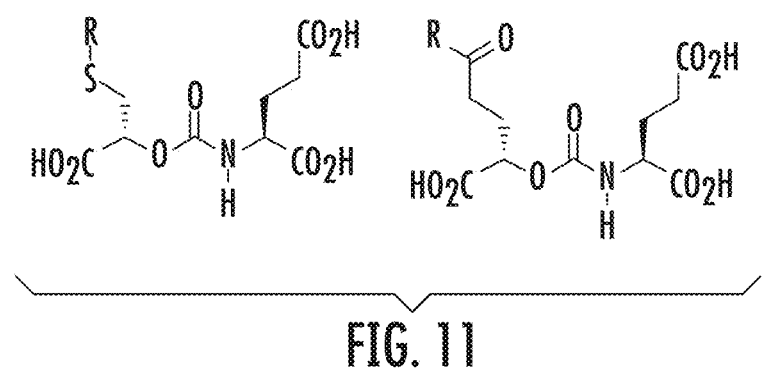
Figure 12:
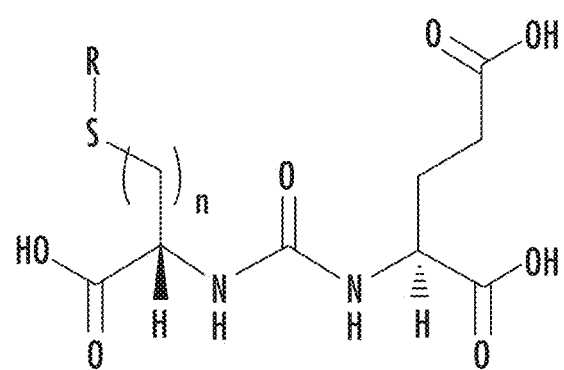
Figure 13:
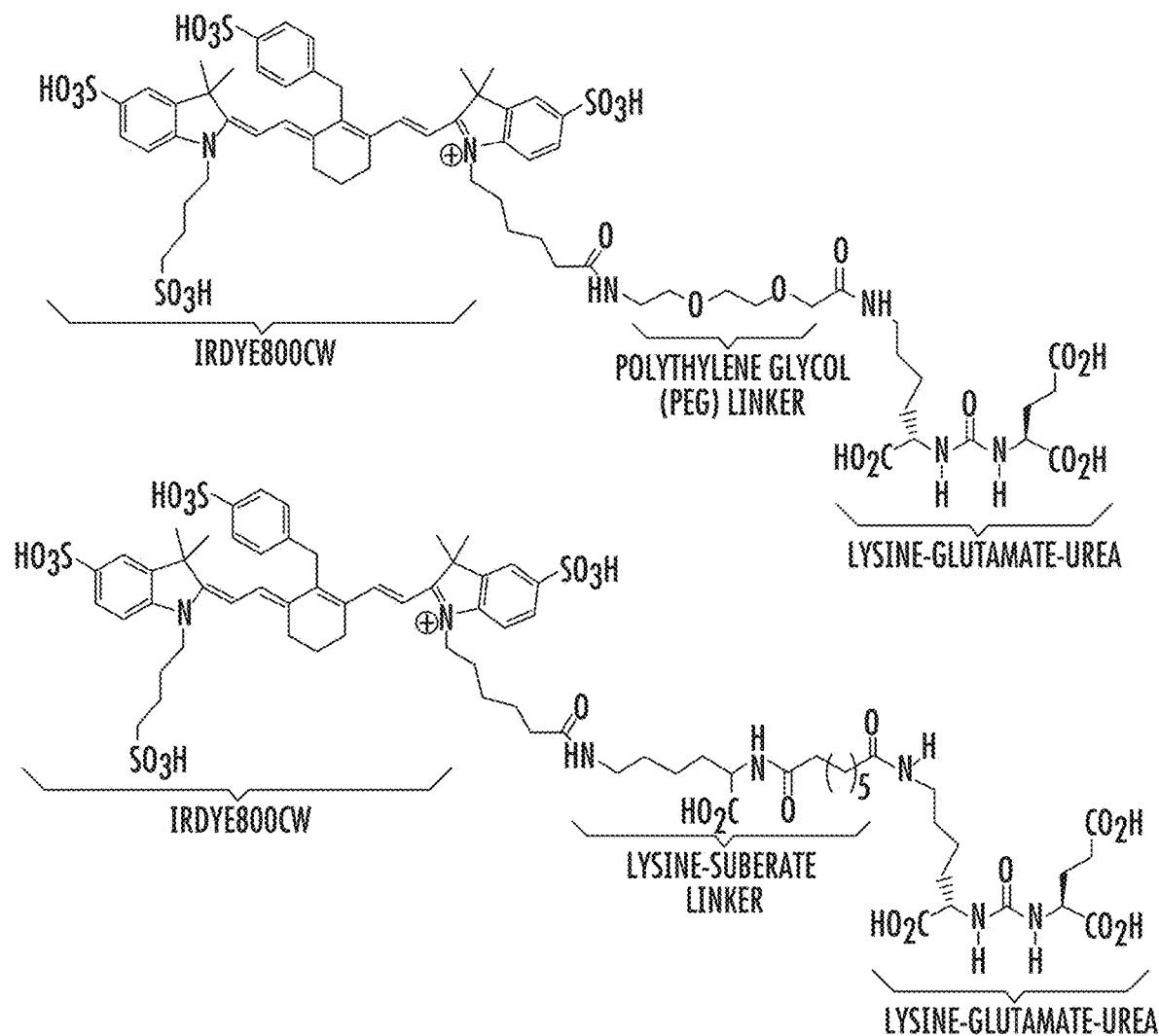

Having thus described the presently disclosed subject matter in general terms, reference will now be made to the accompanying Figures, which are not necessarily drawn to scale, and wherein:

FIG. 1 shows scaffolds available for synthesis of small-molecule PSMA inhibitors; those potent scaffolds share common features, namely; a) a pentanedioic acid (green) as a glutamate mimic to fit within the S1' binding pocket of the active site; and b) a zinc-binding group (blue) to interact with the catalytic zinc atom at the PSMA active site (blue); a substituent (R) can reside either within the S1 binding pocket or within a void in the protein that extends to the surface;

FIG. 2A and FIG. 2B show (FIG. 2A) urea, a carbamate, and reversed carbamate-based PSMA binding compounds; (FIG. 2B) binding affinities of urea, carbamate and reversed carbamate-based PSMA compounds;

FIG. 3A and FIG. 3B show (FIG. 3A) the lysine-carbamate scaffold used to design compounds of the presently disclosed subject matter: amino-pentanedioic acid (NPA) corresponding to a carbamate scaffold; (FIG. 3B) the general structure, high binding affinity compounds, and versatile intermediates of the presently disclosed carbamates;

FIG. 4 shows the general structure, high binding affinity compounds, and versatile intermediates of the presently disclosed beta-amino acid ureas;

FIG. 5 is a synthesis scheme for the presently disclosed carbamates;

FIG. 6 is a synthesis scheme for the presently disclosed beta-amino acid ureas;

FIG. 7A, FIG. 7B, FIG. 7C, and FIG. 7D show docking of 9 (YC-I-26), 12 (XY-20), and 13 (XY-48) to PSMA; (FIG. 7A) urea 9 (YC-I-26); (FIG. 7B) Lys-NPA Carbamate 12 (XY-20); (FIG. 7C) Lys-OPA Carbamate 13 (XY-48); (FIG. 7D) overlay of 9 (YC-I-26) (red), 12 (XY-20) (blue) and 13 (XY-48) (green);

FIG. 8A, FIG. 8B, FIG. 8C, and FIG. 8D show positron emission tomography-computed tomography (PET-CT) images in male NOD-SCID mice injected with the radiolabeled [$^{18}$F]XY-20 compound at (FIG. 8A) 5-15 minutes, (FIG. 8B) 15-25 minutes, (FIG. 8C) 25-35 minutes and (FIG. 8D) 50-60 minutes after injection; the mice on the right in each panel were pretreated with ZJ43 and the mice on the left in each panel were not pretreated with ZJ43. The green arrows point to the PSMA-negative PC3-flu tumor and the red arrows point to the PSMA-expressing (PC3-PIP) tumor (target); 200 microCi of radiotracer was injected;

FIG. 9 shows TLC analysis of Metabolism of [$^{125}$I]31 ([$^{125}$I]XY-26) and [$^{125}$I]32 ([$^{125}$I]XY-57) in PC 3 PIP (PSMA+) and PC3 flu (PSMA−) cells;

FIG. 10 shows three PSMA binding scaffolds: the lysine-glutamate urea 1, cysteine-glutamate urea 2, and glutamate-glutamate urea 3;

FIG. 11 shows a cysteine-NPA carbamate and a glutamate-NPA carbamate scaffolds used to design compounds of the presently disclosed subject matter;

FIG. 12 shows the cysteine-glutamate urea scaffold used for PSMA binding and imaging for over 10 years starting with C-11 labeled DCMC, F-18 labeled DCFBC both for PET imaging with the latter currently in use in patients, and I-125 labeled DCIBC for SPECT imaging and or radiotherapy;

FIG. 13 shows two specific examples of RDye800CW-linker-ureas.

DETAILED DESCRIPTION

The presently disclosed subject matter now will be described more fully hereinafter with reference to the accompanying Examples and Figures, in which some, but not all embodiments of the presently disclosed subject matter are illustrated. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples and Figures. Therefore, it is to be understood that the presently disclosed subject matter is not to be limited to the specific embodiments disclosed and that modifications and other embodiments are intended to be included within the scope of the appended claims.

I. New Scaffolds and Multifunctional Intermediates for Imaging PSMA and Cancer Therapy The presently disclosed subject matter provides new carbamate and beta-amino acid urea-based scaffolds that have high binding affinity to PSMA. These scaffolds can be radiolabeled and used to image cells and tumors that express PSMA. Some advantages to the presently disclosed methods include, but are not limited to, lower renal uptake of the presently disclosed compounds compared with existing urea-based PSMA-targeted radiotracers, as well as more rapid renal clearance as compared to compounds known in the art.

In some embodiments, the presently disclosed carbamate and beta-amino acid urea-based scaffolds complement existing urea and other scaffolds upon which inhibitors, imaging, and therapeutic agents targeting PSMA have been based. Versatile intermediates for carbamate beta-amino acid scaffolds can be functionalized in one or two steps toward PET imaging agents.

In other embodiments, the presently disclosed carbamate based scaffolds can be conjugated with near infrared dye molecules and their use in imaging PSMA and PSMA targeted photodynamic therapy agents also are provided.

A. Compounds of Formula (I) or Formula (II)

Accordingly, in some embodiments, the presently disclosed subject matter provides a compound of formula (I) or formula (II):

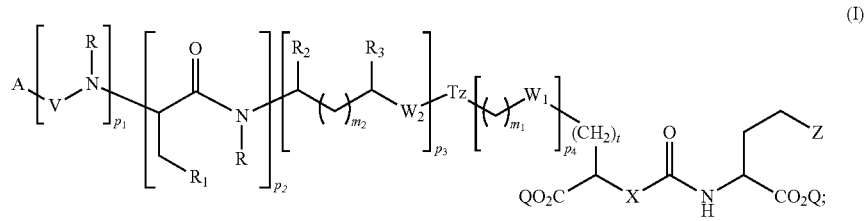

(I)

-continued

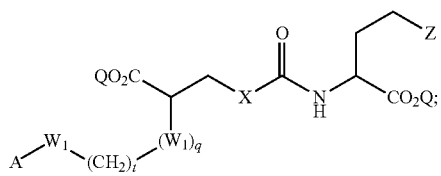

wherein the subunits associate with elements $p_1$, $p_2$, $p_3$ and $p_4$ may be in any order; Z is tetrazole or $CO_2Q$; Q is H or a protecting group; X is O or NH; q is an integer selected from the group consisting of 0 and 1; t is an integer selected from the group consisting of 1, 2, 3, and 4; $p_2$ is an integer selected from the group consisting of 0, 1, 2, and 3, and when $p_2$ is 2 or 3, each $R_1$ is the same or different; $p_1$, $p_3$, and $p_4$ are each independently 0 or 1; $m_1$ and $m_2$ are each an integer independently selected from the group consisting of 0, 1, 2, 3, 4, 5, and 6; $W_1$ is selected from the group consisting of a bond, —S—, —C(=O)—NR—, and —NR—C(=O)—; $W_2$ is selected from the group consisting of a bond, —S—, —CH$_2$—C(=O)—NR—, —C(O)—, —NRC(O)—, —NRC(O)NR—, —NRC(S)NR—, —NRC(O)O—, —OC(O)NR—, —OC(O)—, —C(O)NR—, —NR—C(O)—, —C(O)O—, —(O—CH$_2$—CH$_2$)$_r$— and —(CH$_2$—CH$_2$—O)$_r$—, wherein r is selected from the group consisting of 1, 2, 3, 4, 5, 6, 7, and 8; each R is independently H, $C_1$-$C_6$ alkyl, $C_2$-$C_{12}$ aryl, and $C_4$-$C_{16}$ alkylaryl; Tz is a triazole group that can be present or absent and is selected from the group consisting of

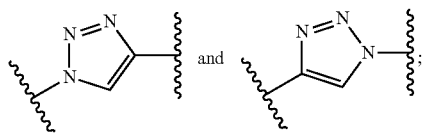 [SMILES: *c1cn(*)nn1 ; *c1cn(*)nn1]

each $R_1$ is independently H, $C_1$-$C_6$ alkyl, $C_2$-$C_{12}$ aryl or $C_4$-$C_{16}$ alkylaryl; $R_2$ and $R_3$ are each independently H and $CO_2R_4$, wherein $R_4$ is selected from the group consisting of H, $C_1$-$C_6$ alkyl, $C_2$-$C_{12}$ aryl, and $C_4$-$C_{16}$ alkylaryl, wherein when one of $R_2$ or $R_3$ is $CO_2R_4$, then the other is H; V is selected from the group consisting of —C(O)—, —C(S)—, —NRC(O)—, —NRC(S)—, and —OC(O)—; A is selected from the group consisting of naphthyl, biphenyl, substituted or unsubstituted aryl, substituted or unsubstituted heteroaryl, each of which can optionally comprise one or more radioactive isotope suitable for imaging and/or radiotherapy, or a photosensitizing dye suitable for imaging and/or photodynamic therapy; and stereoisomers and pharmaceutically acceptable salts thereof.

In particular embodiments, the compound of formula (I) is selected from the group consisting of:

(Ia)

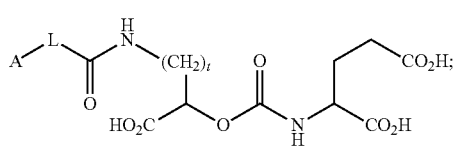

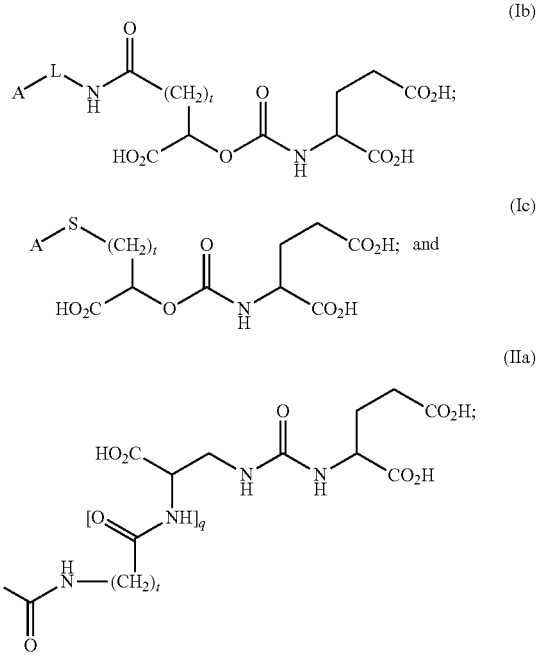

wherein L is a linker that can be present or absent, and has the following general structure:

wherein $p_1$, $p_2$, $p_3$, $m_1$, $m_2$, q, t, Tz, $W_2$, R, $R_1$, $R_2$, $R_3$, V and A are defined as hereinabove.

Suitable linkers are disclosed in U.S. Patent Application Publication No. US2011/0064657 A1, for "Labeled Inhibitors of Prostate Specific Membrane Antigen (PSMA), Biological Evaluation, and Use as Imaging Agents," published Mar. 17, 2011, to Pomper et al., and U.S. Patent Application Publication No. US2012/0009121 A1, for "PSMA-Targeting Compounds and Uses Thereof," published Jan. 12, 2012, to Pomper et al, each of which is incorporated by reference in its entirety.

In yet more particular embodiments, L is selected from the group consisting of:

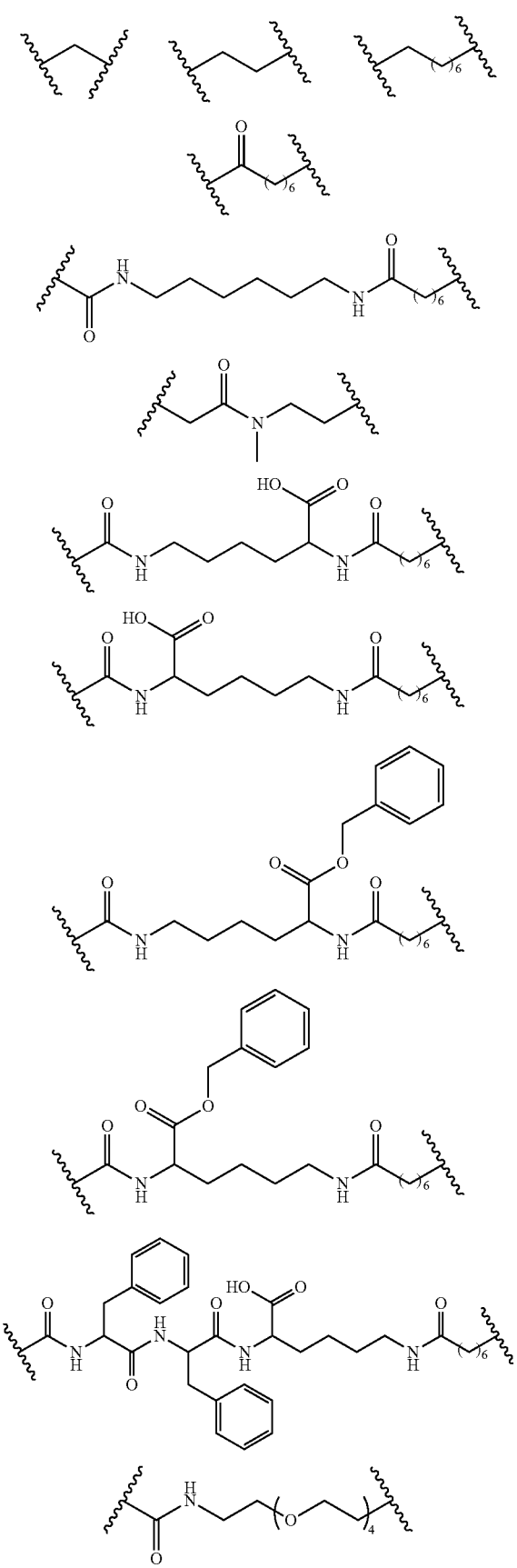

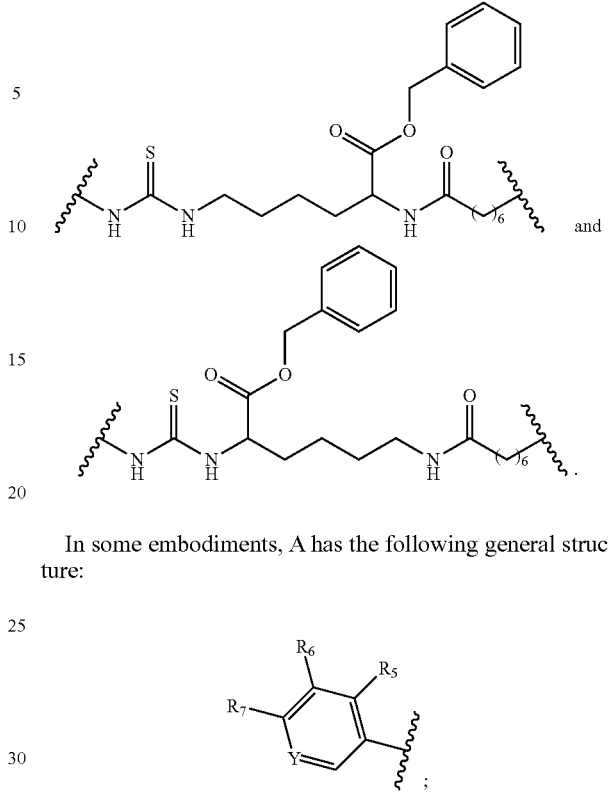

and

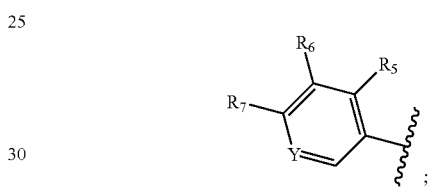

In some embodiments, A has the following general structure:

R_6, R_5, R_7, Y structure wherein: Y is CH or N; and $R_5$, $R_6$, and $R_7$ are each independently selected from the group consisting of H, halogen, alkoxyl, alkythioether, substituted and unsubstituted aryl, $CH_2$—NH—C(=NH)—$NH_2$, —NH—(C=O)—$R_8$, wherein $R_8$ is alkyl, —(C=O)—$NR_9R_{10}$, wherein $R_9$ and $R_{10}$ are each independently selected from the group consisting of H and alkyl, —$X_1$—$(CH_2)_p$-Ph-$X_2$, —$X_1$—$(CH_2)_p$—$X_2$, —$X_1$—$(CH_2)_p$—NH—C(=O)-Ph-$X_2$, wherein each $X_1$ is independently O or S, each p is independently an integer selected from the group consisting of 1, 2, 3, and 4, each Ph is phenyl, and each $X_2$ is halogen.

In particular embodiments, the compound of formula (I) is selected from the group consisting of:

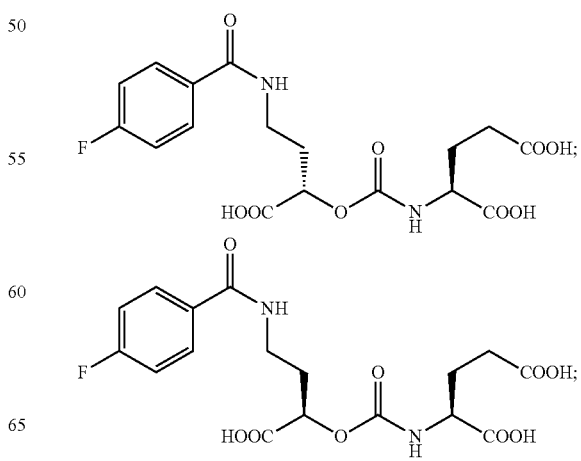

-continued
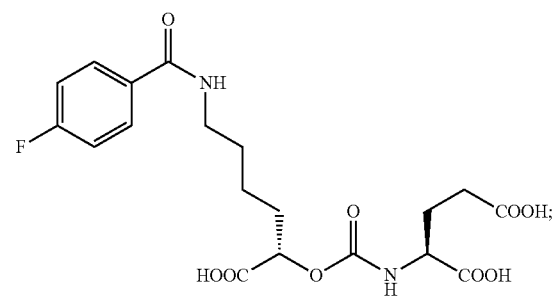
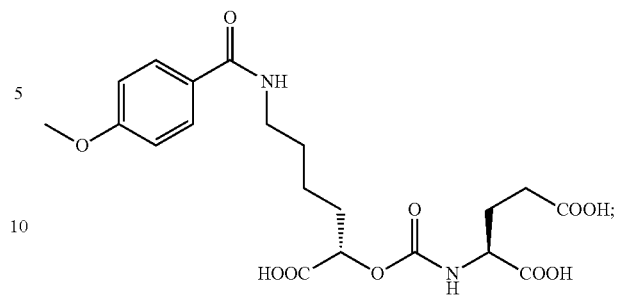
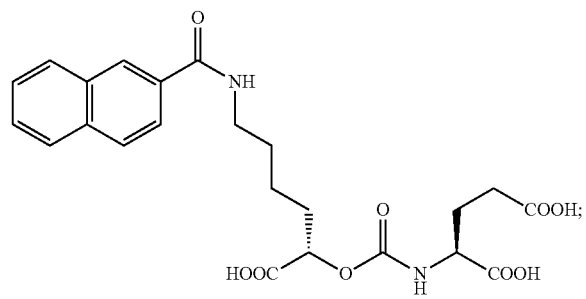
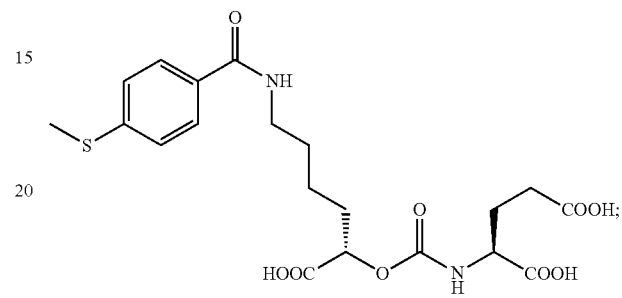
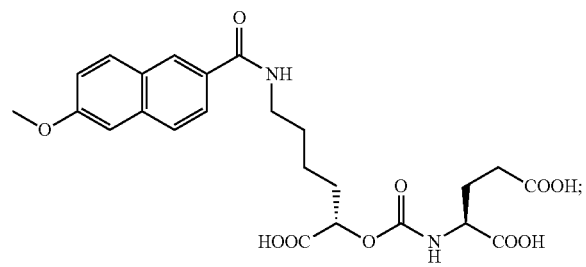
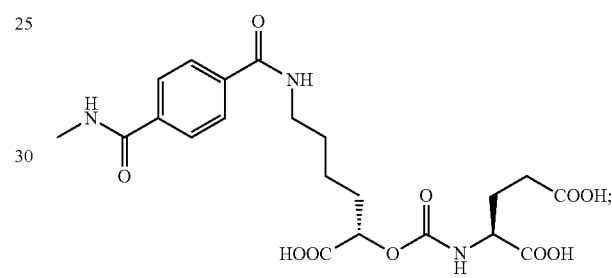
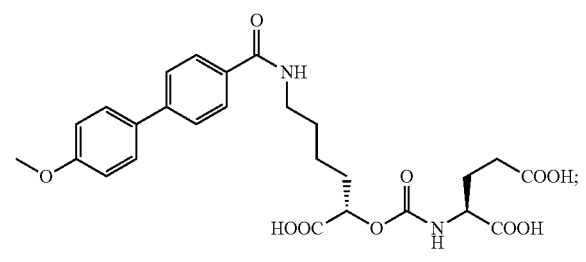
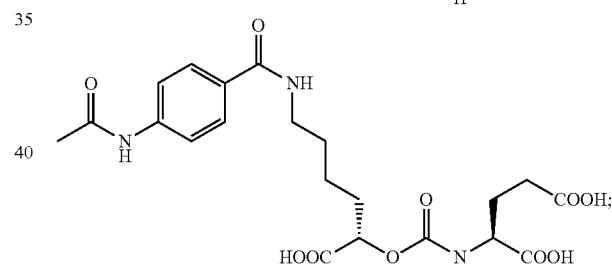
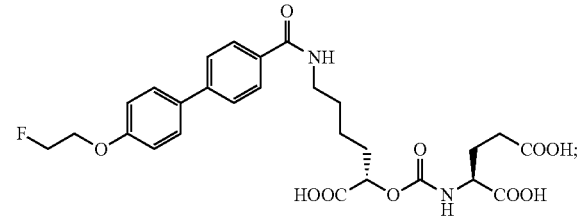
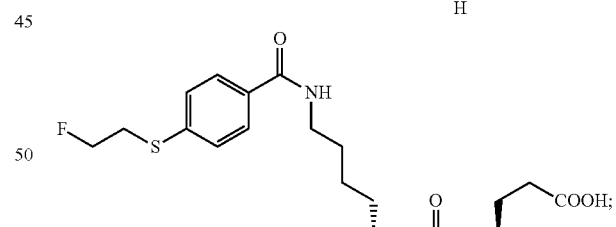
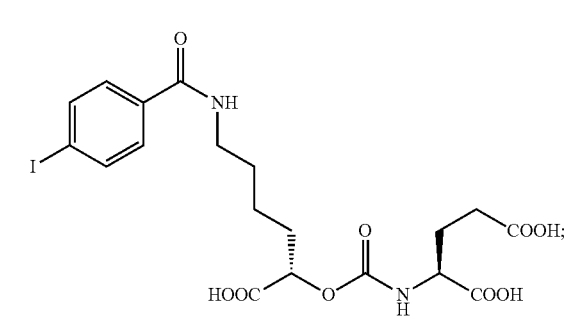
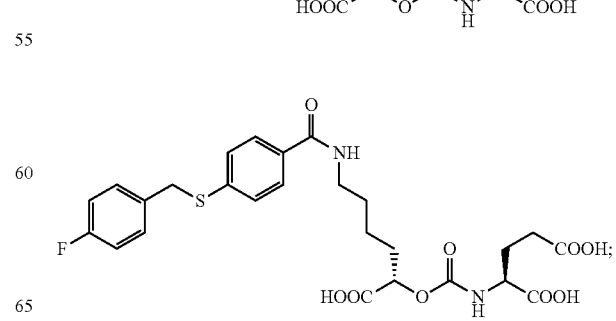

13
-continued
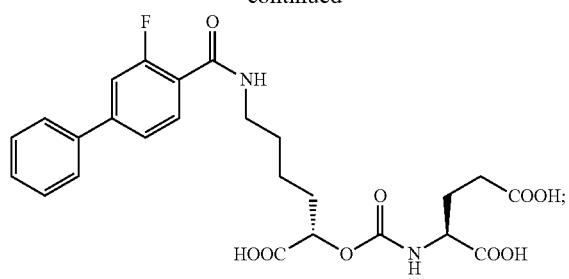
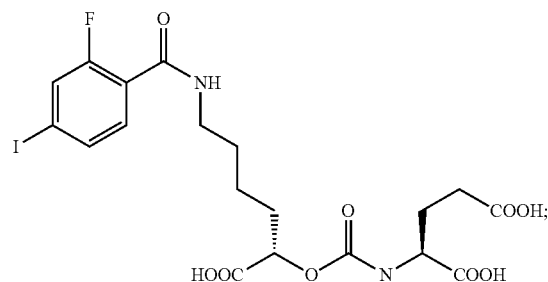
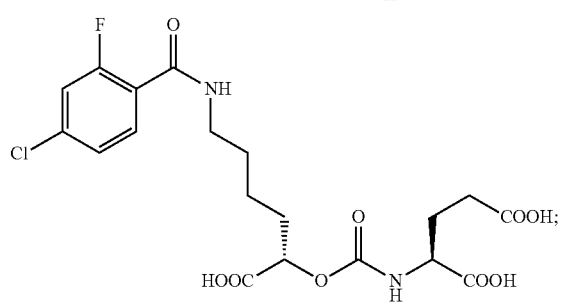
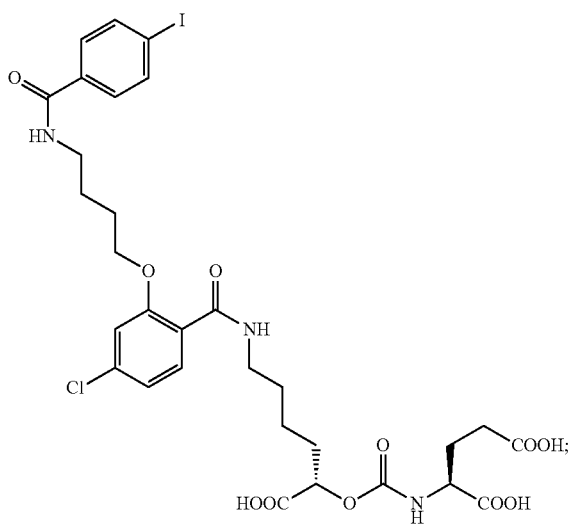
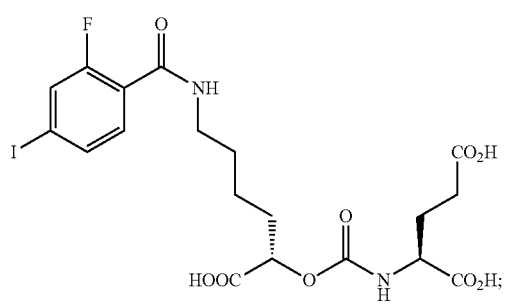
14
-continued
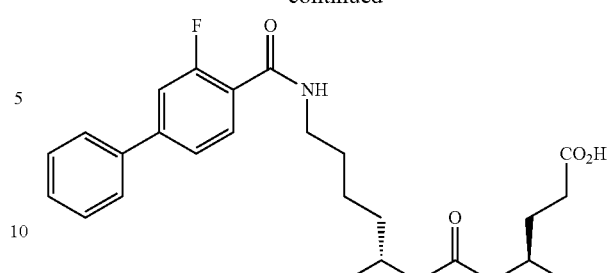
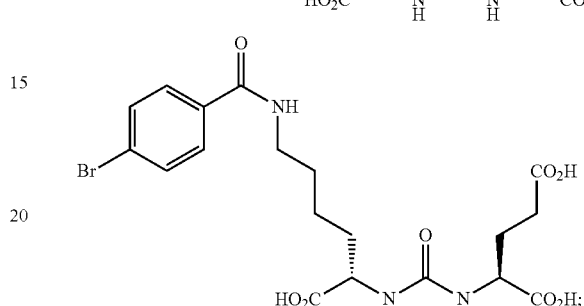
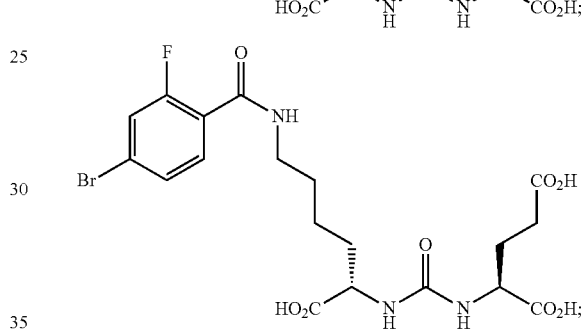
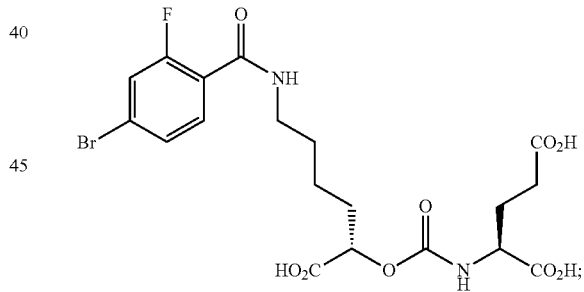
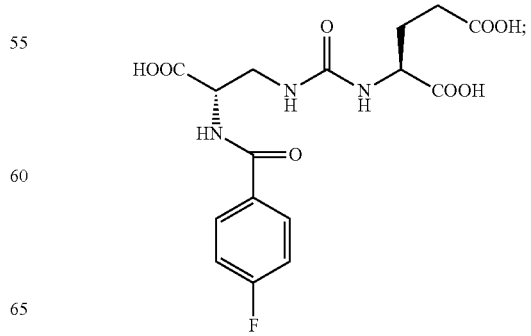

15
-continued
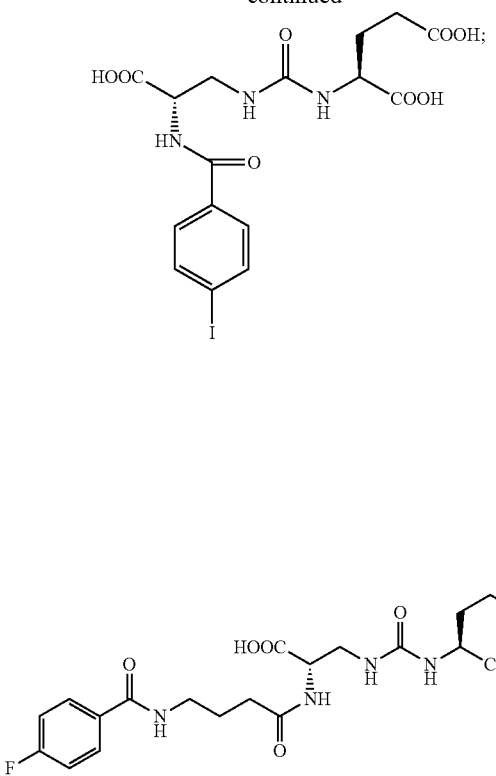
16
-continued
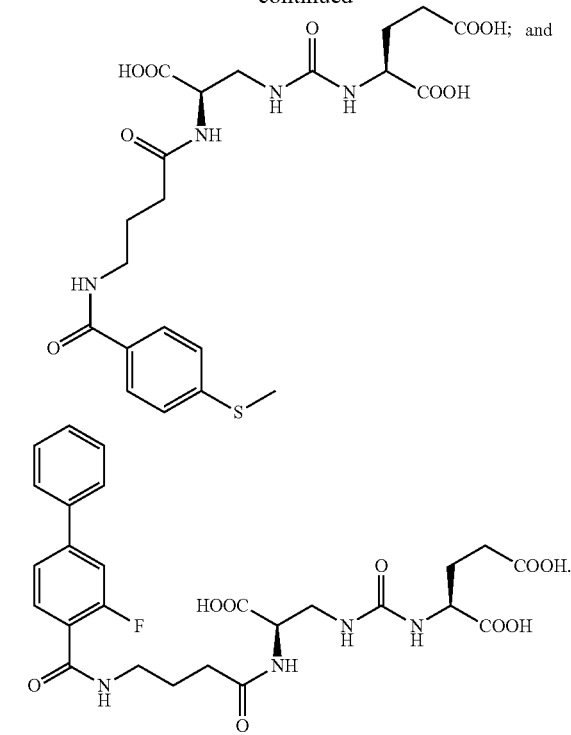
In yet more particular embodiments, the compound of formula (I) is selected from the group consisting of:
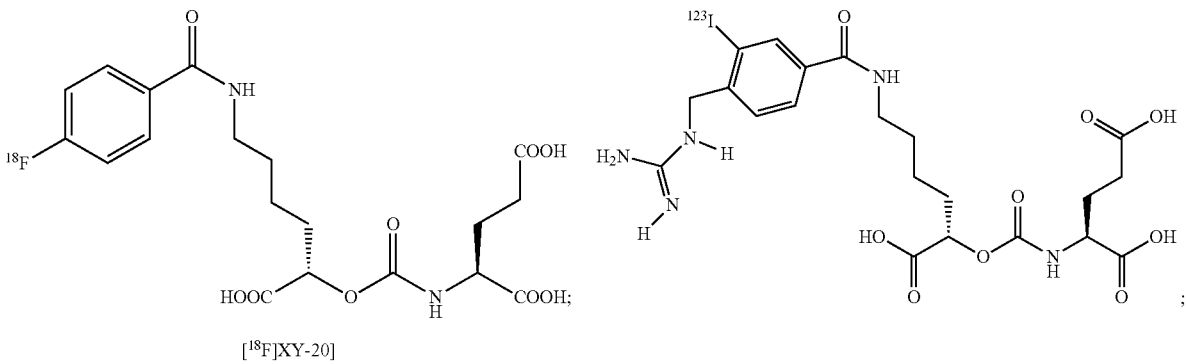
[$^{18}$F]XY-20
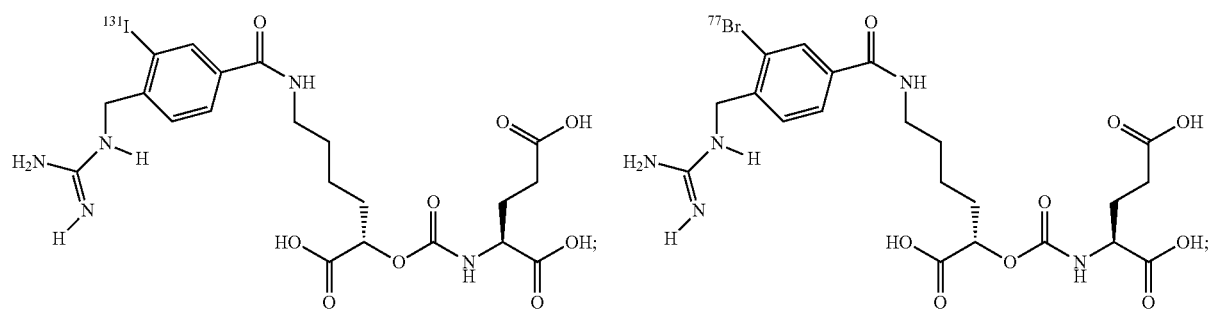

-continued
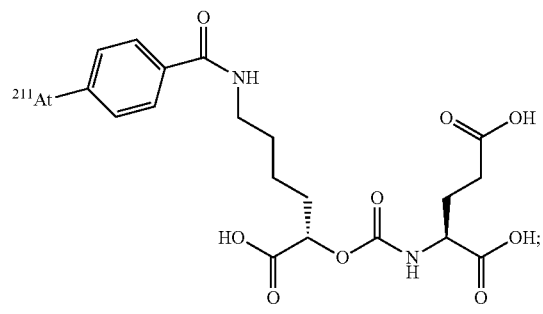
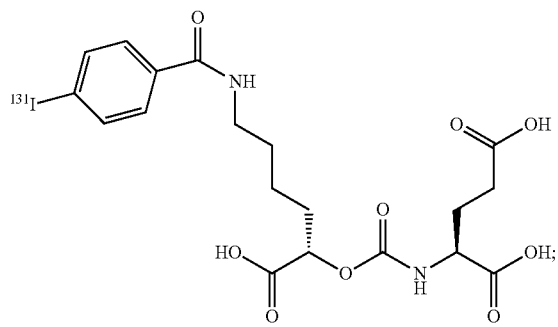
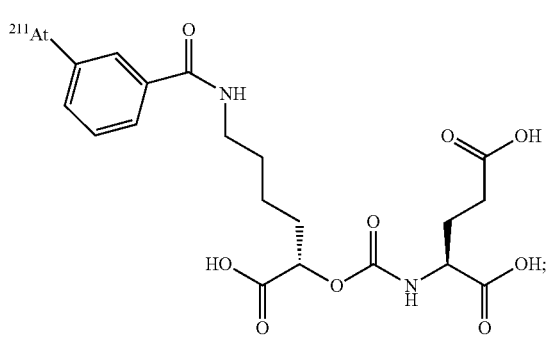
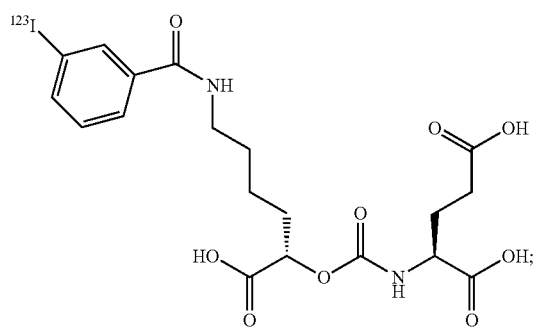
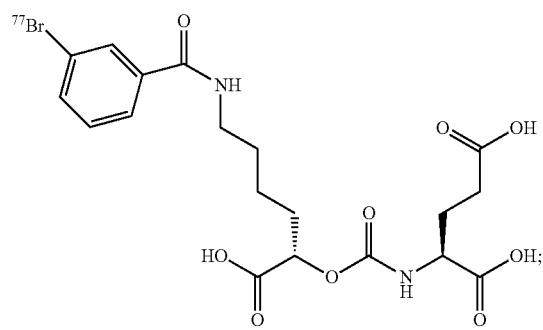
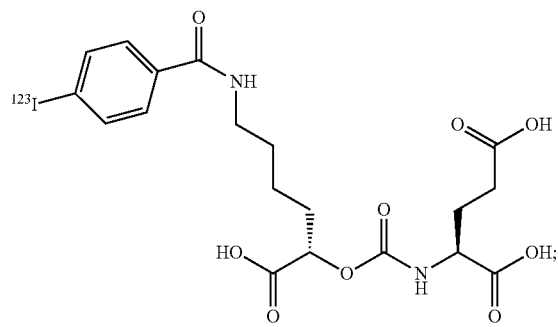
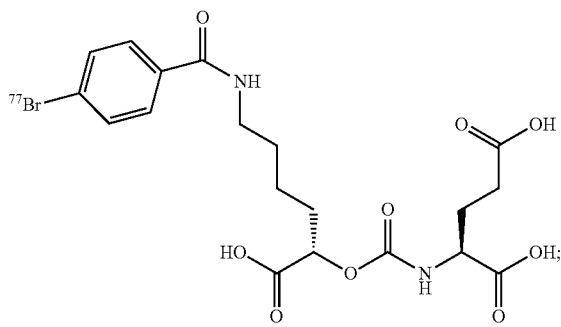
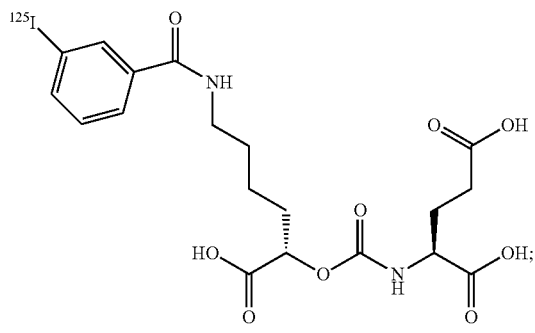
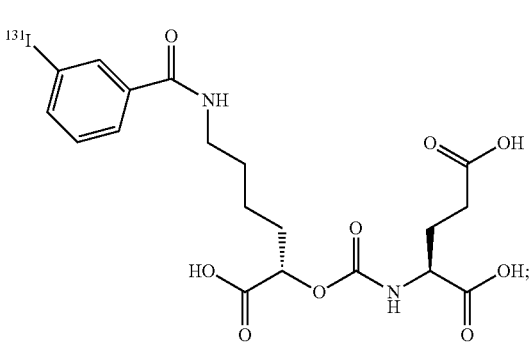
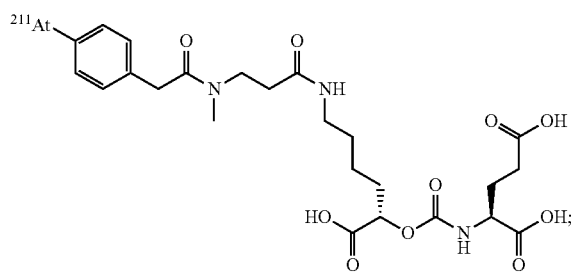

-continued
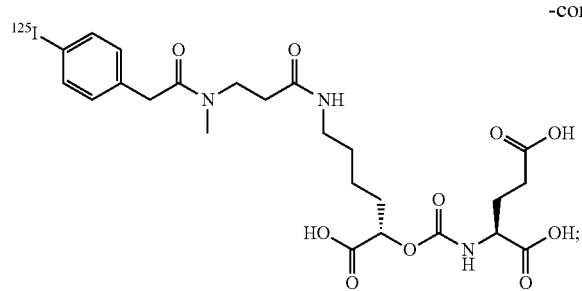
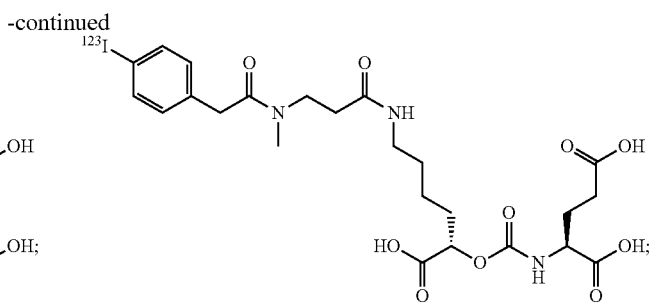
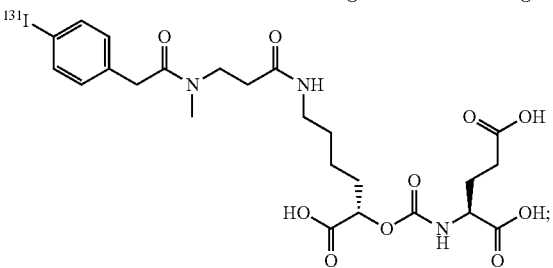
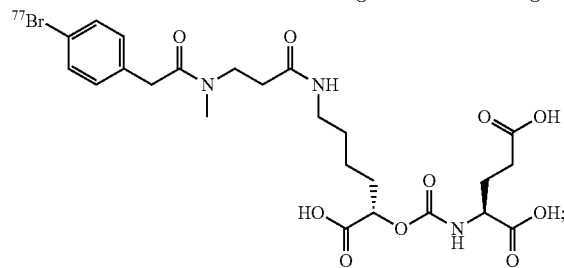
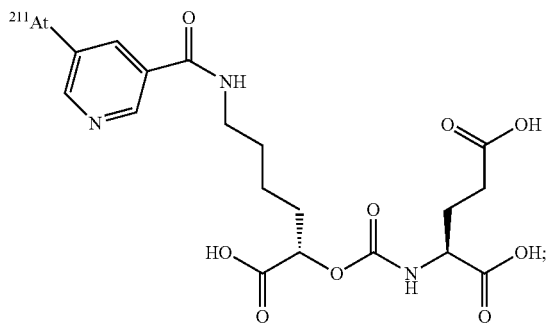
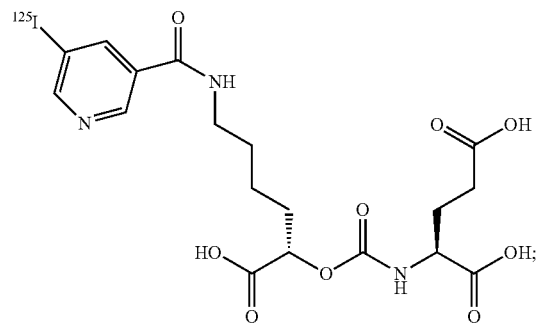
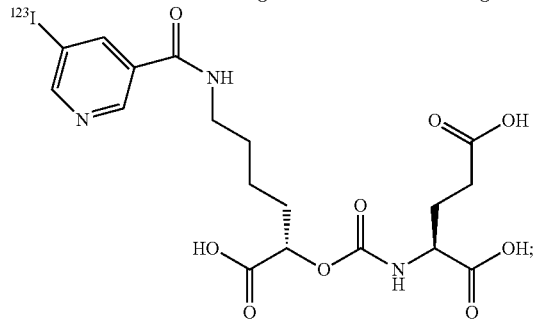
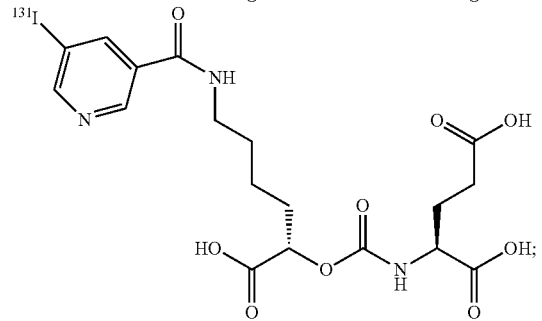
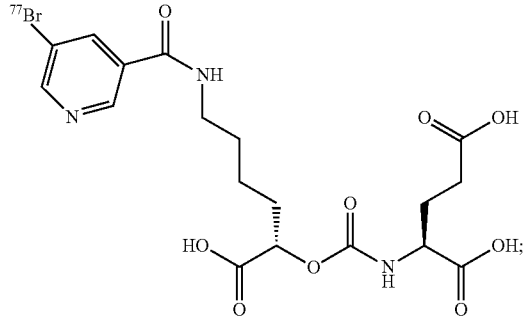
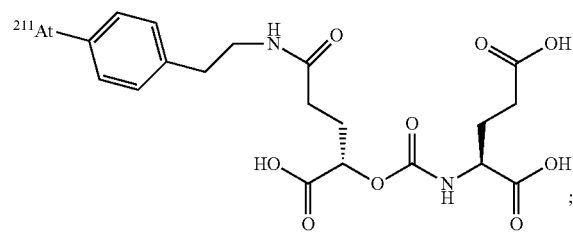
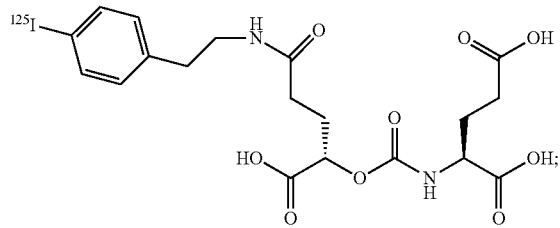
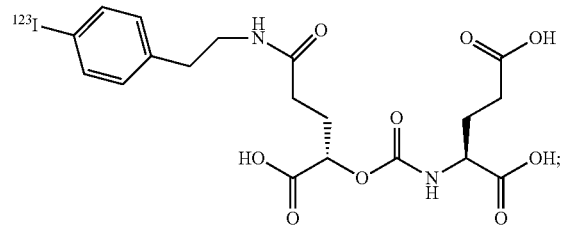

-continued
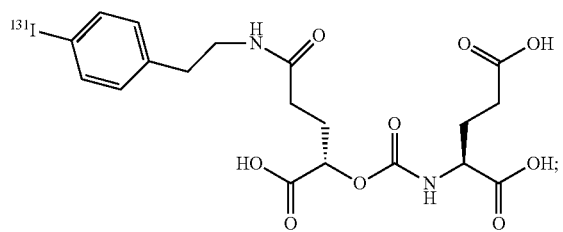
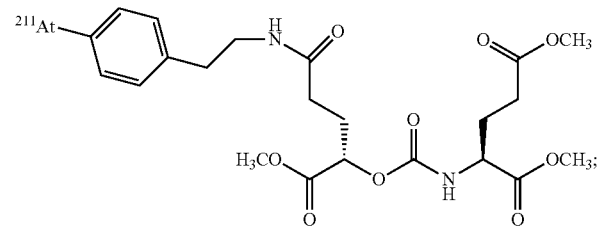
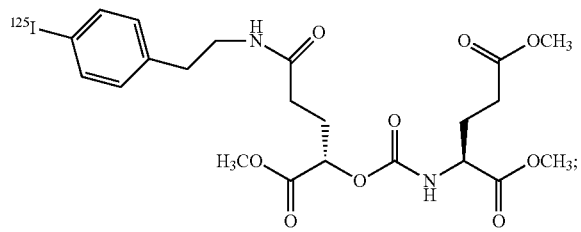
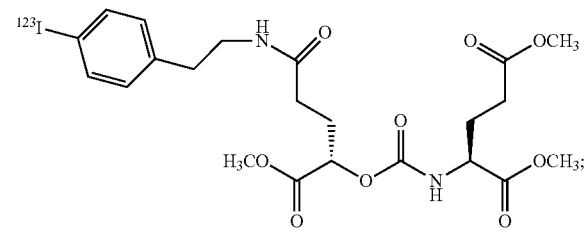
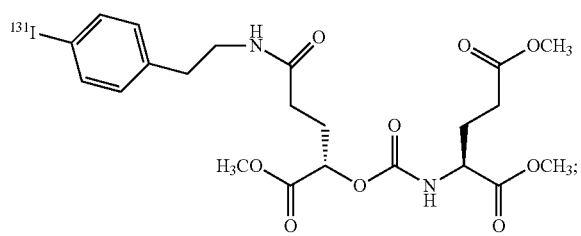
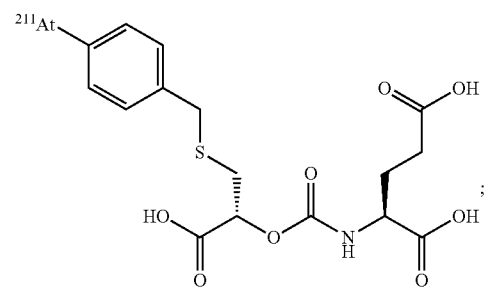
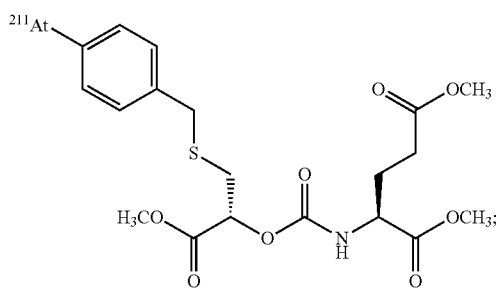
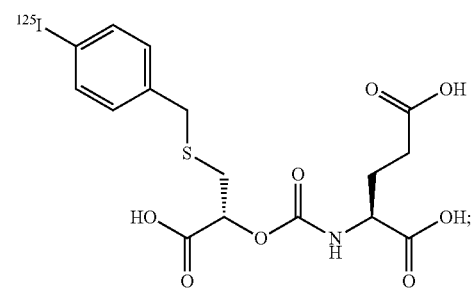
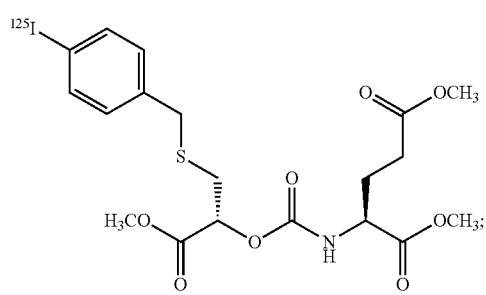
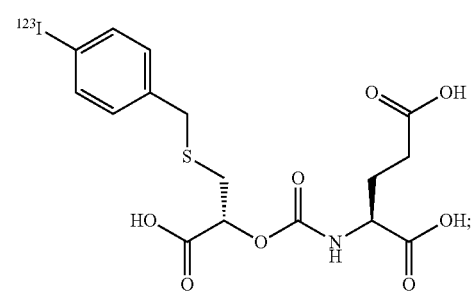
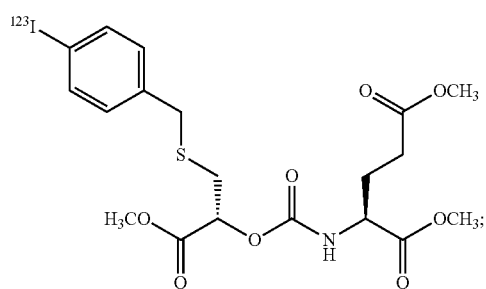
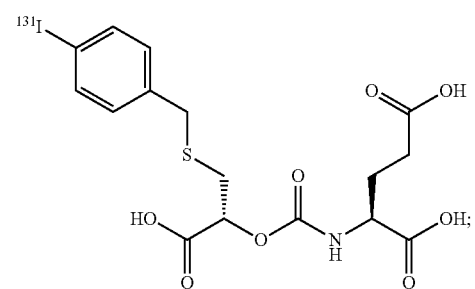

23
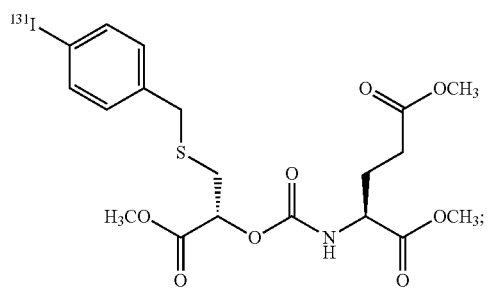
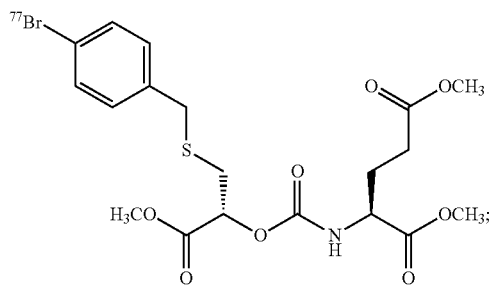
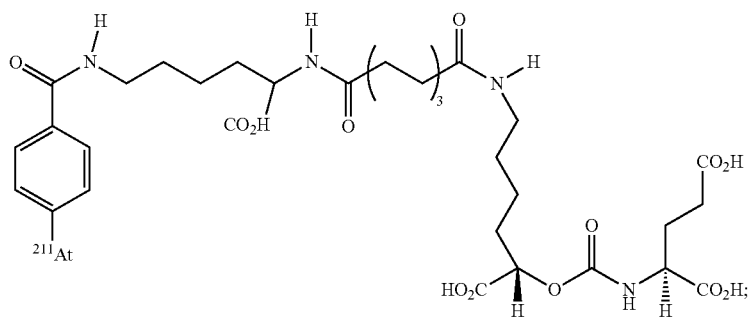
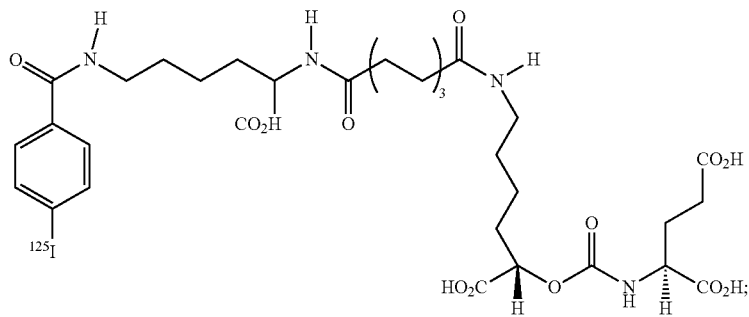
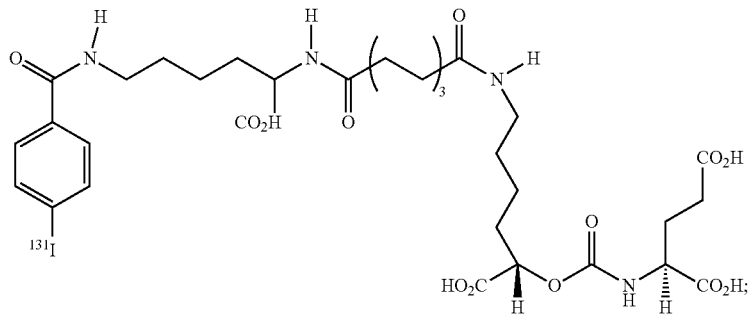
24
-continued
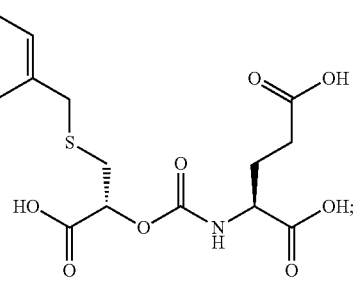

-continued
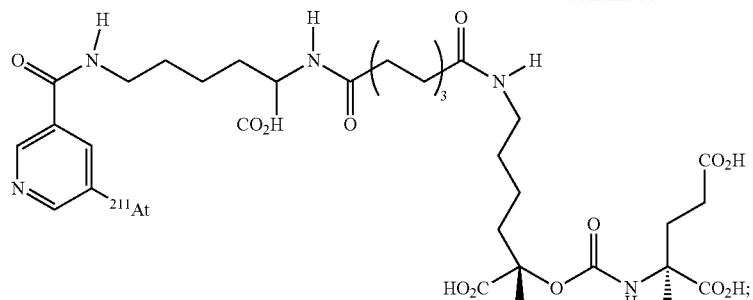
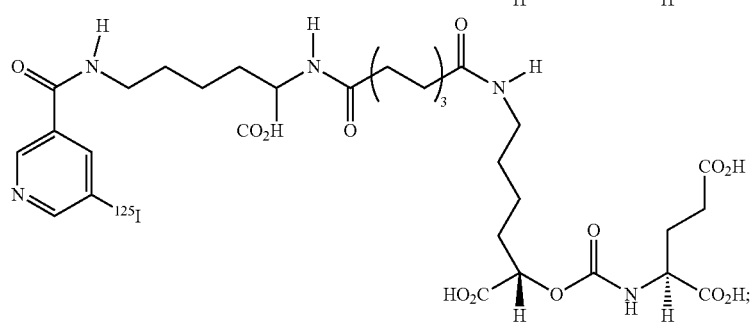
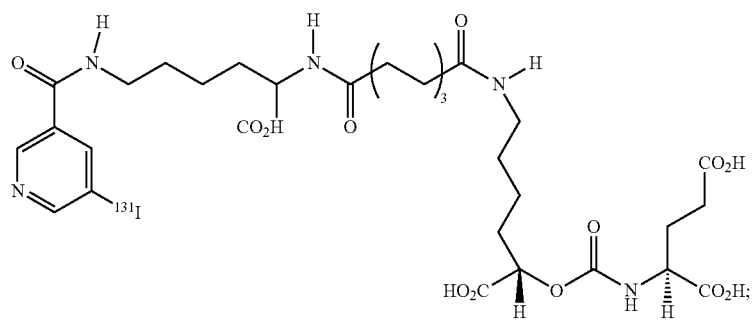
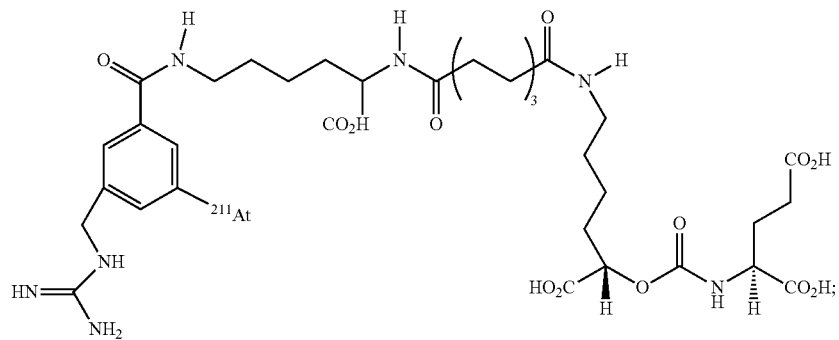
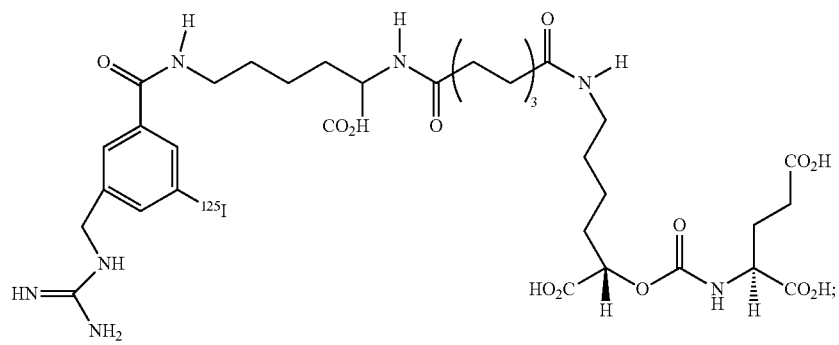

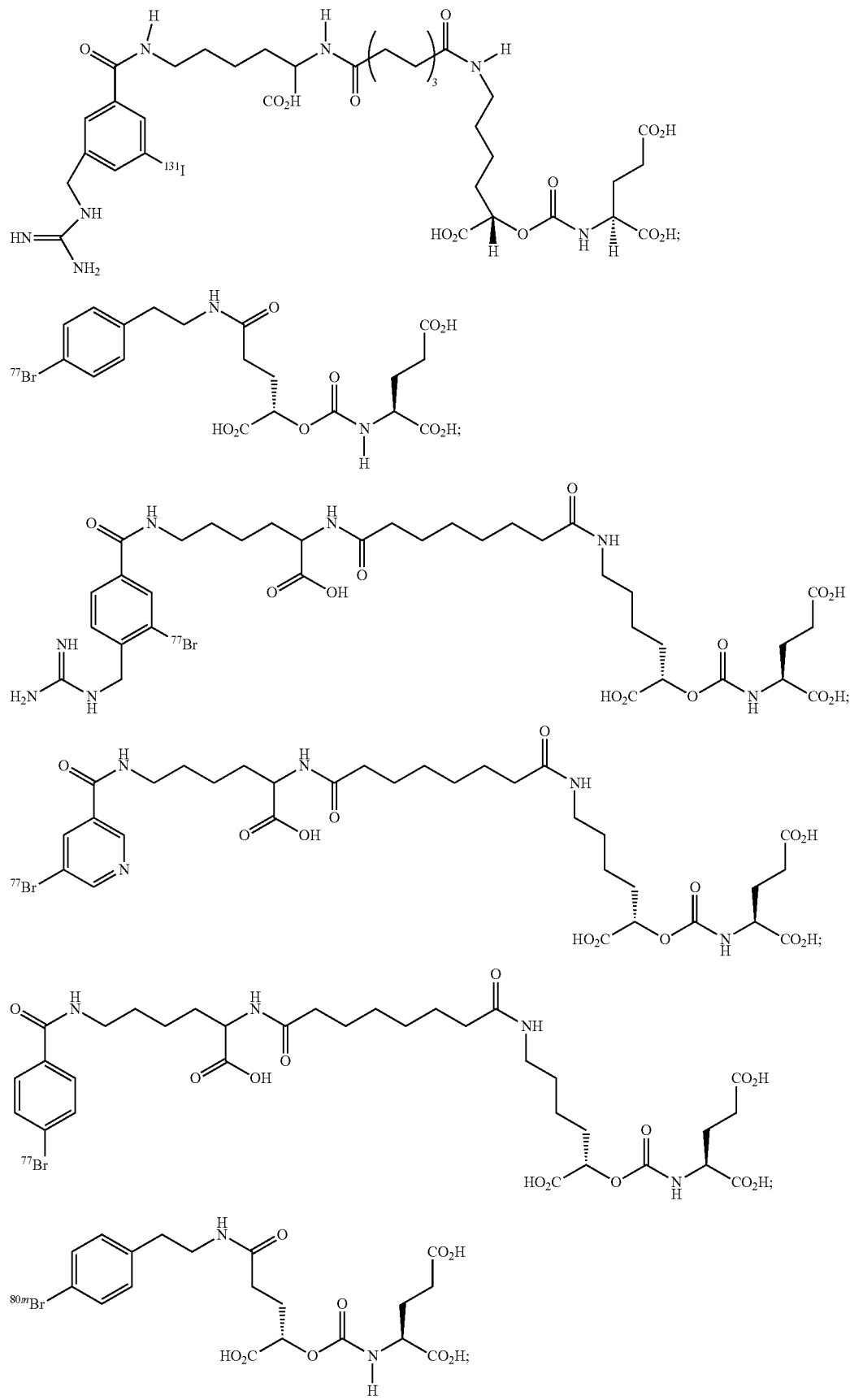

-continued

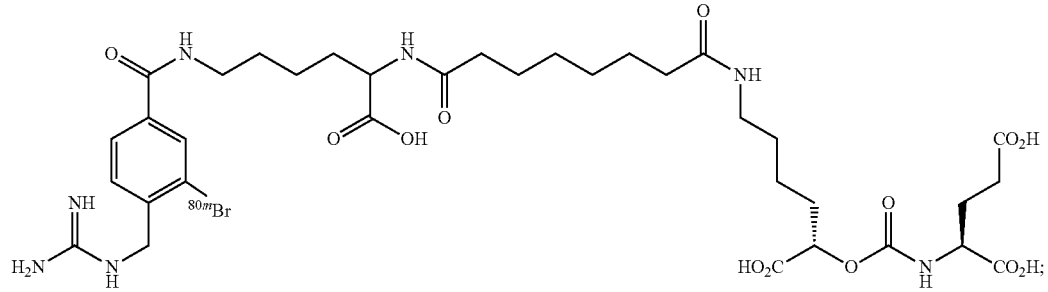

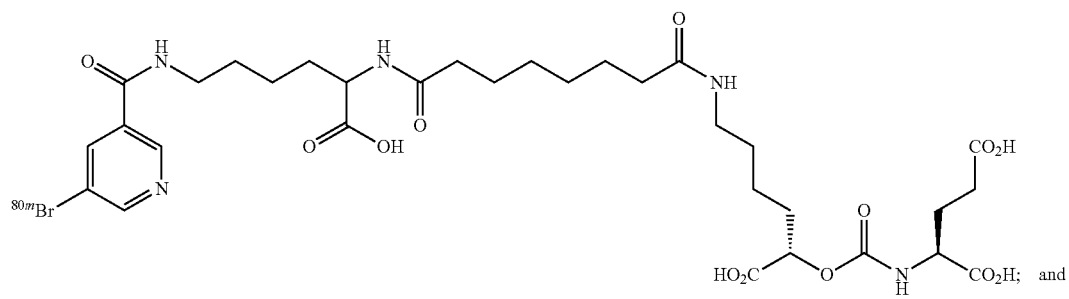
and

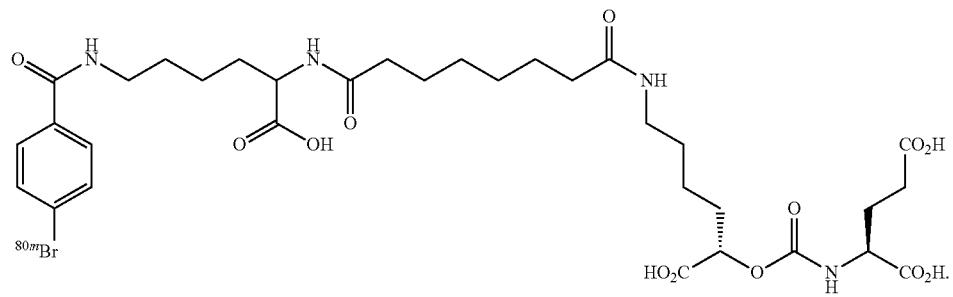

In some embodiments, the photosensitizing dye suitable for imaging and/or photodynamic therapy is a fluorescent dye moiety which emits in the visible or near infrared spectrum, wherein the fluorescent dye moiety comprises carbocyanine, indocarbocyanine, oxacarbocyanine, thiacarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS; and wherein $R_1$ or $R_2$ can optionally be a radioactive isotope suitable for imaging or radiotherapy or optionally substituted with said radioisotope.

In specific embodiments, the fluorescent dye moiety is selected from the group consisting of:

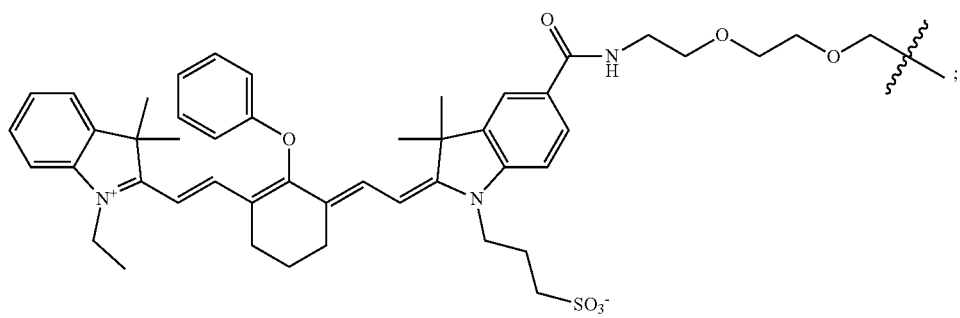

-continued
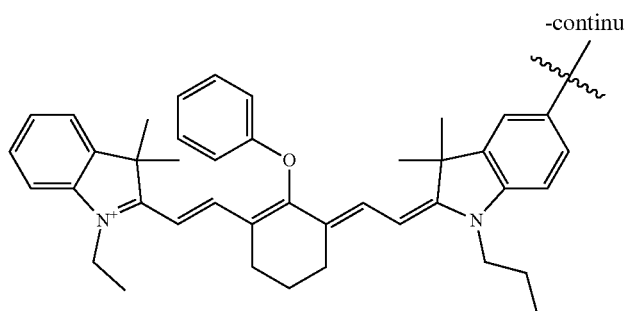
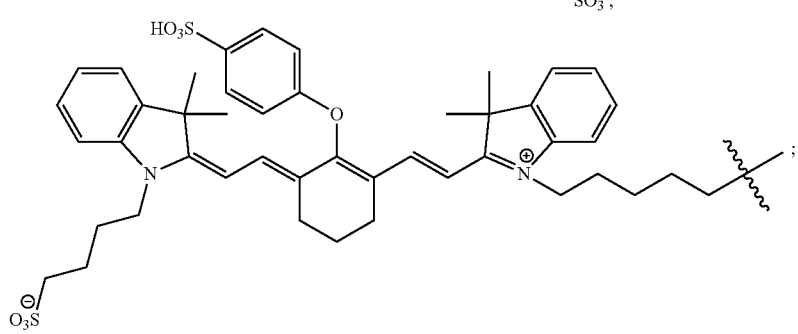
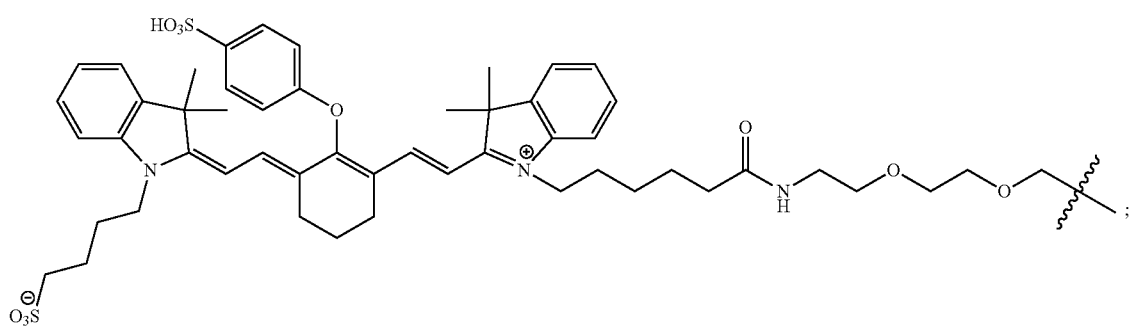
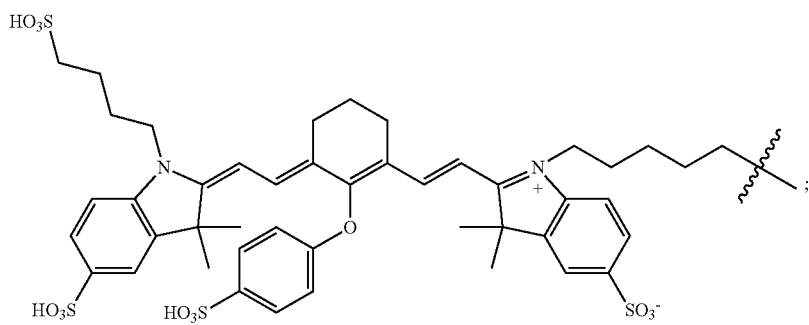
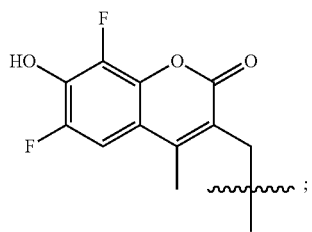

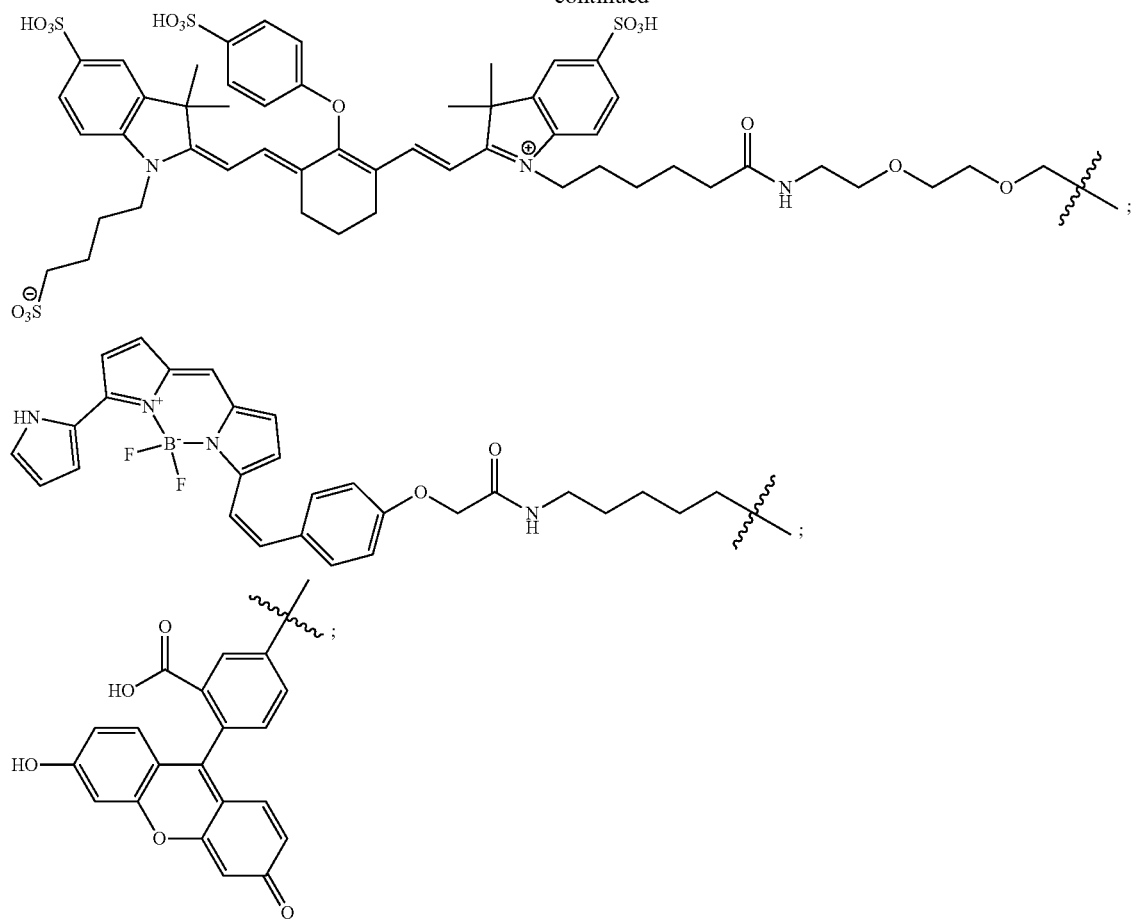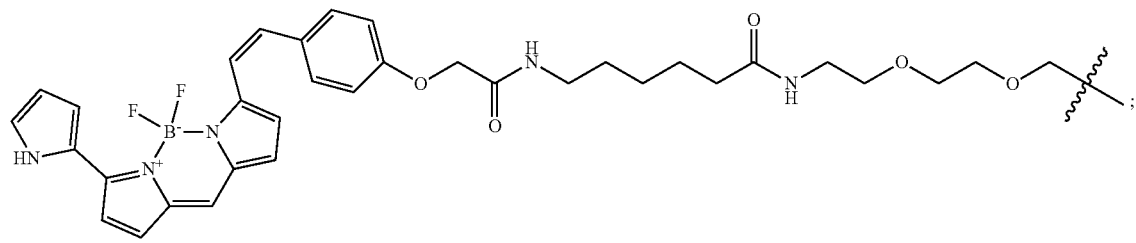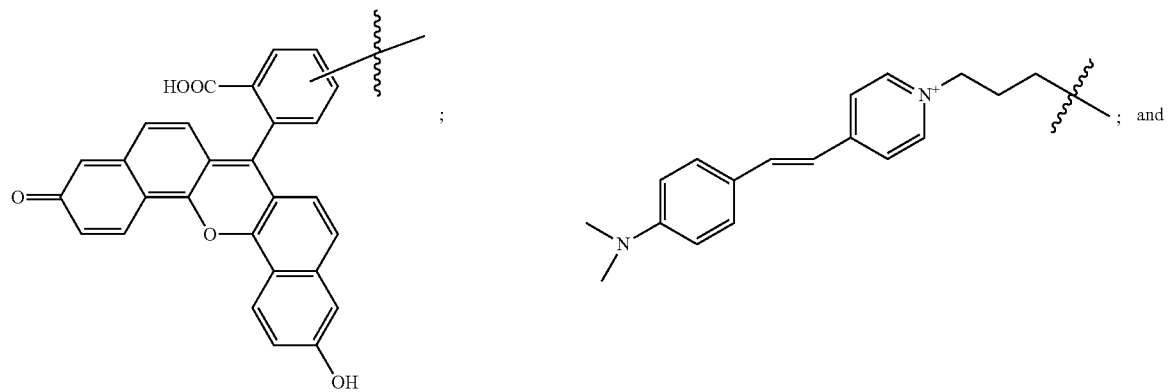

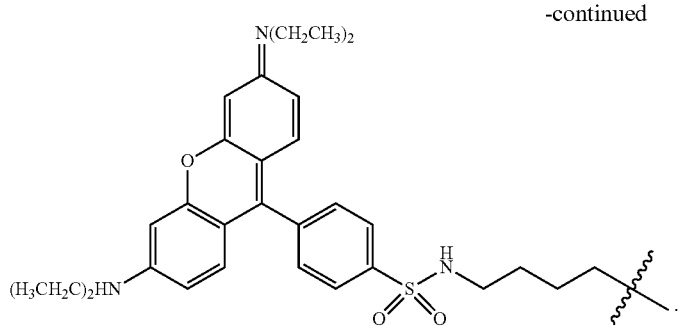

In more specific embodiments, the compound of formula (I) is

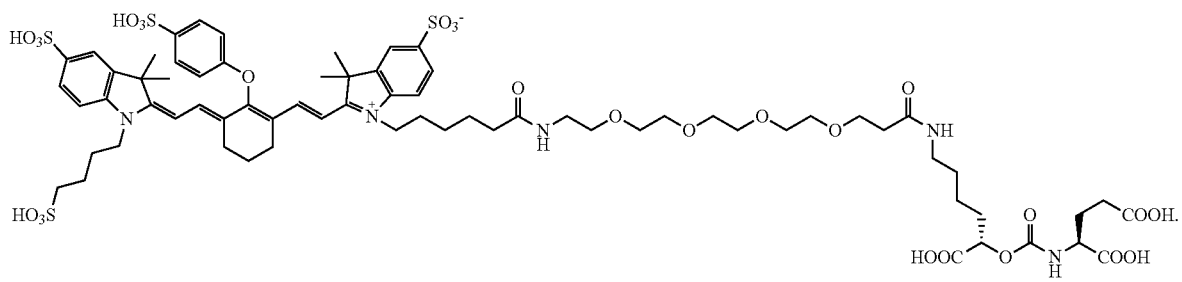

B. Methods of Using Compounds of Formula (I) or Formula (II) for Imaging a PSMA-Expressing Tumor or Cell In some embodiments, the presently disclosed subject matter provides a method for imaging one or more prostate-specific membrane antigen (PSMA)-expressing tumors or cells, the method comprising contacting the one or more tumors or cells with an effective amount of a compound of formula (I and/or formula (II), including compounds of formula (Ia), (Ib), (Ic), and (IIa), and making an image, the compound of formula (I) or formula (II) comprising:

wherein the subunits associate with elements $p_1$, $p_2$, $p_3$ and $p_4$ may be in any order; Z is tetrazole or $CO_2Q$; Q is H or a protecting group; X is O or NH; q is an integer selected from the group consisting of 0 and 1; t is an integer selected from the group consisting of 1, 2, 3, and 4; $p_2$ is an integer selected from the group consisting of 0, 1, 2, and 3, and when $p_2$ is 2 or 3, each $R_1$ is the same or different; $p_1$, $p_3$, and $p_4$ are each independently 0 or 1; $m_1$ and $m_2$ are each an integer independently selected from the group consisting of 0, 1, 2, 3, 4, 5, and 6; $W_1$ is selected from the group consisting of a bond, —S—, —C(=O)—NR—, and —NR—C (=O)—; $W_2$ is selected from the group consisting of a bond, —S—, —CH$_2$—C(=O)—NR—, —C(O)—,

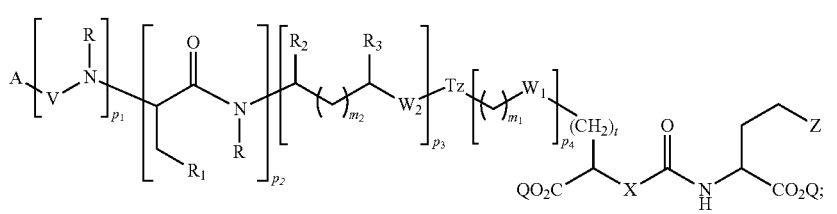

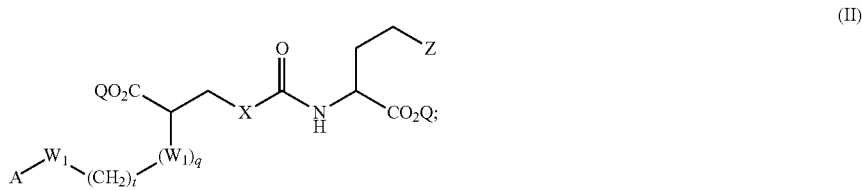

—NRC(O)—, —NR'C(O)NR—, —NRC(S)NR'$_2$—, —NRC(O)O—, —OC(O)NR—, —OC(O)—, —C(O)NR—, —NR—C(O)—, —C(O)O—, —(O—CH$_2$—CH$_2$)$_q$— and —(CH$_2$—CH$_2$—O)$_q$—, wherein q is selected from the group consisting of 1, 2, 3, 4, 5, 6, 7, and 8; each R is independently H, C$_1$-C$_6$ alkyl, C$_2$-C$_{12}$ aryl, and C$_4$-C$_{16}$ alkylaryl; Tz is a triazole group that can be present or absent and is selected from the group consisting of

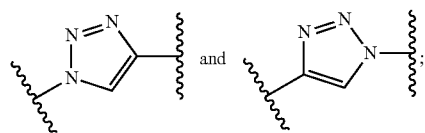 [SMILES: *c1cn(*)nn1 ; *c1cn(*)nn1]

each R$_1$ is independently H, C$_1$-C$_6$ alkyl, C$_2$-C$_{12}$ aryl or C$_4$-C$_{16}$ alkylaryl; R$_2$ and R$_3$ are each independently H and CO$_2$R$_4$, wherein R$_4$ is selected from the group consisting of H, C$_1$-C$_6$ alkyl, C$_2$-C$_{12}$ aryl, and C$_4$-C$_{16}$ alkylaryl, wherein when one of R$_2$ or R$_3$ is CO$_2$R$_4$, then the other is H; V is selected from the group consisting of —C(O)—, —C(S)—, —NRC(O)—, —NRC(S)—, and —OC(O)—; A is selected from the group consisting of naphthyl, biphenyl, substituted or unsubstituted aryl, substituted or unsubstituted heteroaryl, each of which can optionally comprise one or more radioactive isotope suitable for imaging and/or radiotherapy, and photosensitizing dye suitable for imaging and/or photodynamic therapy.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor.

By "making an image", it is meant using PET, SPECT or florescent optical imaging to form an image of a cell, tissue, tumor, part of body, and the like. The presently disclosed methods may include one or more radioactive isotopes capable of emitting radiation suitable for detection with PET or SPECT or a photosensitizing dye suitable for fluorescent optical imaging.

In some embodiments, the image is made using PET the image is made using positron emission tomography (PET) and the radiohalogen is selected from the group consisting of $^{18}$F or $^{124}$I.

In some other embodiments, the image is made using Single-photon emission computed tomography (SPECT) and the radiohalogen is selected from the group consisting of $^{77}$Br, $^{131}$I, $^{125}$I, and $^{123}$I.

In yet some other embodiments, the image is made using florescent optical imaging and the photosensitizing dye suitable for imaging is selected from the group consisting of

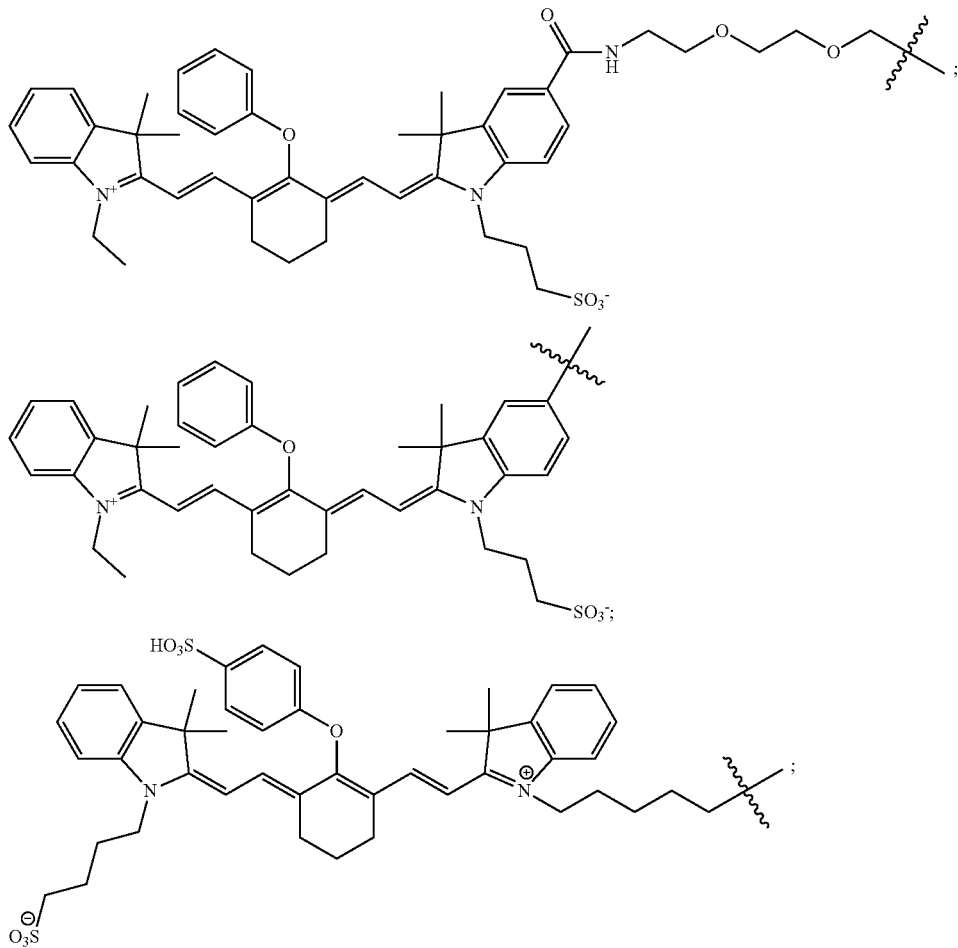

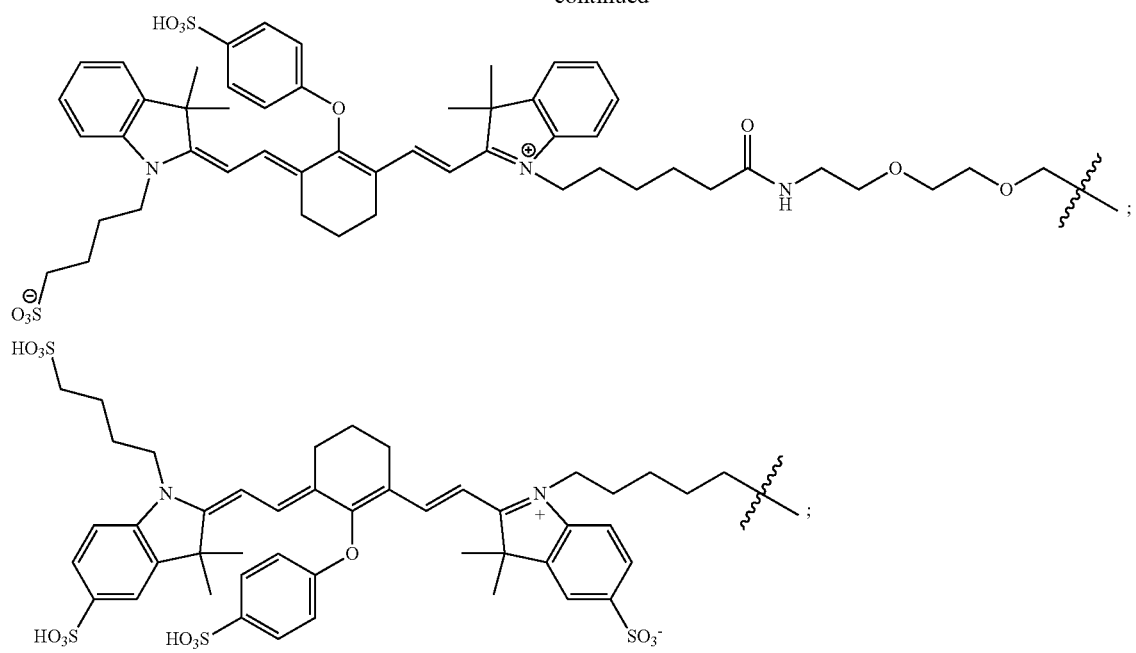
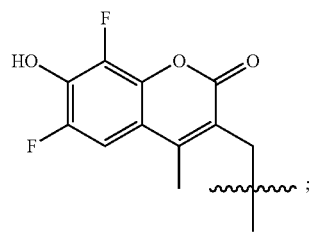
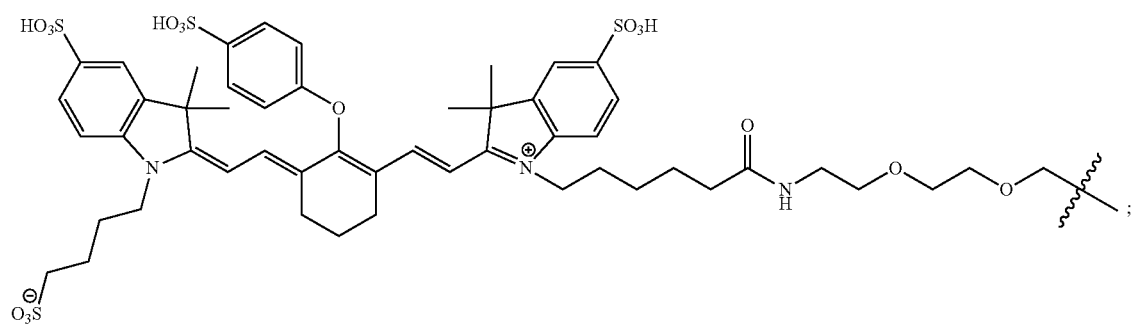
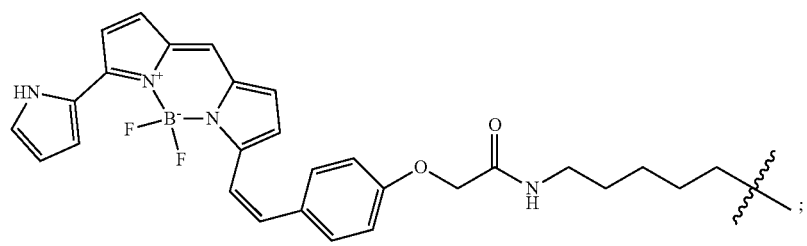

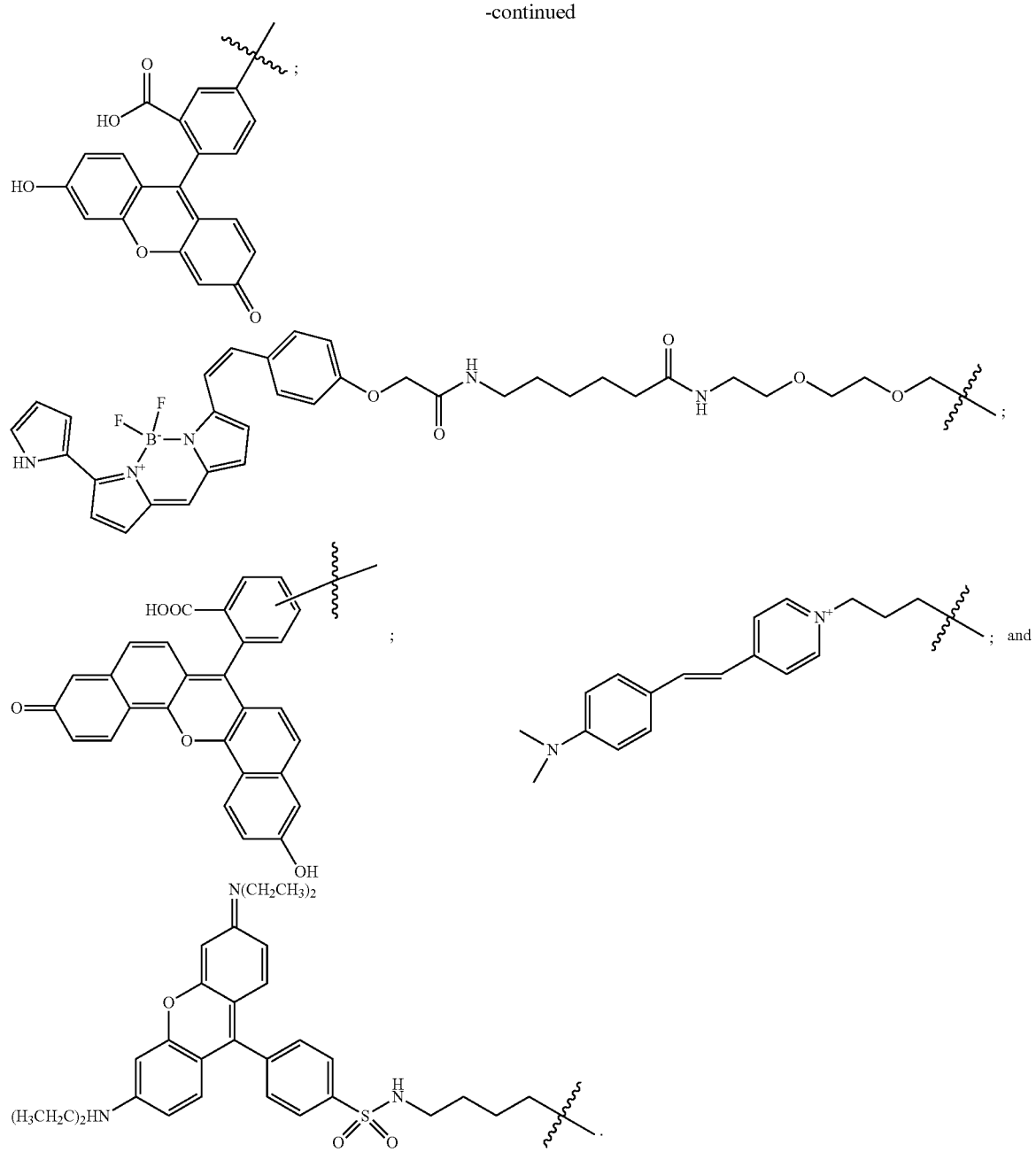

In certain embodiments, the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In yet more certain embodiments, the one or more PSMA-expressing tumors or cells is a prostate tumor or cell.

In some embodiments, the one or more PSMA-expressing tumors or cells is in vitro, in vivo, or ex vivo. In particular embodiments, the one or more PSMA-expressing tumors or cells is present in a subject.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like;

felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

It is preferable to have the compound comprising the imaging agent to localize to the tumor or cell quickly after administration so as to minimize any side effects to the subject. Accordingly, in some embodiments, the compound comprising the imaging agent substantially localizes to the tumor or cell within about 60 minutes to about 240 minutes of administration and, in some embodiments, about 60 minutes. In other embodiments, the compound comprising the imaging agent substantially localizes to the tumor or cell within about 30 minutes of administration. In still other embodiments, the compound comprising the imaging agent substantially localizes to the tumor or cell within about 10 minutes of administration.

It is also preferable that the compounds of the presently disclosed subject matter are excreted from tissues of the body quickly to prevent prolonged exposure to the radiation of the radiolabeled compound administered to the patient. Typically compounds of the presently disclosed subject matter are eliminated from the body in less than about 24 hours. More preferably, compounds of the presently disclosed subject matter are eliminated from the body in less than about 16 hours, 12 hours, 8 hours, 6 hours, 4 hours, 2 hours, 90 minutes, or 60 minutes.

In some embodiments, the presently disclosed methods comprise clearance of the compound comprising the imaging agent from the tumor or cell in the subject. At least one advantage of the presently disclosed methods is that, in some embodiments, there is more rapid clearance of the compound comprising the imaging agent from the kidneys than from the tumor of the subject.

In other embodiments, for example for fluorescence guided surgery and biopsy of PSMA positive tumors and tissues the compound comprising the photosensitizing dye suitable for imaging is visible at about 4 hours after injection and presents the brightest signal at about 24 hours after injection.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

A "tumor," as used herein, refers to all neoplastic cell growth and proliferation, whether malignant or benign, and all precancerous and cancerous cells and tissues.

In some embodiments, the tumor cells express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculture. Therefore, methods of the presently disclosed subject matter can be used to image nearly all solid tumors including, but not limited to, lung, renal cell, glioblastoma, pancreas, bladder, sarcoma, melanoma, breast, colon, germ cell, pheochromocytoma, esophageal, and stomach tumors. Also, certain benign lesions and tissues including, but not limited to, endometrium, schwannoma and Barrett's esophagus, can be imaged according to the presently disclosed methods.

C. Methods of Using Compounds of Formula (I) or Formula (II) for Treating a Disease or Condition Associated with One or More PSMA-Expressing Tumor or Cell In some embodiments, the presently disclosed subject matter provides a method for treating or preventing a disease or condition associate with one or more PSMA expressing tumors or cells, the method comprising administering at least one compound of formula (I), and/or formula (II), including compounds of formula (Ia), (Ib), (Ic), and (IIa), to a subject in an amount effective to treat or prevent the disease or condition, the compound of formula (I) and/or formula (II) comprising:

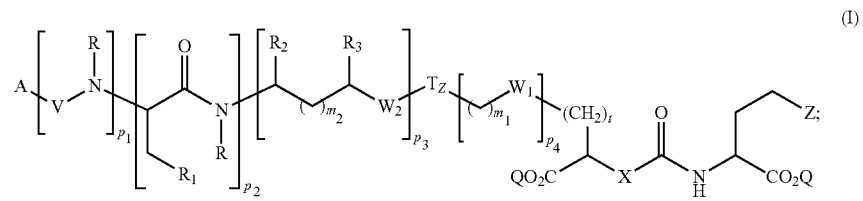

-continued

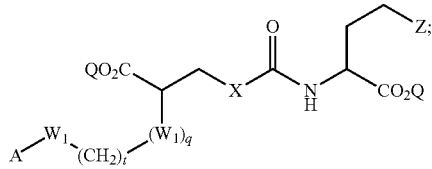

wherein the subunits associate with elements $p_1$, $p_2$, $p_3$ and $p_4$ may be in any order; Z is tetrazole or $CO_2Q$; Q is H or a protecting group; X is O or NH; q is an integer selected from the group consisting of 0 and 1; t is an integer selected from the group consisting of 1, 2, 3, and 4; $p_2$ is an integer selected from the group consisting of 0, 1, 2, and 3, and when $p_2$ is 2 or 3, each $R_1$ is the same or different; $p_1$, $p_3$, and $p_4$ are each independently 0 or 1; $m_1$ and $m_2$ are each an integer independently selected from the group consisting of 0, 1, 2, 3, 4, 5, and 6; $W_1$ is selected from the group consisting of a bond, —S—, —C(=O)—NR—, and —NR—C(=O)—; $W_2$ is selected from the group consisting of a bond, —S—, —CH$_2$—C(=O)—NR—, —C(O)—, —NRC(O)—, —NRC(O)NR—, —NRC(S)NR—, —NRC(O)O—, —OC(O)NR—, —OC(O)—, —C(O)NR—, —NR—C(O)—, —C(O)O—, —(O—CH$_2$—CH$_2$)$_q$- and —(CH$_2$—CH$_2$—O)$_q$—, wherein q is selected from the group consisting of 1, 2, 3, 4, 5, 6, 7, and 8; each R is independently H, $C_1$-$C_6$ alkyl, $C_2$-$C_{12}$ aryl, and $C_4$-$C_{16}$ alkylaryl; Tz is a triazole group that can be present or absent and is selected from the group consisting of (II)

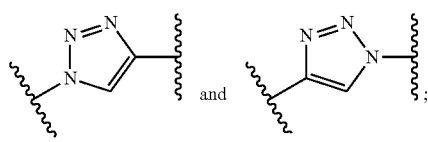 [SMILES: *c1cn(*)nn1 ; *c1cn(*)nn1]

each $R_1$ is independently H, $C_1$-$C_6$ alkyl, $C_2$-$C_{12}$ aryl or $C_4$-$C_{16}$ alkylaryl; $R_2$ and $R_3$ are each independently H and $CO_2R_4$, wherein $R_5$ is selected from the group consisting of H, $C_1$-$C_6$ alkyl, $C_2$-$C_{12}$ aryl, and $C_4$-$C_{16}$ alkylaryl, wherein when one of $R_2$ or $R_3$ is $CO_2R_4$, then the other is H; V is selected from the group consisting of —C(O)—, —C(S)—, —NRC(O)—, —NRC(S)—, and —OC(O)—; A is selected from the group consisting of naphthyl, biphenyl, substituted or unsubstituted aryl, substituted or unsubstituted heteroaryl, each of which can optionally comprise one or more radioactive isotope suitable for radiotherapy, and photosensitizing dye suitable for photodynamic therapy.

In further embodiments, the radiohalogen suitable for radiotherapy is selected from the group consisting of $^{80m}$Br, $^{77}$Br, $^{125}$I, $^{123}$I, $^{131}$I and $^{211}$At. In yet other embodiment, wherein the photosensitizing dye suitable for photodynamic therapy is selected from the group consisting of

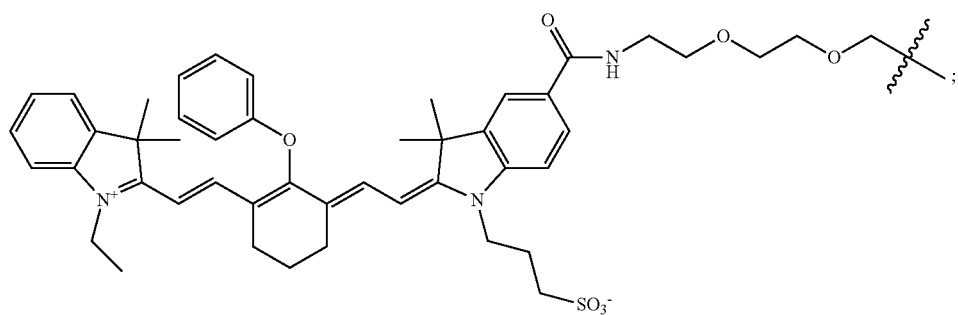

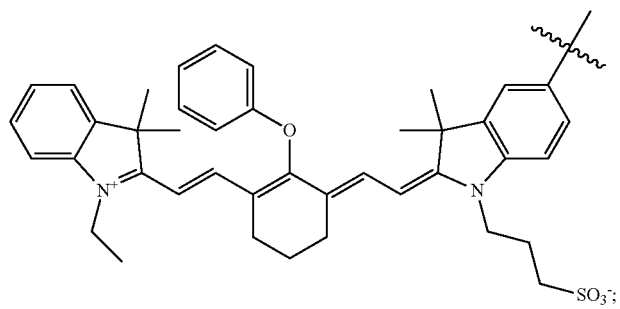

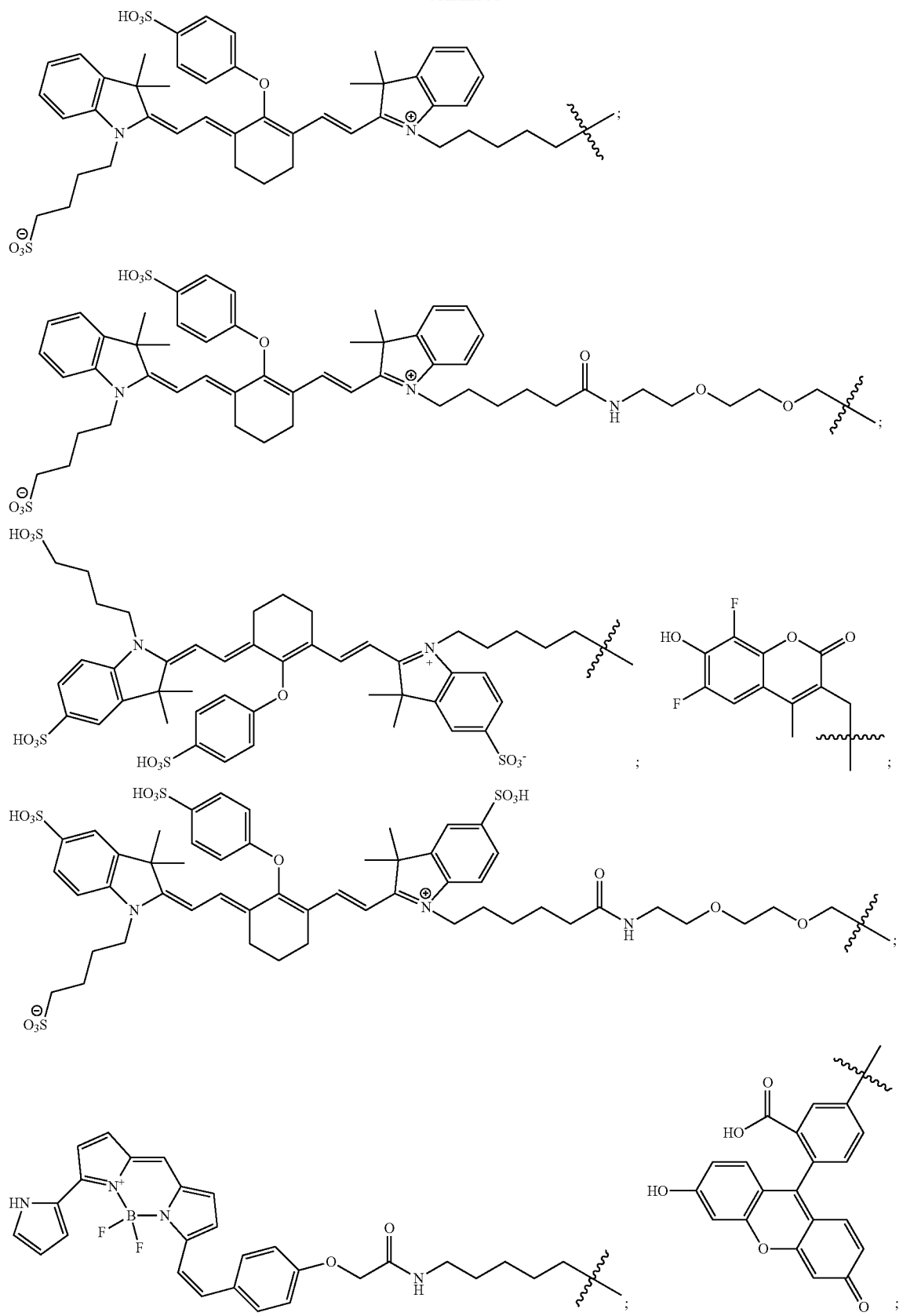

-continued

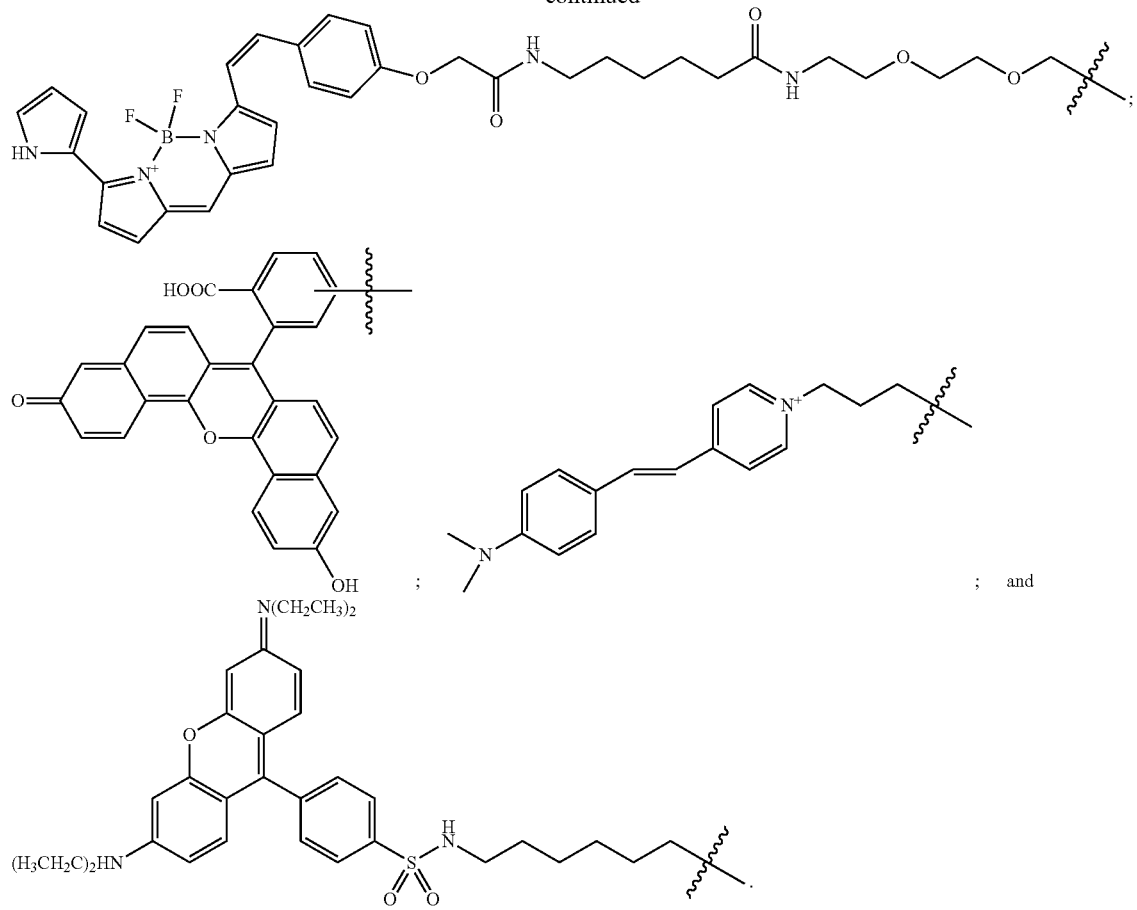

In specific embodiments, the disease or condition is a prostate cancer, renal cancer, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, adenomas, and tumor neovasculature. In more specific embodiments, the disease or condition is prostate cancer. Accordingly, the presently disclosed compounds can be administered prophylactically to prevent or reduce the incidence or recurrence of the cancer or the tumor neovasculature.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within a subject, or circulate in the blood stream as independent cells, for example, leukemic cells.

A cancer can include, but is not limited to, renal cancer, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In more specific embodiments, the disease or condition is prostate cancer. In some embodiments, a detectably effective amount of the therapeutic agent of the presently disclosed methods is administered to a subject.

D. Definitions i. Chemical Definitions

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

As used herein, where an internal substituent is flanked by bonds (for example, —NRC(O)—) the order of the atoms is fixed, the orientation of the group may not be reversed, and is inserted into a structure in the orientation presented. In other words —NRC(O)— is not the same as —C(O)NR—. As used herein the term C(O) (for example —NRC(O)—) is used to indicate a carbonyl (C=O) group, where the oxygen is bonded to the carbon by a double bond.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

In certain embodiments, alkyl groups are $C_1$-$C_6$ alkyl groups or $C_1$-$C_4$ alkyl groups. The term "$C_1$-$C_6$ alkyl" as used herein means straight-chain, branched, or cyclic $C_1$-$C_6$ hydrocarbons which are completely saturated and hybrids thereof, such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^0$Pr)), butyl (including n-butyl (n-Bu, $^n$Bu), iso-butyl (i-Bu, $^i$Bu), sec-butyl (s-Bu, $^s$Bu), tert-butyl (t-Bu, $^t$Bu), or cyclobutyl (c-Bu, $^0$Bu)), and so forth.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$5—S(O)—CH$_3$, —CH$_2$—CH$_2$—S(O)$_2$—

$CH_3$, —CH=CH—O—$CH_3$, —Si$(CH_3)_3$, —$CH_2$—CH=N—$OCH_3$, —CH=CH—N$(CH_3)$—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si$(CH_3)_3$.

As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl. The alkyl group may be substituted or unsubstituted.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopropyl, cyclobutyl, cyclopentyl, cyclohexyl, and cycloheptyl.

Multicyclic cycloalkyl rings include adamantyl, octahydronaphthyl, decalin, camphor, camphane, and noradamantyl, and fused ring systems, such as dihydro- and tetrahydronaphthalene, and the like.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and alkenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—(CH$_2$)$_3$—); cyclohexylene (—C$_6$H$_{10}$—); —CH=CH— CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S— CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

As used herein, the term "alkylaryl" includes alkyl groups, as defined above, substituted by aryl groups, as defined above. The aryl group may be connected at any point on the alkyl group. The term C$_4$-C$_{16}$ alkylaryl includes alkylaryl groups having a total of 4 to 16 carbon atoms, counting the carbon atoms on the alkyl group and aryl group together. Examples of alkylaryl groups include but are not limited to benzyl (phenylmethyl), phenyl ethyl, and naphthylmethyl. The alkylaryl group may be substituted or unsubstituted. Substituents are not counted towards the total number of atoms in the alkylaryl group, so long as the total atoms in the substituent(s) are not larger than the alkylaryl group.

Further, a structure represented generally by the formula:

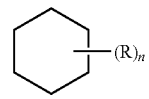

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

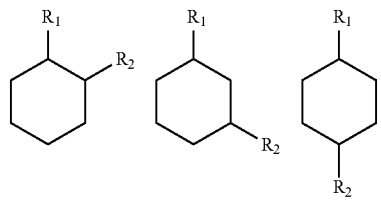

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

A substituent bearing a broken bond, such as the example shown below, means that the substituent is directly bonded to the molecule at the indicated position. No additional methylene (CH$_2$) groups are implied. The symbol ( ⁓⁓⁓⁓ ) denotes the point of attachment of a moiety to the remainder of the molecule.

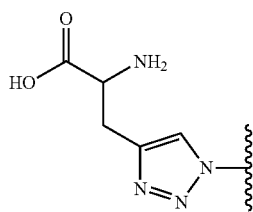 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene ($CH_2$) groups are implied unless specifically indicated.

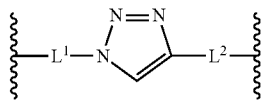

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —$CONH_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group,"

wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like also can be present in the compounds described herein, and all such stable isomers are contemplated in the presently disclosed subject matter. Cis and trans geometric isomers of the compounds of the presently disclosed subject matter are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^t$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^4$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium (H), iodine-125 ($^{125}$I) or carbon-14 ($^{14}$C). All isotopic variations of the compounds of the present disclosure, whether radioactive or not, are encompassed within the scope of the present disclosure.

ii. Pharmaceutical Salts

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20$^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

iii. Pharmaceutical Compositions

The compounds disclosed herein can be formulated into various compositions, for use in diagnostic and imaging methods. Generally, a pharmaceutical composition comprises an effective amount (e.g., a or detectably effective amount) of a compound described hereinabove.

A presently disclosed composition can be formulated as a pharmaceutical composition, which comprises a presently disclosed compound and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^1$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

One skilled in the art will appreciate that the particular formulation will depend, in part, upon the particular agent that is employed, and the chosen route of administration. Accordingly, there is a wide variety of suitable formulations of compositions of the presently disclosed subject matter.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a presently disclosed composition, administered to an animal, particularly a human, in the context of the presently disclosed subject matter should be sufficient to produce at least a detectable amount of a diagnostic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier also can contain stabilizers, preservatives, antioxidants, or other additives, which are well known to one of skill in the art, or other vehicles as known in the art.

iv. General Definitions

Although specific terms are employed herein, they are used in a generic and descriptive sense only and not for purposes of limitation. Particular definitions are provided herein for clarity. Unless otherwise defined, all technical and scientific terms used herein have the same meaning as commonly understood by one of ordinary skill in the art to which this presently described subject matter belongs.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells.

By "control" is meant a standard or reference condition.

By "disease" is meant any condition or disorder that damages or interferes with the normal function of a cell, tissue, organ, organism, or subject.

The term "administering" as used herein refers to contacting a subject with a presently disclosed agent.

By "delivery device" is meant any device that provides for the release of an imaging agent. Exemplary delivery devices include tablets and pills, described below, as well as syringes, osmotic pumps, indwelling catheters, delayed-release and sustained-release biomaterials.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments 50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis and Evaluation of Carbamate-Based Agents for Imaging of PSMA and Cancer Radiotherapy Material and Methods
General Procedures.

Solvents and chemicals purchased from commercial sources were of analytical grade or better and used without further purification. Tert-butyl-1,3-diisopropylisourea, L-glutamic acid di-tert-butyl ester, $N^\varepsilon$-Boc-lysine-tert-butyl ester hydrochloride, 1-hydroxybenzotriazole monohydrate and 2-(1H-benzotriazole-1-yl)-1,1,3,3-tetramethyluronium hexafluorophosphate (HBTU) were purchased from Chem Impex International Inc. (Wooddale, IL). 1,1'-Carbonyl-diimidazole, iodomethane, N-hydroxysuccinimide, (diacetoxyiodo)benzene, triethylsilane ($Et_3SiH$), diisopropylethylamine (DIEA) and triethylamine (TEA) were purchased from Sigma-Aldrich (St. Louis, MO). 4-bromo-2-nitro-benzaldehyde was purchased from Combi-Block (San Diego, CA). (S)-6-((tert-butoxycarbonyl)amino)-2-hydroxyhexanoic acid (Makarasen, 2009) 4-iodo-2-nitro-benzaldehyde (Litosh, 2009) and (S)-dimethyl 2-hydroxypentanedioate (Winkler, 2013) were synthesized by previously reported procedures. Analytical thin-layer chromatography (TLC) was performed using Aldrich aluminum-backed 0.2 mm silica gel Z19, 329-1 plates and visualized by ultraviolet light (254 nm), $I_2$ and 1% ninhydrin in EtOH. Flash chromatography was performed using silica gel (MP SiliTech 32-63 D 60 Å) purchased from Bodman (Aston, PA). All in vitro PSMA binding studies were performed in triplicate. $^1$H NMR spectra were recorded on a Bruker Ultrashield™ 400 MHz or 500 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. High resolution mass spectra were obtained at the University of Notre Dame Mass Spectrometry & Proteomics Facility, Notre Dame, IN, using ESI either by direct infusion on a Bruker microTOF-II or by LC elution via an ultra-high pressure Dionex RSLC with C18 column coupled to a Bruker microTOF-Q II. HPLC purification was performed using a Phenomenex C18 Luna 10×250 mm$^2$ column on Agilent Technologies 1260 Infinity Preparative HPLC System. HPLC purification of [$^{18}$F] labeled compounds were performed on a Varian Prostar System (Palo Alto, CA), equipped with a Varian ProStar 325 UV-Vis variable wavelength detector and a Bioscan Flow-count in-line Radioactivity detector, all controlled by Galaxie software. The specific radioactivity was calculated as the ratio of the radioactivity eluting at the retention time of product during the preparative HPLC purification to the mass corresponding to the area under the curve of the UV absorption.

Synthesis and Characterization of Carbamates.

(S)-6-((tert-butoxycarbonyl)amino)-2-hydroxyhexanoic acid 14

(S)-6-amino-2-hydroxyhexanoic acid 200 mg (1.36 mmol) and $K_2CO_3$ 550 mg (4 mmol) were dissolved in 10 mL of water. Di-tert-butyl dicarbonate (300 mg, 1.36 mmol) was added to the solution. The reaction was stirred at room temperature overnight. After acidified to pH 2 by concentrated HCl, the aqueous layer was extracted by methylene chloride and the organic layer was dried with sodium sulfate. 250 mg (S)-6-((tert-butoxycarbonyl)amino)-2-hydroxyhexanoic acid was obtained, after the organic solvent was removed under vacuum. The yield was 74%.

(S)-tert-butyl 6-((tert-butoxycarbonyl)amino)-2-hydroxyhexanoate 15

(S)-6-((tert-butoxycarbonyl)amino)-2-hydroxyhexanoic acid 14 (250 mg, 1.00 mmol) was mixed with tert-butyl-1,3-diisopropylisourea (600 mg, 3.00 mmol) in 2 mL anhydrous methylene chloride. The reaction was sealed and kept at room temperature for 36 h. 135 mg (S)-tert-butyl 6-((tert-butoxycarbonyl)amino)-2-hydroxyhexanoate was obtained after flash column chromatography and the yield was 44%. ($^1$H NMR (400 MHz, CDCl$_3$): δ 4.56 (br, 1H), 4.06 (dd, J1=7.2 Hz, J2=4.4 Hz, 1H), 3.14 (m, 2H), 2.25 (br, 1H), 1.83-1.75 (m, 1H), 1.65-1.35 (m, 23H); $^{13}$C NMR (125 MHz, CDCl$_3$): δ 174.6, 156.1, 82.5, 79.2, 70.4, 40.6, 34.0, 29.8, 28.5, 28.1, 22.0. MS: Calculated for [C$_{15}$H$_{30}$NO]$^+$, 304.2118 [M+H]$^+$; Found 304.2147.

(S)-1-(tert-butoxy)-6-((tert-butoxycarbonyl)amino)-1-oxohexan-2-yl 1H-imidazole 1-carboxylate 16

(S)-tert-butyl 6-((tert-butoxycarbonyl)amino)-2-hydroxyhexanoate 15 (131 mg, 0.43 mmol) and 1,1'-carbonyldiimidazole (105 mg, 0.65 mmol) were mixed in 5 mL anhydrous methylene chloride. The reaction was kept at room temperature for 1 h. 113 mg (S)-1-(tert-butoxy)-6-((tert-butoxycarbonyl)amino)-1-oxohexan-2-yl 1H-imidazole-1-carboxylate was obtained by flash column chromatography and the yield was 81%. ($^1$H NMR (400 MHz, CDCl$_3$): δ 8.19 (s, 1H), 7.50 (s, 1H), 7.18 (s, 1H), 5.14 (m, 1H), 4.61 (br, 1H), 3.21-3.16 (m, 2H), 2.05-1.96 (m, 2H), 1.60-1.42 (m, 22H); $^{13}$C NMR (125 MHz, CDCl$_3$): δ 167.8, 156.0, 148.3, 137.2, 130.9, 117.2, 83.3, 79.3, 75.8, 40.2, 30.6, 29.7, 28.4, 28.0, 22.4. MS: Calculated for [C$_{19}$H$_{32}$N$_3$O$_6$]$^+$, 398.2286 [M+H]$^+$; Found 398.2309.

(10S,14S)-tri-tert-butyl 2,2-dimethyl-4,12-dioxo-3,11-dioxa-5,13-diazahexadecane-10,14,16-tricarboxylate 17

(S)-1-(tert-butoxy)-6-((tert-butoxycarbonyl)amino)-1-oxohexan-2-yl 1H-imidazole-1-carboxylate 16 (139 mg, 0.35 mmol) and L-glutamic acid di-tert-butyl ester (170 mg, 0.66 mmol) were mixed neat. The reaction was kept at 45° C. for 2 days. (10S,14S)-tri-tert-butyl 2,2-dimethyl-4,12-dioxo-3,11-dioxa-5,13-diazahexadecane-10,14,16-tricarboxylate was obtained 210 mg by flash column chromatography and the yield was 100%. $^1$H NMR (400 MHz, CDCl$_3$): δ 5.5 (br, 1H), 4.88-4.70 (m, 1H), 4.59 (br, 1H), 4.32-4.23 (m, 1H), 3.16-3.08 (m, 2H), 2.45-2.28 (m, 2H), 2.25-2.10 (m, 1H), 1.95-1.76 (m, 3H), 1.60-1.42 (m, 22H). $^{13}$C NMR (125 MHz, CDCl$_3$) δ 172.1, 171.1, 169.9, 156.0, 155.4, 82.4, 81.9, 80.6, 79.1, 73.1, 53.8, 40.4, 31.4, 30.9, 29.6, 28.4, 28.1, 28.0, 22.4. MS: Calculated for [C$_{29}$H$_{52}$N$_2$NaO$_{10}$]$^+$, 611.3514 [M+Na]$^+$; Found 611.3502.

(S)-2-(((((S)-5-amino-1-carboxypentyl)oxy)carbonyl)amino) Pentanedioic Acid Trifluoroacetic Acid Salt, 18

(10S,14S)-tri-tert-butyl 2,2-dimethyl-4,12-dioxo-3,11-dioxa-5,13-diazahexadecane-10,14,16-tricarboxylate (17) (237 mg) was treated with a 6 mL solution of TFA/methylene chloride(1/1) for 2 h. The final product was purified by HPLC giving 90 mg, yield 70%. $^1$H NMR (400 MHz, D$_2$O/CD$_3$CN 1:1): δ 4.80 (m, 1H), 4.20-4.11 (m, 1H, two isomers), 2.90 (t, J=6.8 Hz, 2H), 2.43 (t, J=6.8 Hz, 2H), 2.16-2.09 (m, 1H), 1.91-1.83 (m, 3H), 1.61-1.58 (m, 2H), 1.43-1.37 (m, 2H). $^{13}$C NMR (125 MHz, D$_2$O/CD$_3$CN 1:1) δ 177.1, 175.7/175.5 (two isomers), 163.1/162.8 (two isomers), 157.3, 73.4, 53.4, 39.2, 36.5, 30.0, 26.2, 26.0, 21.4. MS: Calculated for [C$_{12}$H$_{21}$N$_2$O$_8$]$^+$, 321.1292 [M+H]$^+$; Found 321.1310. HPLC (10×250 mm Phenomenix Luna C18 column, mobile phase 100/0/0.1% water/acetonitrile/TFA, flow 10 mL/min). 18 eluted at 14.5 min.

(S)-2-(((((S)-1-carboxy-5-(4-fluorobenzamido)pentyl)oxy) carbonyl)amino)pentanedioic Acid 12 (XY-20)

As outlined in scheme 1 (S)-2-(((((S)-5-amino-1-carboxypentyl)oxy)carbonyl)amino) pentanedioic acid TFA salt 18 (10 mg, 0.024 mmol) was dissolved in 1 mL DMSO and 20 μL triethylamine. To the solution, N-succinimidyl 4-fluorobenzoate (11.5 mg, 0.045 mmol) was added. The resulting solution was kept at room temperature for 2 hours. After the solvent was removed under vacuum and HPLC purification, 12 (XY-20) (8 mg) was obtained. Yield is 75%. HPLC (10×250 mm Phenomenix Luna C18 column, mobile phase 75/25/0.1% water/acetonitrile/TFA, flow 4 mL/min). 12 (XY-20) eluted at 12 min. ¹H NMR (400 MHz, D₂O/CD₃CN 1:1): δ 8.11 (m, 2H), 7.51 (t, J=8.8 Hz, 2H), 5.16 (m, 1H), 4.52-4.45 (m, 1H, two rotamers), 3.64 (t, J=7.2 Hz, 2H), 2.74 (t, J=7.2 Hz, 2H), 2.46-2.41 (m, 1H), 2.22-2.12 (m, 3H), 1.91-1.80 (m, 2H), 1.77-1.68 (m, 2H). ¹³C NMR (125 MHz, D₂O/CD₃CN 1:1): δ 176.3, 174.8, 174.2, 168.4, 166.0/164.0 (coupled with F), 156.9, 130.9, 130.2/130.1 (coupled with F), 116.0/115.9 (coupled with F), 73.2, 53.6, 39.9, 30.9, 30.3, 28.7, 26.7, 22.5. MS: Calculated for $[C_{19}H_{23}FN_2NaO_9]^+$, 465.1280 $[M+Na]^+$; Found 465.1295.

Scheme 1.

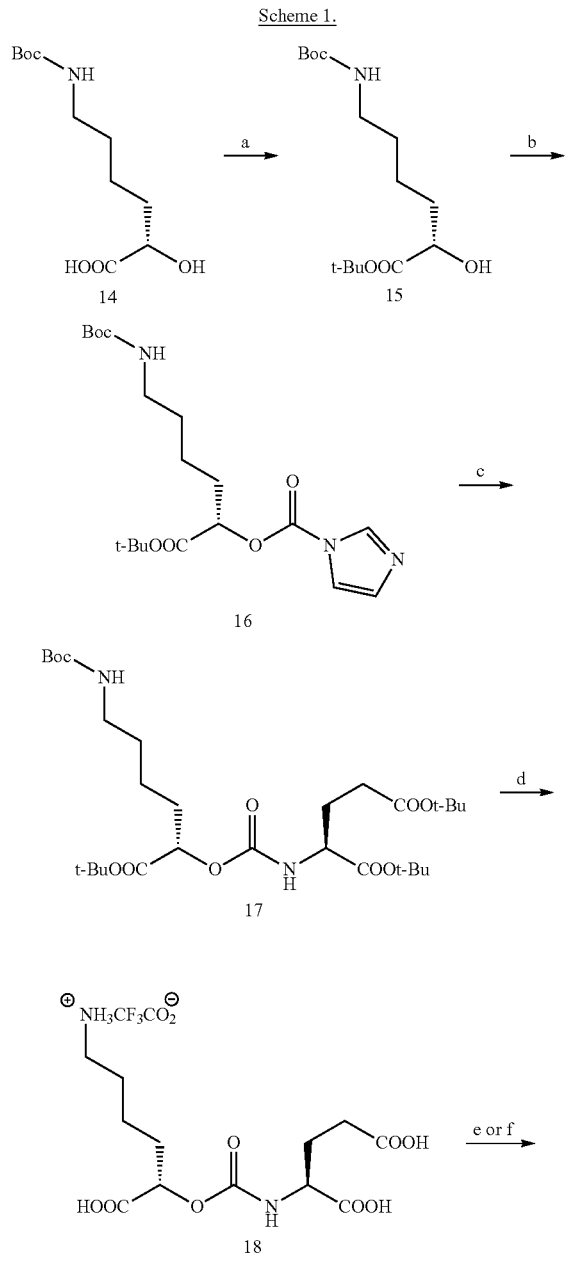

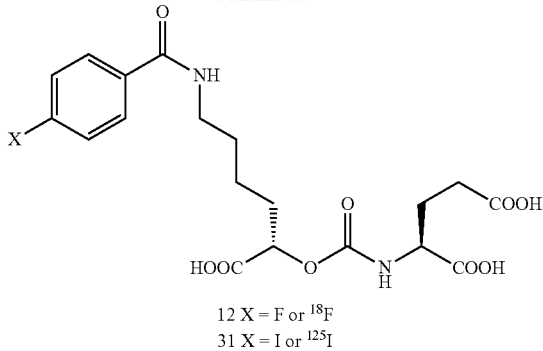

12 X = F or ¹⁸F
31 X = I or ¹²⁵I (a) t-butyl-1,3-diisopropylisourea, CH₂Cl₂, rt, 3 d, (b) carbonyldiimidazole, CH₂Cl₂, rt, 1 h, (c) L-glutamic acid di-tert-butyl ester, neat, 45° C., 2 d, (d) TFA/CH₂Cl₂(1/1), rt, 2 h, (e) N-succinimidyl-4-fluorobenzoate or N-succinimidyl-4-[¹⁸F]fluorobenzoate, Et₃N, DMSO, rt, 2 h; (f) N-succinimidyl-4-iodobenzoate or N-succinimidyl-4-[¹²⁵I]iodobenzoate, diisopropylethyl amine, DMSO rt 1 h.

General Procedure for the PSMA Binding Carbamates.

The key intermediate 18 was treated with 1.5 eq of carboxylic acid NHS ester and 6 eq of triethylamine in DMSO for 2 h at room temperature. The final product was purified by HPLC.

NMR and MS for carbamates (structures and PSMA binding are given in Example 3).

XY-10: ¹H NMR (400 MHz, D₂O/CD₃CN 1:1): δ 4.81 (dd, J1=9.2 Hz, J2=8.0 Hz, 1H), 4.21-4.11 (m, 1H, two rotamers), 2.42 (t, J=7.6 Hz, 2H), 2.15-2.06 (m, 1H), 1.94-1.82 (m, 1H), 1.72-1.51 (m, 3H), 0.83-0.80 (m, 6H). MS: 306 $(M+H^+)$.

XY-16: ¹H NMR (400 MHz, D₂O/CD₃CN 1:1): δ 8.20 (m, 2H), 7.58 (m, 2H), 5.32-5.28 (m, 1H), 4.65-2.52 (m, 1H, two rotamers), 3.92-3.75 (m, 2H), 2.82 (t, J=7.6 Hz, 2H), 2.58-2.28 (m, 4H). MS: 415 $(M+H^+)$.

XY-17: ¹H NMR (400 MHz, D₂O/CD₃CN 1:1): δ8.23 (dd, J1=8.8 Hz, J2=5.6 Hz, 2H), 7.63 (t, J=8.8 Hz, 2H), 5.34 (dd, J1=8.8 Hz, J2=4.0 Hz, 1H), 4.65-2.56 (m, 1H, two rotamers), 3.90 (t, J=6.4 Hz, 2H), 2.82 (t, J=7.2 Hz, 2H), 2.58-2.28 (m, 4H). MS: 415 $(M+H^+)$.

XY-21: ¹H NMR (400 MHz, D₂O/CD₃CN 1:1): δ 8.84 (s, 1H), 8.55-8.32 (m, 4H), 8.15-8.04 (m, 2H), 5.36 (m, 1H), 4.52-4.45 (m, 1H, two rotamers), 3.90 (t, J=7.2 Hz, 2H), 2.94 (t, J=7.2 Hz, 2H), 2.66-2.51 (m, 1H), 2.42-2.32 (m, 3H), 2.19-2.10 (m, 2H), 2.07-1.98 (m, 2H). MS: 475 (M+H+).

XY-22: ¹H NMR (400 MHz, D₂O/CD₃CN 1:1): δ 8.77 (s, 1H), 8.41-8.29 (m, 3H), 7.82 (s, 1H), 7.71 (d, J=8.8 Hz, 1H), 5.36 (m, 1H), 4.65-4.63 (m, 1H, two rotamers), 4.41 (s, 3H), 3.88 (t, J=7.2 Hz, 2H), 2.90 (t, J=7.2 Hz, 2H), 2.63-2.58 (m, 1H), 2.40-2.32 (m, 3H), 2.15-2.12 (m, 2H), 2.03-2.00 (m, 2H). MS: 505 $(M+H^+)$.

XY-23: MS: 531 $(M+H^+)$.

XY-24: ¹H NMR (400 MHz, D₂O/CD₃CN 1:1): δ 8.27 (d, J=8.4 Hz, 2H), 8.15-8.09 (m, 3H), 7.51 (d, J=6.0 Hz, 1H), 5.29-5.14 (m, 3H), 4.77-4.74 (m, 1H), 4.58-4.50 (m, 1H), 3.80 (t, J=7.2 Hz, 2H), 2.86 (t, J=7.2 Hz, 2H), 2.45-2.41 (m, 1H), 2.33-2.29 (m, 3H), 2.06-2.00 (m, 2H), 1.93-1.80 (m, 2H). MS: 563 $(M+H^+)$.

XY-26: MS: 551 $(M+H^+)$.
XY-27: MS: 455 $(M+H^+)$.
XY-28: MS: 471 $(M+H^+)$.
XY-29: MS: 482 $(M+H^+)$.
XY-30: MS: 482 $(M+H^+)$.
XY-38: MS: 503 $(M+H^+)$.

XY-39: MS: 565 (M+H$^+$).
XY-42: MS: 519 (M+H$^+$).
XY-43: MS: 569 (M+H$^+$).
XY-49: MS: 477 (M+H$^+$).
XY-50: MS: 868 (M+H$^+$).

NAALADase Assay.

The PSMA inhibitory activity was determined using a modification of the fluorescence-based Amplex Red Glutamic Acid Assay (Life Technologies, Grand Island, NY) (Kozikowski, 2004). Briefly, lysates of LNCaP cell extracts (25 µL) were incubated with the inhibitor (12.5 µL) in the presence of 4 µM N-acetylaspartylglutamate (NAAG) (12.5 µL) for 120 min. The amount of the glutamate released by NAAG hydrolysis was measured by incubating with a working solution (50 µL) of the Amplex Red Glutamic Acid Kit for 60 min. Fluorescence was measured with a VICTOR3V multilabel plate reader (Perkin Elmer Inc., Waltham, MA) with excitation at 490 nm and emission at 642 nm. Inhibition curves were determined using semi-log plots and IC50 values were determined at the concentration at which enzyme activity was inhibited by 50%. Enzyme inhibitory constants (Ki values) were generated using the Cheng-Prusoff conversion (Cheng, 1973). Assays were performed in triplicate. Data analysis was performed using GraphPad Prism version 4.00 for Windows (GraphPad Software, San Diego, California).

Cell Lines and Mouse Models.

Sublines of the androgen-independent PC3 human prostate cancer cell line, originally derived from an advanced androgen independent bone metastasis, were used. These sublines have been modified to express high (PC3 PIP) or possess low (PC3 flu) levels of PSMA, and were generously provided by Dr. Warren Heston (Cleveland Clinic). PSMA-expressing (PC3 PIP), non-expressing (PC3 flu) PCa cell lines, were grown in RPMI 1640 medium (Corning Cellgro, Manassas, VA) containing 10% fetal bovine serum (FBS) (Sigma-Aldrich, St. Louis, MO) and 1% Penicillin-Streptomycin (Corning Cellgro, Manassas, VA). PC-3 PIP cells were grown under 20 µg/mL of puromycin selection in the growth medium to maintain PSMA expression. All cell cultures were maintained in an atmosphere containing 5% carbon dioxide ($CO_2$), at 37.0° C. in a humidified incubator. Animal studies were carried out in full compliance with the regulations of the Johns Hopkins Animal Care and Use Committee. Six- to eight-week-old male, non-obese diabetic (NOD)/severe-combined immunodeficient (SCID) mice (Johns Hopkins Immune Compromised Core) were implanted subcutaneously (sc) with PC3 PIP (PSMA+) and PC3 flu (PSMA-) cells (1×106 in 100 µL of HBSS (Corning Cellgro, Manassas, VA) at the forward right and left flanks, respectively. Mice were imaged or used in ex vivo biodistribution assays when the xenografts reached 5 to 7 mm in diameter.

Radiosynthesis.

(S)-2-((((S)-1-carboxy-5-(4-[$^{18}$F]fluorobenzamido) pentyl)oxy)carbonyl)amino)pentanedioic acid [$^{18}$F] 12 ([$^{18}$F]XY-20)

[$^{18}$F]SFB was prepared according to a literature procedure (J. Label. Comp. Radiopharm, 2008, 51, 68-71). A methylene chloride solution of [$^{18}$F]SFB was evaporated under a stream of argon gas. To this residue was added 3 mg of (S)-2-((((S)-5-amino-1-carboxypentyl)oxy)carbonyl) amino)-pentanedioic acid 18 in 200 µL dry DMF and 5 µL triethylamine. This was heated for 10 min at 50° C., cooled to room temperature, acidified with trifluoroacetic acid, diluted with water, and injected onto a radio-HPLC (10×250 mm Phenomenix Luna C18 column, mobile phase 75/25/0.1% water/acetonitrile/TFA, flow 4 mL/min). 12 (XY-20) eluted at 12 min. The product HPLC fraction was collected, neutralized with sodium bicarbonate, concentrated under vacuum, and dissolved in sterile saline for injection.

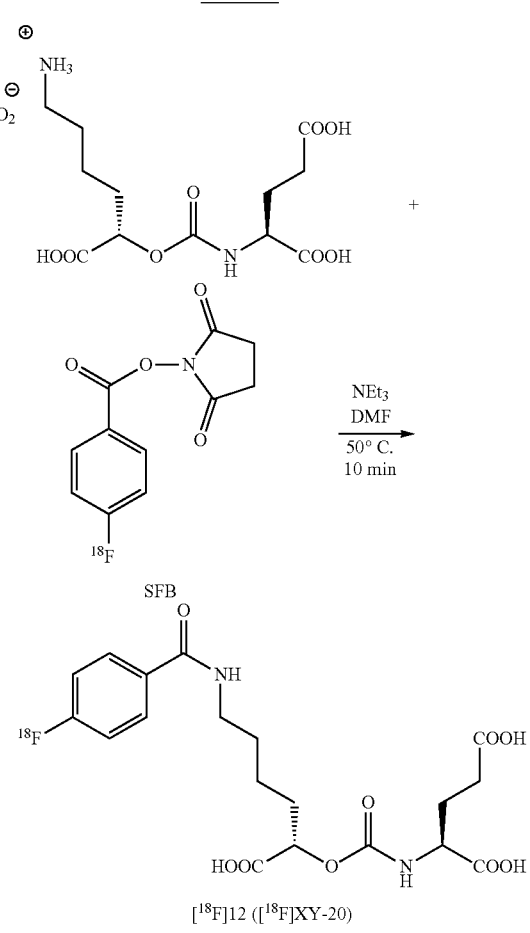

Scheme 2.

12/7 27% from SFB, SA = 3900 Ci/mmol
12/14 28% from SFB, SA = 2900 Ci/mmol (S)-2-(((((S)-1-carboxy-5-(4-[$^{125}$I]iodobenzamido) pentyl)oxy)carbonyl)amino) Pentanedioic Acid [$^{18}$F]31 ([$^{18}$F]XY-26)

N-succinimidyl-4-[$^{125}$I]iodobenzoate was prepared by a modification of the method of Dekker et al. (Dekker et al., 2005). In particular, to a solution of 0.1 mg N-succinimidyl-4-tributylstannylbenzoate (Dekker et al., 2005) in 100 µL methanol was added 2 µL glacial acetic acid, 7.3 mCi of Na[$^{125}$I] (Perkin Elmer, Billerica, MA), and 5 µL of solution of N-chlorosuccinimide in methanol (10 mg N-chlorosuccinide in 1.5 mL methanol). This was allowed to stand at room temperature for 20 min, then diluted with 200 µL methanol and injected onto a semi-preparative-HPLC (10× 250 mm, 10 micron, Phenomenex Luna C18 column, 55/45/0.1 water/acetonitrile/trifluoroacetic acid, flow=4 mL/m). N-succinimidyl-4-[$^{125}$I]iodobenzoate eluted at 14 min. This was diluted with 20 mL water, loaded onto an activated Waters C18 Sep-Pak Plus cartridge, washed with 10 mL water, dried with a stream of nitrogen for 2 min, then eluted with 2 mL methylene chloride through a $Na_2SO_4$ drying cartridge. The methylene chloride solution of N-succinimidyl-4-[$^{125}$I]iodobenzoate (5.9 mCi) was stored at 0-2° C. The methylene chloride solution was then evaporated to dryness under a stream of nitrogen and to this was added a solution of 18 (2 mg/200 μL DMSO). To this solution is added 5 μL diisopropylethylamine. Reaction is shaken and allowed to stand at room temperature for one hour. The reaction is then acidified by the addition of 20 μL TFA and diluted with 1 mL water. This is injected onto a semi-preparative-HPLC (10×250 mm, 10 micron, Phenomenex Luna C18 column, 72/28/0.1 water/acetonitrile/trifluoroacetic acid, flow=4 mL/m). Retention times of [$^{125}$I]31 was 12 min. Product fraction was diluted with 40 mL water, loaded onto an activated Waters C18 Sep-Pak Plus cartridge, washed with 10 mL water, dried with a stream of nitrogen for 2 min, then eluted with 2 mL ethanol. Ethanol solution was concentrated under a stream of nitrogen until dryness and reconstituted in buffer for in-vitro assay. Starting with 2.0 mCi and 2.2 mCi of N-succinimidyl-4-[$^{125}$I]iodobenzoate, 1.8 and 2.0 mCi of [$^{125}$I]31 was prepared.

Scheme 3.

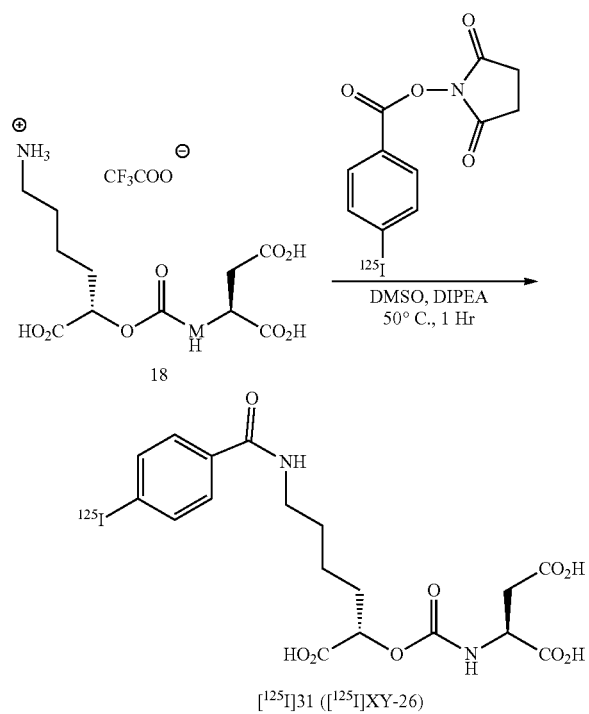

Imaging study. Dynamic and whole-body PET and CT images were acquired on an eXplore VISTA small-animal PET (GE Healthcare) and an X-SPECT small SPECT/CT system (Gamma Medica Ideas), respectively. For imaging studies, anesthesia was induced with 3% and maintained under 1.5% isoflurane (v/v) in oxygen. PET or PET-CT imaging studies were performed on NOD/SCID mice bearing PSMA+PC-3 PIP and PSMA-PC-3 flu tumors. Following intravenous injection of [$^{18}$F]12 ([$^{18}$F]XY-20) PET images were acquired at 10 min, 30 min, 1 h, 2 h and 4 h p.i. as a pseudodynamic scan, i.e., a sequence of successive whole-body images were acquired in two bed positions. The dwell time at each bed position was 10 min for a total scan time of 20 minutes. An energy window of 250-700 keV was used. Images were reconstructed using the FORE/2D-OSEM method (one iteration, 16 subsets) and included correction for radioactive decay, scanner dead time, and scattered radiation.

Biodistribution.

Mice bearing PSMA+PC-3 PIP and PSMA-PC-3 flu xenografts Chang et al., 1999) were injected via the tail vein with 740 kBq (20 μCi) of [$^{18}$F]12 ([$^{18}$F]XY-20) in 200 μL of saline. At various time points post-injection, mice were sacrificed by cervical dislocation and the blood immediately collected by cardiac puncture. The heart, lungs, liver, stomach, pancreas, spleen, fat, kidney, muscle, small and large intestines, urinary bladder, PSMA+PC-3 PIP and PSMA-PC-3 flu tumors were collected. Each organ was weighed, and the tissue radioactivity was measured with an automated gamma counter (1282 Compugamma—CS, Pharmacia/LKBNuclear, Inc., Mt. Waverly, Vic. Australia). The % ID/g was calculated by comparison with samples of a dilution of a standard dose. All measurements were corrected for decay. Data are expressed as mean standard deviation (SD).

Molecular Modeling.

All molecular modeling experiments were performed using Discovery Studio 4.0 developed by Accelrys, Inc. (San Diego, CA).

Protein and Ligand Structure Preparation. The X-ray structure of PSMA co-crystallized with the competitive inhibitor DCIBzL (PDB: 3D7H) was downloaded from the protein data bank (RCSB, http://www.rcsb.org/pdb/home/home.do). The water molecules were removed while the co-crystallized ligand was used as a template to sketch the compounds using the Sketch Molecules module in Discovery Studio.

In Situ Ligand Minimization.

Each ligand was minimized while binding to its target protein using the in situ ligand minimization module with the following parameters: CHARMmas an input force field, minimization algorithm as smart minimizer, maximum minimization steps equal to 1000, minimization with RMS gradient equal to 0.001 Å, and minimization energy change set equal to zero. After the minimization protocol was executed, the in situ minimized ligands were stripped of their nonpolar hydrogens to simplify the overall view. The protein was depicted in the form of a light gray line ribbon. The bound ligand is depicted as a stick with atoms color-coded according to element: carbon (gray), nitrogen (blue), and oxygen (red) (FIG. 13).

In Vitro Stability Studies.

PC-3 PIP (PSMA+) and PC-3 flu (PSMA−) cells were cultured as previously described (Banerjee et al., 2014). 300,000 PIP or flu cells were seeded into three wells each of a 6 well plate using RPMI 1640+10% fetal bovine serum+1% Penicillin-Streptomycin (Corning Cellgro, Manassas, VA) and were grown to 80% confluency. At the time of assay, the culture medium was refreshed and 50 μCi (1.35 kBq) of [$^{125}$I]31 ([$^{125}$I]XY-26) or [$^{125}$I]32 ([$^{125}$I]XY-57) was added to both a PIP- and flu-containing well. After radiotracer addition, the plate was returned to the incubator (humidified 37° C., 5% $CO_2$) for 30 minutes. The medium was then carefully removed and saved for counting in a LKB Wallac 1282 Compugamma gamma counter (Mount Waverly, Vic, Australia). The cells were washed twice with ambient temperature PBS, pH 7.4 followed by the addition of dd$H_2O$ to lyse the cells. Lysis took place over 30 minutes inside the incubator. The lysates were then collected and counted using the gamma counter. Equal amounts of radioactivity from the supernatant and lysates were spotted onto silica gel 60 RP-18 F254S glass TLC plates (EMD Millipore Corp., Billerica, MA) and the plates were developed using a mobile phase consisting of 55% acetonitrile, 45% water and 0.1% trifluoroacetic acid. The TLC plate was dried and exposed to Kodak Biomax x-ray film (Fisher Scientific) prior to digitizing using the MCID Core package (Interfocus Imaging, Cambridge, UK). Standards solutions of [$^{125}$I]31 ([$^{125}$I]XY-26) and [$^{125}$I]32 ([$^{125}$I]XY-57) had Rf values of 0.8. Intracellular and extracellular metabolites of [$^{125}$I]31 ([$^{125}$I]XY-26) in PC-3 PIP cells had an Rf value of approximately 0.44.

Results

Chemistry.

Among the potent urea-based PSMA binding ligands, 4-fluorobenzoyl- and 4-iodobenzoyl-lys-glu urea, compounds 9 (YC-I-26) and 10 (YC-I-27) respectively, have produced some of the highest affinities reported (FIG. 2A and FIG. 2B) (Chen, 2008). Based on these ureas, NPA-carbamate 12 (XY-20) (Scheme 1) was the initial target compound. It has been reasoned that the 4-fluorobenzoyl side-chain would provide high affinity and specificity by utilizing the S1 binding pocket and be amenable to radiolabeling with $^{18}$F. The synthesis of 12 (XY-20) started with N-Boc protected (S)-6-amino-2-hydroxyhexanoic acid 14 (Scheme 1). The carboxylic acid as the tert-butyl ester was first protected and then converted alcohol 15 to N-imidazolecarbamate 16. Compound 16 reacted slowly with L-glutamic acid di-tert-butyl ester under neat conditions and provided a quantitative yield of 17. Upon deprotection intermediate 18 was obtained in 70% yield as a trifluoroacetate salt. NPA-carbamate 12 (XY-20) was obtained by treating 18 with N-succinimidyl-4-fluorobenzoate in the presence of triethylamine.

X-ray co-crystal studies with bound urea-based ligands such as 10 have demonstrated a unique cation-π interaction with PSMA, with the benzoyl group of the ligand fully inserted into the "arginine patch" of the PSMA S binding pocket and an adjacent hydrophobic subpocket that can accommodate the para-iodo substituent of 10 (Barinka, 2008). That additional interaction likely accounted for the increase in binding affinity of 10 compared to 9 (Chen, 2008; Barinka, 2008). To increase the binding affinities of the iodinated carbamates 31 has been prepared by reacting N-succinimidyl-4-iodobenzoate with 18, respectively (Scheme 1). For PET imaging with $^{18}$F, the 4-iodo-benzoyl group would require an [$^{18}$F]fluoro substituent in the activated ortho position.

In-Vitro PSMA Binding.

The PSMA inhibitory activities of the prepared compounds were measured using a modification of the fluorescence-based Amplex Red Glutamic Acid assay (Kozikowski, 2004) (FIG. 2B). Carbamates 12 (XY-20) and reversed carbamate 13 (XY-48) inhibited PSMA at $K_i$=42 nM and 9.2 nM, respectively, significantly less potent than the corresponding ureido analog 9 (XY-I-26), ($K_i$=0.25 nM) (Chen, 2008). Carbamate 31 (XY-26) and reversed carbamate 32 (XY-57) inhibited PSMA at $K_i$=0.9 nM and 0.04 nM, respectively. Reversed carbamates 23 (XY-52) and 24 (XY-47) demonstrated potent inhibition of PSMA, with $K_i$=0.11 nM and 0.21 nM, respectively, while the corresponding ureas 26 (XY-58) and 27 (XY-44) inhibited PSMA with $K_i$=0.04 and 0.02 nM, respectively.

PSMA Inhibitor Docking Studies.

Figure 7A:
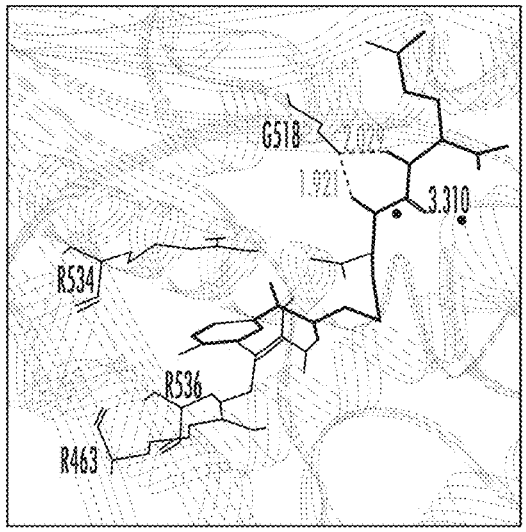
Figure 7B:
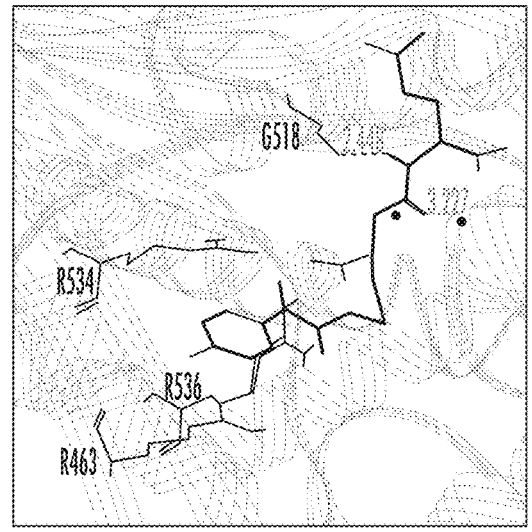
Figure 7C:
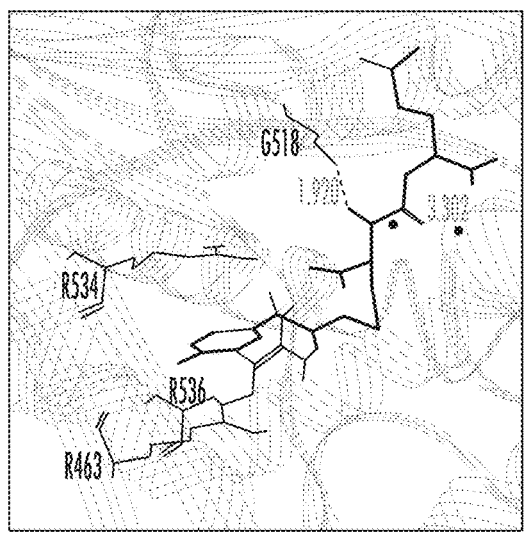
Figure 7D:
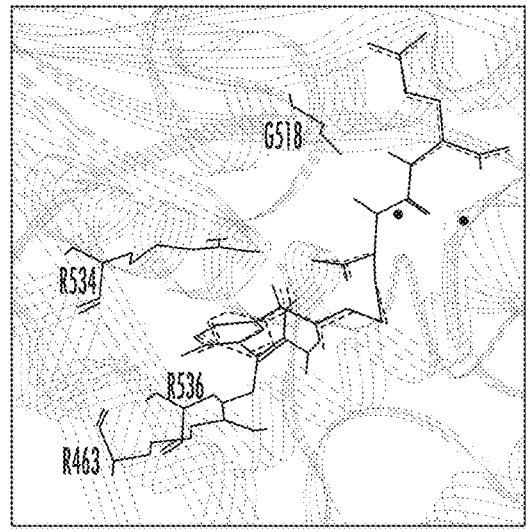

Urea 9 (XY-I-26), NPA-carbamate 12 (XY-20) and OPA-reversed carbamate 13 (XY-48) were subjected to in situ ligand minimization docking experiments based on the reported X-ray crystal structure of PSMA known as 3D7H. (Barinka, 2008). The results are shown in FIG. 7A, FIG. 7B, FIG. 7C, and FIG. 7D. The urea N—H in 9 (YC-I-26) binds to the carbonyl oxygen of G518 asymmetrically, with the Lys-N—H (1.92 Å) slightly closer to the carbonyl oxygen than Glu-N—H (2.03 Å). Lys-OPA reversed carbamate 13 (XY-48), with the Glu-N—H changed to O resulting in the loss of a hydrogen bond, retained nearly all of the features of 9 (YC-I-26), when binding to PSMA (FIG. 7C), and the Lys-N—H distance to G518 slightly increased 1.95 Å, with the carbamate shifting slightly towards the zinc (FIG. 7C vs. FIG. 7A). This resulted in a 30-fold reduction in binding affinity compared to 9 (YC-I-26). NPA carbamate 12 (XY-20), with the Lys-N—H changed to 0, altered the binding mode dramatically (FIG. 7B), with the carbamate shifting toward the zinc resulting an increase in hydrogen bond distance to G518 (2.448 Å) (FIG. 7B). This decreased the binding affinity of 12 (XY-20) by more than 150-fold compared to 9 (YC-I-26).

Radiochemistry.

Carbamate [$^{18}$F]12 ([$^{18}$F]XY-20) was prepared by reacting N-succinimidyl-4-[$^{18}$F]fluorobenzoate (Tang, 2008), [$^{18}$F]SFB, with 18 respectively (Scheme 2). $^{125}$I labeled analog $^{125}$I31 ($^{125}$I XY-26) (Scheme 3) was prepared likewise using N-succinimidyl-4-[$^{125}$I]iodobenzoate (Zalutsky, 1987).

Biodistribution and Imaging.

Whole body micro-PET CT images of [$^{18}$F]12 ([$^{18}$F]XY-20) are shown in FIG. 8A, FIG. 8B, FIG. 8C, and FIG. 8D and its biodistribution is shown in Table 1. [$^{18}$F]12 ([$^{18}$F]XY-20) exhibited a modest PC-3 PIP tumor uptake of 6.33±1.55% injected dose/g (% ID/g) at 30 min and radioactivity rapidly cleared from all organs including PC-3 PIP tumor. PET-CT imaging confirms both the rapid tumor uptake and clearance from all tissues. In the PET-CT imaging, co-injection of [$^{18}$F]12 ([$^{18}$F]XY-20) with an excess of known competing inhibitor (S)-2-(3-((S)-1-carboxy-3-methylbutyl)ureido)pentanedioic acid (ZJ-43), showed complete blockade of tumor uptake indicating that the tumor uptake is PSMA specific (FIG. 8A, FIG. 8B, FIG. 8C, and FIG. 8D).

TABLE 1

Biodistribution of [$^{18}$F]12 ([$^{18}$F](XY-20)

| | 30 min[b] | 60 min[c] | 90 min[c] | 180 min[c] |
| --- | --- | --- | --- | --- |
| blood | 2.51 ± 1.75 | 1.07 ± 0.26 | 0.20 ± 0.14 | 0.08 ± 0.06 |
| heart | 1.12 ± 0.74 | 0.25 ± 0.08 | 0.11 ± 0.02 | 0.07 ± 0.04 |
| lung | 2.07 ± 1.51 | 0.85 ± 0.55 | 0.33 ± 0.05 | 0.14 ± 0.04 |
| liver | 11.0 ± 1.77 | 12.5 ± 3.01 | 11.0 ± 0.87 | 4.62 ± 3.80 |
| spleen | 3.76 ± 6.48 | 0.45 ± 0.31 | 0.27 ± 0.04 | 0.13 ± 0.08 |
| fat | 1.23 ± 1.88 | 0.15 ± 0.05 | 0.11 ± 0.06 | 0.04 ± 0.02 |
| kidney | 14.2 ± 8.47 | 6.97 ± 7.02 | 1.51 ± 0.22 | 0.50 ± 0.18 |
| Sm. int. | 1.89 ± 1.58 | 0.54 ± 0.19 | 0.27 ± 0.11 | 0.08 ± 0.04 |
| Lrg int. | 3.82 ± 5.87 | 0.62 ± 0.27 | 0.18 ± 0.03 | 0.16 ± 0.05 |
| muscle | 0.86 ± 0.81 | 0.27 ± 0.12 | 0.06 ± 0.01 | 0.03 ± 0.01 |
| bone | 2.05 ± 2.39 | 0.72 ± 0.31 | 0.79 ± 0.16 | 0.63 ± 0.14 |
| bladder | 22.4 ± 22.5 | 5.50 ± 3.45 | 2.11 ± 1.21 | 2.74 ± 0.48 |
| PC-3 Pip | 6.33 ± 1.55 | 3.52 ± 1.48 | 0.94 ± 0.24 | 0.22 ± 0.07 |
| PC-3 flu | 1.89 ± 0.78 | 0.72 ± 0.12 | 0.37 ± 0.08 | 0.12  0.03 |

[a]Values expressed as percent injected dose/gram ± standard deviation;
[b]N = 7;
[c]N = 4

In-Vitro Stability Studies.

Because NPA carbamates [$^{18}$F]12 ([$^{18}$F]XY-20) and OPA reversed carbamate [$^{18}$F]13 ([$^{18}$F]XY-48) (FIG. 2A) exhibited such differing pharmacokinetics (FIG. 2B), the stability of NPA carbamate [$^{125}$I]31 ([$^{125}$I]XY-26) and OPA reversed carbamates [$^{125}$I]32 ([$^{125}$I]XY-57) in-vitro have been tested. The radioiodinated compounds were utilized for the convenience of the long half-life of I-125. Polar radiometabolite(s)

in extracellular and intracellular fluid were only seen for NPA [$^{125}$I]31 ([$^{125}$I]XY-26) in PC-3 PIP cells (FIG. 9). This suggests that NPA carbamates may be subject to PSMA specific metabolism and may be the reason for their rapid clearance from PSMA expressing tumors and organs.

Discussion

Recent clinical PET imaging using either $^{18}$F, $^{124}$I or $^{68}$Ga labeled urea based PSMA inhibitors have produced high quality PET images allowing the detection of both primary and metastatic lesions, some of which were undetectable by conventional imaging. Although all agents exhibited renal uptake, some agents (Ex: [$^{18}$F]DCFBC (Cho, 2012), and [$^{68}$Ga]DOTA-DUPA-Pep (Reske, 2013)) showed persistent blood pool occupancy but low salivary gland uptake. On the other hand, [$^{18}$F]DCFPyL (Szabo, 2015), [$^{124}$I]-MIP-1095 (Zechmann, 2014), and [$^{68}$Ga]DKFZ-11 (Afshar-Oromieh, 2012; Afshar-Oromieh, 2013) showed rapid clearance from the blood but high uptake in salivary and lacrimal glands. The latter has also been observed in radiopharmaceutical therapy studies using [$^{177}$Lu]-DKFZ-617 (Kratochwil, 2015) and [$^{131}$I]-MIP-1095 (Zechmann, 2014). Absorbed dose estimates for [$^{131}$I]-MIP-1095 identified the salivary glands, lower large intestinal wall, and kidneys as dose-limiting organs (Zechmann, 2014). Therefore, new scaffolds that would preserve the positive distribution characteristics of the urea-based agents but provide better clearance from non-target organs were sought.

However, NPA carbamate [$^{18}$F]12 ([$^{18}$F]XY-20) and OPA reversed carbamate [$^{18}$F]13 ([$^{18}$F]XY-48) exhibited drastically different pharmacokinetics: [$^{18}$F]12 ([$^{18}$F]XY-20) had modest PSMA+PC-3 PIP tumor uptake but rapidly cleared from both PC-3 PIP tumor and normal tissues including kidneys whereas OPA reversed carbamate [$^{18}$F]13 ([$^{18}$F]XY-48) had high and prolonged tumor and kidney uptake. Selective metabolism of NPA-carbamate [$^{125}$I]31 ([$^{125}$I]XY-26) was observed only in PSMA+PC-3 PIP cells in-vitro, suggesting that NPA-carbamates may be PSMA substrates. In addition, in situ ligand minimization docking experiments showed a difference in the binding of 12 (XY-20) and 13 (XY-48). Although compounds 12 (XY-20) and 13 (XY-48) both have one less hydrogen bonding moiety compared to urea 9 (XY-I-26), compound 13 (XY-48) possesses a similar position with regards to the zinc molecule and G518 in the binding site. For compound 12 (XY-20) the hydrogen bonding distance to G518 is increased. The resulting weaker hydrogen bonding in 12 (XY-20) may be the reason for its lower PSMA binding affinity compared to both 9 (XY-I-26) and 13 (XY-48).

Example 2

Synthesis of Beta-Amino Acid Urea Agents for for Imaging of PSMA and Cancer Radiotherapy (R)-2-amino-3-(3-((S)-1,5-di-tert-butoxy-1,5-dioxopentan-2-yl)ureido)propanoic Acid L-glutamic acid di-tert-butyl ester hydrochloride 600 mg (2 mmol) and triethylamine 1 mL were dissolved in 20 mL anhydrous methylene chloride. The solution was cooled to −78° C. Triphosgene 200 mg (0.66 mmol) was dissolved in 3 mL anhydrous methylene chloride and added by drop. The reaction was slowly warmed up to room temperature and stirred for 30 min. (R)-3-amino-2-((tert-butoxycarbonyl)amino)propanoic acid 400 mg (2 mmol) and triethylamine 0.4 mL were added. The reaction was kept at room temperature for 24 h. The organic layer was washed with 2N HCl and dried with sodium sulfate. After the solvent was removed under vacuum, 1.0 g (R)-2-amino-3-(3-((S)-1,5-di-tert-butoxy-1,5-dioxopentan-2-yl)ureido)propanoic acid was obtained and used for the next steps without further purification. The yield was around 100%. ($^1$H NMR (400 MHz, CDCl$_3$): δ 6.17-6.00 (br, 3H). 4.31 (m, 2H), 3.71-3.51 (m, 2H), 2.37-2.32 (m, 2H), 2.11-2.06 (m, 1H), 1.91-1.80 (m, 1H) 1.51-1.41 (m, 27H). MS: 446 (M+H$^+$)

(S)-2-(3-((R)-2-amino-2-carboxyethyl)ureido)pentanedioic Acid (R)-2-amino-3-(3-((S)-1,5-di-tert-butoxy-1,5-dioxopentan-2-yl)ureido)propanoic acid 300 mg was treated with a 6 mL solution of TFA/methylene chloride(1/1) for 2 h. The final product was purified by HPLC in 150 mg, yield 60%. ($^1$H NMR (400 MHz, CDCl$_3$): δ 4.17 (dd, J1=9.6 Hz, J2=5.6 Hz, 1H), 4.00 (dd, J1=6.0 Hz, J2=4.0 Hz, 1H), 3.66 (dd, J1=15.2 Hz, J2=4.0 Hz, 1H), 3.56 (dd, J1=15.2 Hz, J2=6.0 Hz, 1H), 2.40 (t, J=7.2 Hz, 2H), 2.31-2.05 (m, 1H), 1.92-1.83 (m, 1H). MS: 278 (M+H$^+$)

NMR and MS for beta-amino acid ureas (Structures and PSMA binding are given in Example 3).

XY-34: MS: 440 (M+H$^+$)
XY-36: MS: 508 (M+H$^+$)
XY-35: MS: 585 (M+H$^+$)
XY-37: MS: 585 (M+H$^+$)
XY-40: MS: 513 (M+H$^+$)
XY-46: MS: 561 (M+H$^+$).

Example 3

Binding Affinity Data of Representative Compounds of Formula (I) and Formula (II)

TABLE 3

Binding Affinity Data of Representative Compounds of Formula (I) and Formula(II)

| Entry | Compound structure | IC$_{50}$ (nM) | K$_i$ (nM) | Cmpd |
|---|---|---|---|---|
| 1 | (structure shown) | 113 | 22 | XY-10 |

TABLE 3-continued

Binding Affinity Data of Representative Compounds of Formula (I) and Formula(II)

| Entry | Compound structure | IC$_{50}$ (nM) | K$_i$ (nM) | Cmpd |
|---|---|---|---|---|
| 2 | 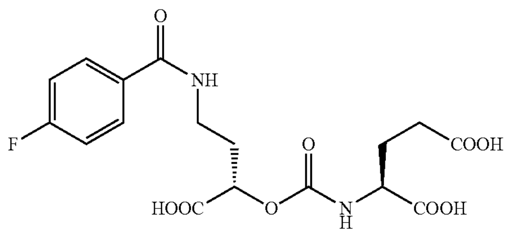 [SMILES: O=C(O)CC[C@H](NC(=O)O[C@@H](CCNC(=O)c1ccc(F)cc1)C(=O)O)C(=O)O] | 4,500 | 900 | XY-16 |
| 3 | 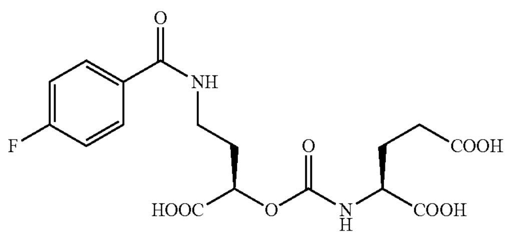 [SMILES: O=C(O)CC[C@H](NC(=O)O[C@H](CCNC(=O)c1ccc(F)cc1)C(=O)O)C(=O)O] | 4,900 | 980 | XY-17 |
| 4 | 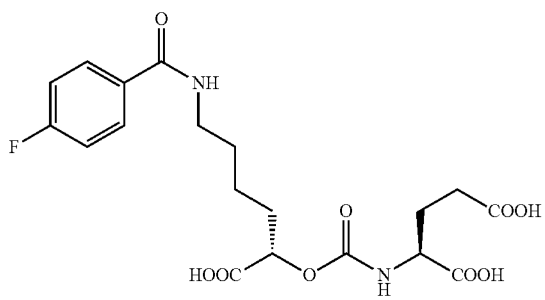 | 210 | 42 | XY-20 |
| 5 | 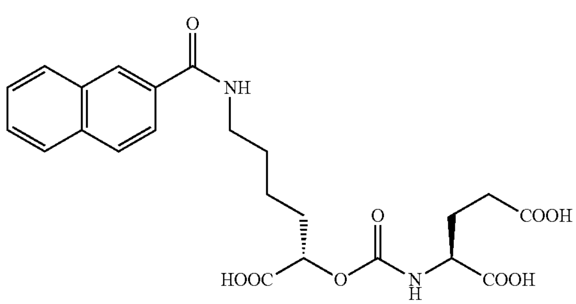 [SMILES: O=C(O)CC[C@H](NC(=O)O[C@@H](CCCCNC(=O)c1ccc2ccccc2c1)C(=O)O)C(=O)O] | 60 | 12 | XY-21 |
| 6 | 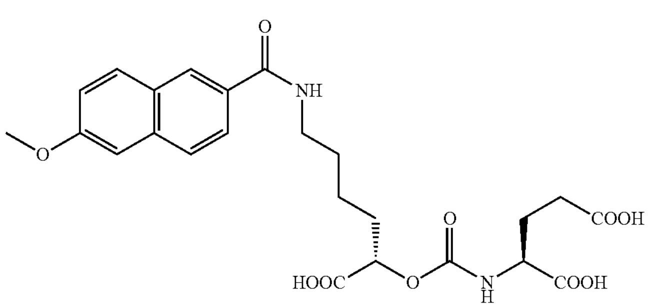 [SMILES: COc1ccc2cc(C(=O)NCCCC[C@H](OC(=O)N[C@@H](CCC(=O)O)C(=O)O)C(=O)O)ccc2c1] | 104 | 20 | XY-22 |

TABLE 3-continued

Binding Affinity Data of Representative Compounds of Formula (I) and Formula(II)

| Entry | Compound structure | IC$_{50}$ (nM) | K$_i$ (nM) | Cmpd |
|---|---|---|---|---|
| 7 | 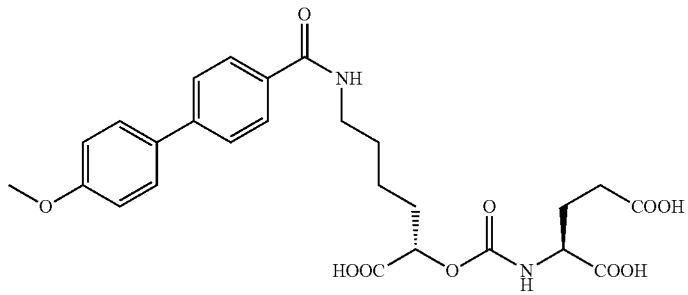 [SMILES: COc1ccc(-c2ccc(C(=O)NCCCC[C@H](OC(=O)N[C@@H](CCC(=O)O)C(=O)O)C(=O)O)cc2)cc1] | 30 | 6 | XY-23 |
| 8 | 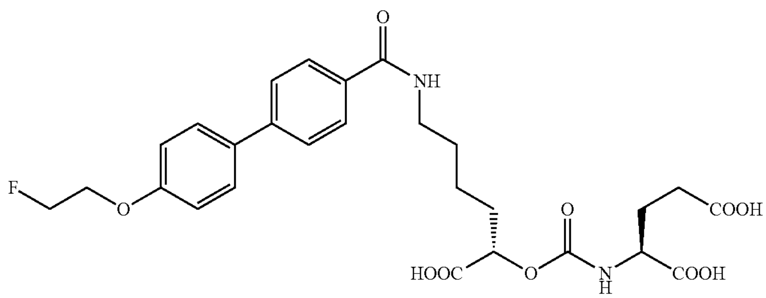 [SMILES: O=C(O)CC[C@H](NC(=O)O[C@@H](CCCCNC(=O)c1ccc(-c2ccc(OCCF)cc2)cc1)C(=O)O)C(=O)O] | 120 | 22 | XY-24 |
| 9 | 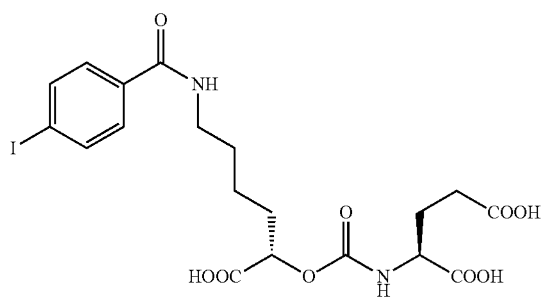 [SMILES: O=C(O)CC[C@H](NC(=O)O[C@@H](CCCCNC(=O)c1ccc(I)cc1)C(=O)O)C(=O)O] | 4.3 | 0.9 | XY-26 |
| 10 | 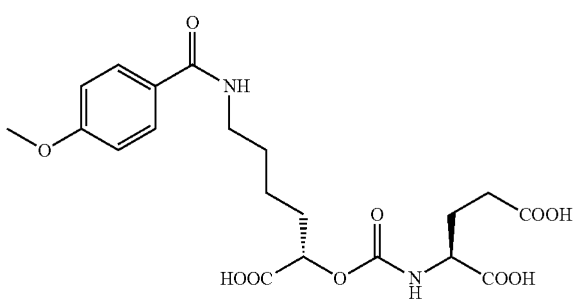 [SMILES: COc1ccc(C(=O)NCCCC[C@H](OC(=O)N[C@@H](CCC(=O)O)C(=O)O)C(=O)O)cc1] | 100 | 21 | XY-27 |
| 11 | 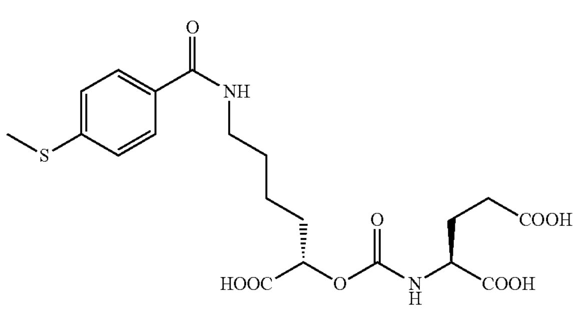 [SMILES: CSc1ccc(C(=O)NCCCC[C@H](OC(=O)N[C@@H](CCC(=O)O)C(=O)O)C(=O)O)cc1] | 24 | 4.8 | XY-28 |

TABLE 3-continued

Binding Affinity Data of Representative Compounds of Formula (I) and Formula(II)

| Entry | Compound structure | IC$_{50}$ (nM) | K$_i$ (nM) | Cmpd |
|---|---|---|---|---|
| 12 | 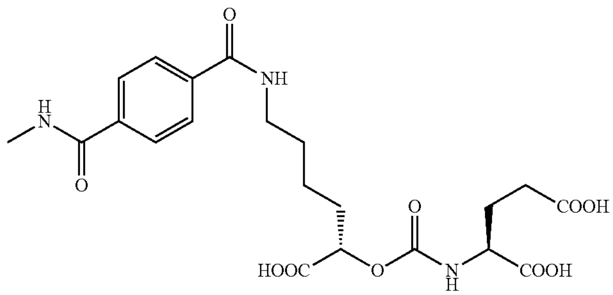 [SMILES: CNC(=O)c1ccc(C(=O)NCCCC[C@H](OC(=O)N[C@@H](CCC(=O)O)C(=O)O)C(=O)O)cc1] | 1,300 | 270 | XY-30 |
| 13 | 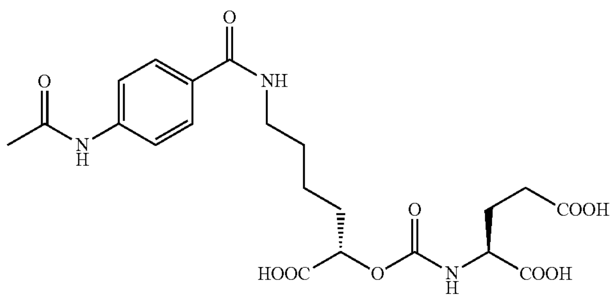 [SMILES: CC(=O)Nc1ccc(C(=O)NCCCC[C@H](OC(=O)N[C@@H](CCC(=O)O)C(=O)O)C(=O)O)cc1] | 660 | 130 | XY-29 |
| 14 | 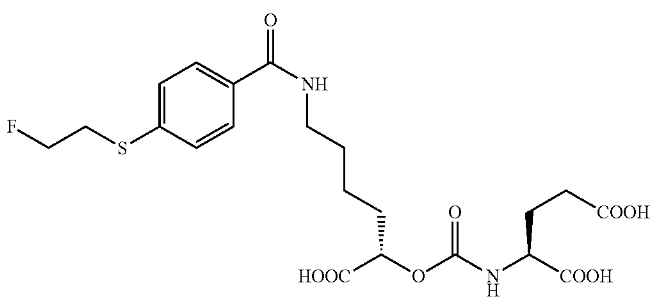 [SMILES: O=C(O)CC[C@H](NC(=O)O[C@@H](CCCCNC(=O)c1ccc(SCCF)cc1)C(=O)O)C(=O)O] | 41 | 8.3 | XY-38 |
| 15 | 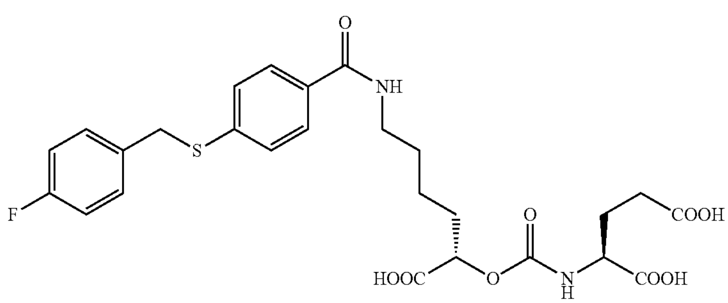 [SMILES: O=C(O)CC[C@H](NC(=O)O[C@@H](CCCCNC(=O)c1ccc(SCc2ccc(F)cc2)cc1)C(=O)O)C(=O)O] | 46 | 9.3 | XY-39 |
| 16 | 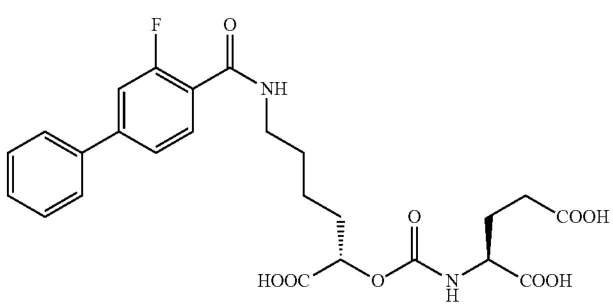 [SMILES: O=C(O)CC[C@H](NC(=O)O[C@@H](CCCCNC(=O)c1ccc(-c2ccccc2)cc1F)C(=O)O)C(=O)O] | 86 | 13 | XY-42 |

TABLE 3-continued
Binding Affinity Data of Representative Compounds of Formula (I) and Formula(II)
| Entry | Compound structure | IC$_{50}$ (nM) | K$_i$ (nM) | Cmpd |
|---|---|---|---|---|
| 17 | 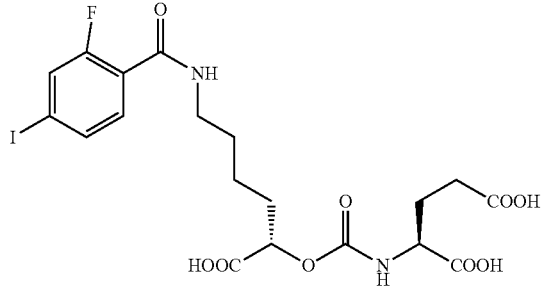 [SMILES: O=C(O)CC[C@H](NC(=O)O[C@@H](CCCCNC(=O)c1ccc(I)cc1F)C(=O)O)C(=O)O] | 1.6 | 0.32 | XY-43 |
| 18 | 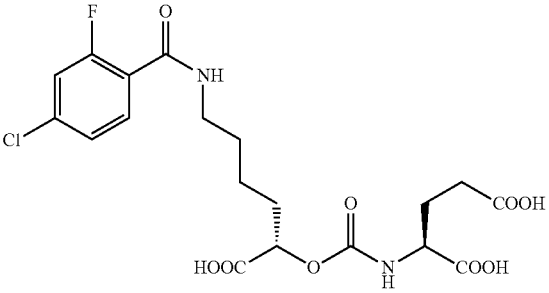 [SMILES: O=C(O)CC[C@H](NC(=O)O[C@@H](CCCCNC(=O)c1ccc(Cl)cc1F)C(=O)O)C(=O)O] | 192 | 38 | XY-49 |
| 19 | 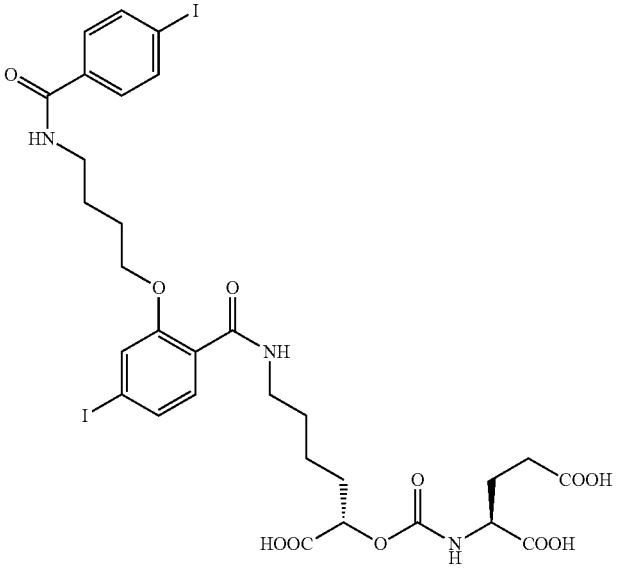 [SMILES: O=C(O)CC[C@H](NC(=O)O[C@@H](CCCCNC(=O)c1ccc(I)cc1OCCCCNC(=O)c1ccc(I)cc1)C(=O)O)C(=O)O] | 3,800 | 770 | XY-50 |
| 20 | 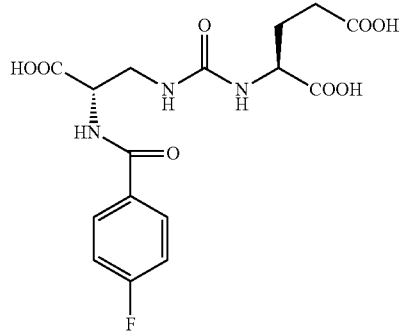 [SMILES: O=C(O)CC[C@H](NC(=O)NC[C@H](NC(=O)c1ccc(I)cc1)C(=O)O)C(=O)O] | 43,000 | 8,700 | XY-34 |

TABLE 3-continued
Binding Affinity Data of Representative Compounds of Formula (I) and Formula(II)
| Entry | Compound structure | IC$_{50}$ (nM) | K$_i$ (nM) | Cmpd |
|---|---|---|---|---|
| 21 | 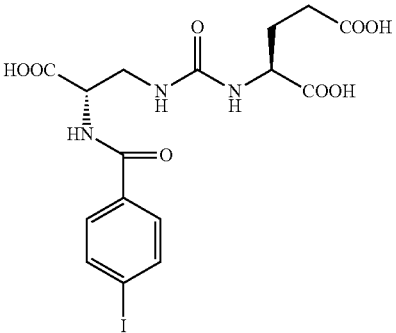 | 12,000 | 2,400 | XY-36 |
| 22 | 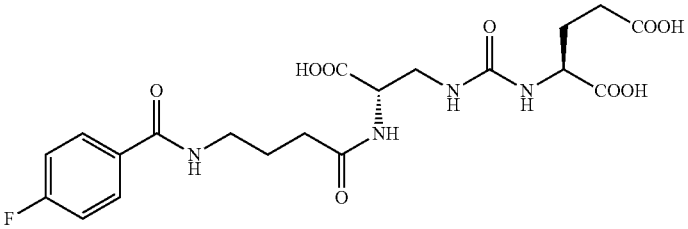 [SMILES: O=C(O)CC[C@H](NC(=O)NC[C@H](NC(=O)CCCNC(=O)c1ccc(F)cc1)C(=O)O)C(=O)O] | 8,000 | 1,600 | XY-35 |
| 23 | 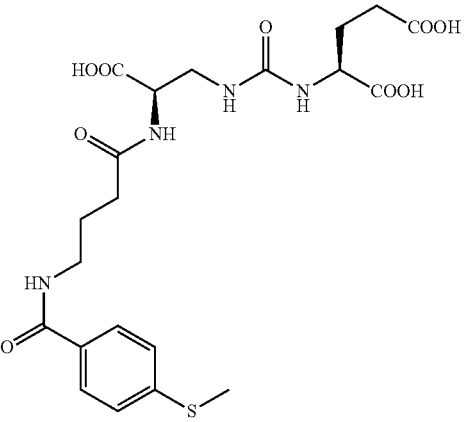 [SMILES: CSc1ccc(C(=O)NCCCC(=O)N[C@H](CNC(=O)N[C@@H](CCC(=O)O)C(=O)O)C(=O)O)cc1] | 1.3 | 0.26 | XY-40 |
| 24 | 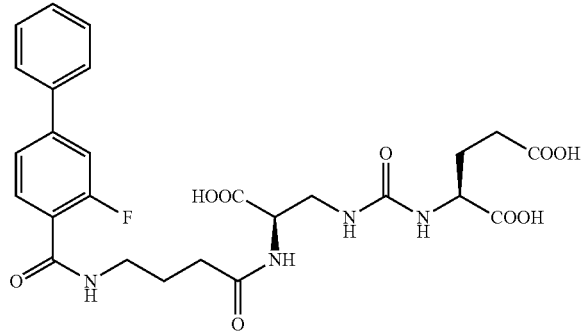 [SMILES: O=C(O)CC[C@H](NC(=O)NC[C@@H](NC(=O)CCCNC(=O)c1ccc(-c2ccccc2)cc1F)C(=O)O)C(=O)O] | 2.0 | 0.4 | XY-46 |

Some other additional data, including the binding affinity K, distribution coefficient CLogD, and PSA, of representative compounds of Formula (I) are provided in Table 4. In these exemplary, non-limiting embodiments, the most potent compounds contain a fluorine atom at $R_1$ and a large halogen, e.g., either Br or I, or a phenyl ring at the 4-position of the arylbenzoyl moiety, i.e., $R_2$ and are annotated with an "*".

TABLE 4

Binding Affinity Data of Representative Compounds of Formula (I)

| Cmpd | $X_2$ | $X_1$ | X | $R_1$ | $R_2$ | $K_i$(nM) | CLogD | PSA |
|---|---|---|---|---|---|---|---|---|
| DCFBC† | — | — | — | — | — | 14 | -4.7 | 178 |
| DCIBC†† | — | — | — | — | — | 0.03 | — | — |
| YC-I-27 | NH | NH | CH | H | I | 0.01 | -5.2 | 182 |
| YC-I-26 | NH | NH | CH | H | F | 0.3 | -5.6 | 182 |
| DCFPyL††† | NH | NH | N | H | F | 1.1 | -6.4 | 195 |
| C8†††† | — | — | — | — | — | 0.35 | — | — |
| XY-44* | NH | NH | CH | F | I | 0.017 | -5.5 | 182 |
| XY-45* | NH | NH | CH | F | $C_6H_5$ | 0.1 | -5.1 | 182 |
| XY-59 | NH | NH | CH | H | Br | 0.02 | -5.4 | 182 |
| XY-58* | NH | NH | CH | F | Br | 0.036 | -5.8 | 182 |
| XY-20 | O | NH | CH | H | F | 42 | -4.7 | 179 |
| XY-26 | O | NH | CH | H | I | 0.9 | -4.3 | 179 |
| XY-28 | O | NH | CH | H | $SCH_3$ | 4.8 | -4.6 | 205 |
| XY-43* | O | NH | CH | F | I | 0.32 | -4.6 | 179 |
| XY-42 | O | NH | CH | F | $C_6H_5$ | 13 | -4.2 | 179 |
| XY-49 | O | NH | CH | F | Cl | 38 | -5.5 | 179 |
| XY-56 | O | NH | CH | F | Br | — | -4.9 | 179 |

†DCFBC is N-[N-[(S)-1,3-Dicarboxypropyl]carbamoyl]-4-fluorobenzyl-1-cysteine:

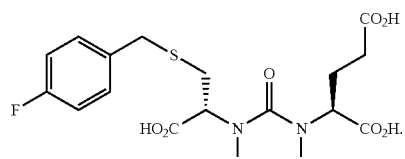

††DCIBC is N-[N-[(S)-1,3-Dicarboxypropyl]carbamoyl]-4-iodobenzyl-1-cysteine

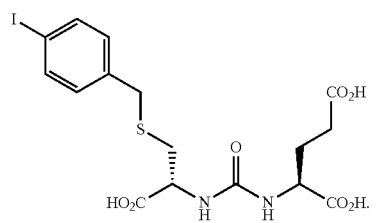 [SMILES: O=C(O)CC[C@H](NC(=O)N[C@@H](CSCc1ccc(I)cc1)C(=O)O)C(=O)O]

†††DCFPyL is 2-(3-{1-carboxy-5-[(6-fluoro-pyridine-3-carbonyl)-amino]-pentyl}-ureido)-pentanedioic acid:

TABLE 4-continued

Binding Affinity Data of Representative Compounds of Formula (I)

| Cmpd | $X_2$ | $X_1$ | X | $R_1$ | $R_2$ | $K_i$(nM) | CLogD | PSA |
|---|---|---|---|---|---|---|---|---|

††††C8 is

Example 4

Synthesis and Use of Radiohalogenated Lysine, Glutamate and Cysteine-NPA Carbamate Compounds for Imaging and Cancer Radiotherapy The development of low molecular weight radiotherapeutic agents is different from developing radiopharmaceuticals for imaging in that longer tumor residence times are required for the former. Many radionuclides, primarily β- and alpha emitters, have been investigated for targeted radioimmunotherapy and include both radiohalogens and radiometals. The studies presented in the disclosed subject matter have been focused on radiohalogens, $^{125}$, $^{123}$I, $^{131}$I, $^{211}$At, $^{77}$Br (Table 5), with several specific examples of appropriate ways of introducing them into PSMA-targeting molecules. Several of these radionuclides ($^{123}$I, $^{131}$I, $^{77}$Br) also emit imaging gamma rays providing both imaging and radiotherapeutic applications.

TABLE 5

| Therapeutic Radionuclides | |
|---|---|
| β-particle emitters | $^{90}$Y, $^{131}$I, $^{177}$Lu, $^{153}$Sm, $^{186}$Re, $^{188}$Re, $^{67}$Cu, $^{212}$Pb, $^{166}$Ho, $^{47}$Sc |
| α-particle emitters | $^{225}$Ac, $^{213}$Bi, $^{212}$Bi, $^{211}$At, $^{212}$Pb, $^{227}$Th, $^{223}$Ra |
| Auger electron emitters | $^{125}$I, $^{123}$I, $^{67}$Ga, $^{111}$In, $^{80m}$Br, $^{77}$Br |

These radiohalogens are covalently bound to the targeting moiety and unlike large chelated radiometals are small enough that the entire radiolabeled PSMA inhibitor can fit within the PSMA binding cavity thereby retaining the high binding affinity. The same radiolabeled prosthetic groups can be conjugated to linker-inhibitor conjugates to move the radiolabeled portion of the inhibitor to the exterior of the PSMA protein.

Radiohalogenated PSMA binding radiotherapeutics can be built upon multiple PSMA binding scaffolds. The urea based scaffolds include: the lysine-glutamate urea, cysteine-glutamate urea, and glutamate-glutamate urea (FIG. 10). PSMA inhibitors built upon novel lysine-reversed carbamate scaffold (NPA) have been disclosed in example 1 of the present application, and cysteine —NPA carbamate and glutamate—NPA carbamate scaffolds, as shown FIG. 11, have been envisioned. These compounds are based on extensive structure-activity relationships—not merely of the imaging precursors or PSMA binding compounds, but on actual imaging agents already synthesized and tested in vivo—as well as on molecular modeling.

The lead compound in the lysine-glutamate ureas is YC-I-27. This iodinated compound has high and prolonged tumor uptake and a very high PSMA binding affinity Ki=0.01 nM (Chen et al., 2008). It has also been co-crystalized with PSMA. This has shown that the bulky iodo-phenyl moiety is accommodated by a hydrophobic auxillary sub-pocket extending beyond the normal binding pocket and the additional hydrophobic-hydrophobic interactions accounts for the high binding affinity (Barinka et al., 2008). Table 4 summarizes the halogen containing compounds that have been prepared to date and demonstrates the high binding affinity for the halogenated compounds using the new lysine-NPA reversed carbamate scaffold. This indicates the utility of the new Lysine-NPA scaffold and suggests that it can be applied to PSMA targeted radiotherapy of prostate cancer. This also suggests that cysteine-NPA scaffold as well as glutamate-NPA carbamate scaffold will also produce PSMA targeted radiotherapeutic agents.

Synthesis of Radiohalogenated Lysine—NPA Carbamate Compounds.

Parent lysine-NPA carbamate scaffold reported in example 1 of the present application, and can be utilized, as shown in Scheme 4, to prepare radiohalogened lysine—NPA carbamates utilizing known stannane containing prosthetic groups (Garg, et al., 1991; Vaidyanathan G, and Zalutsky M R, 2007; Talanov et al., 2006).

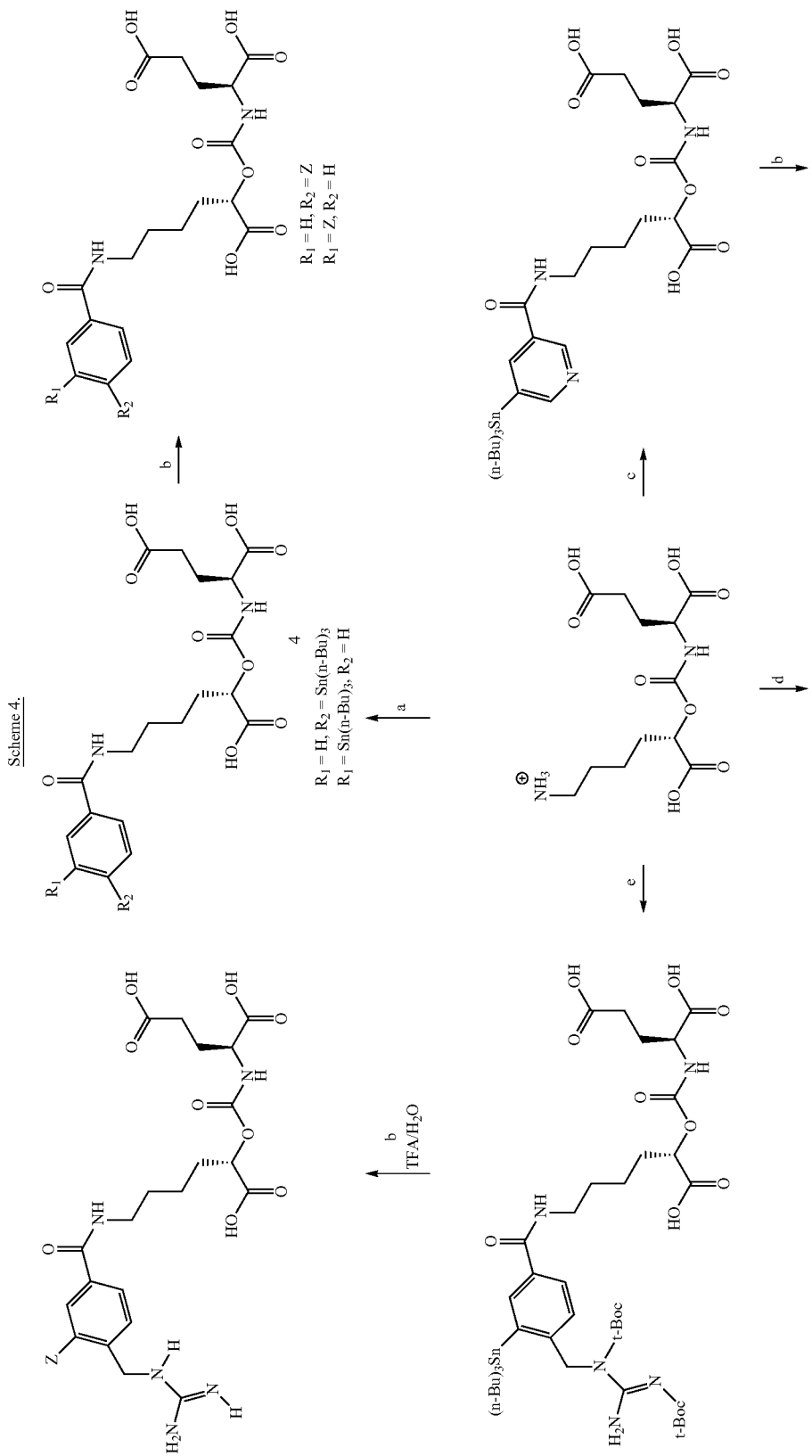

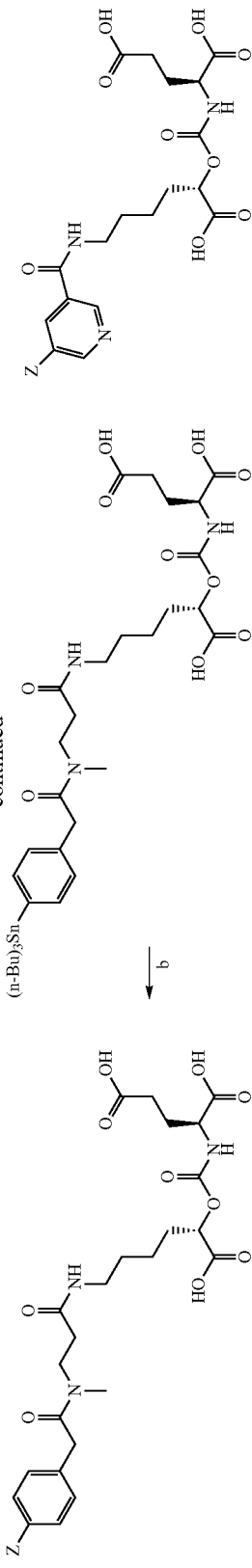
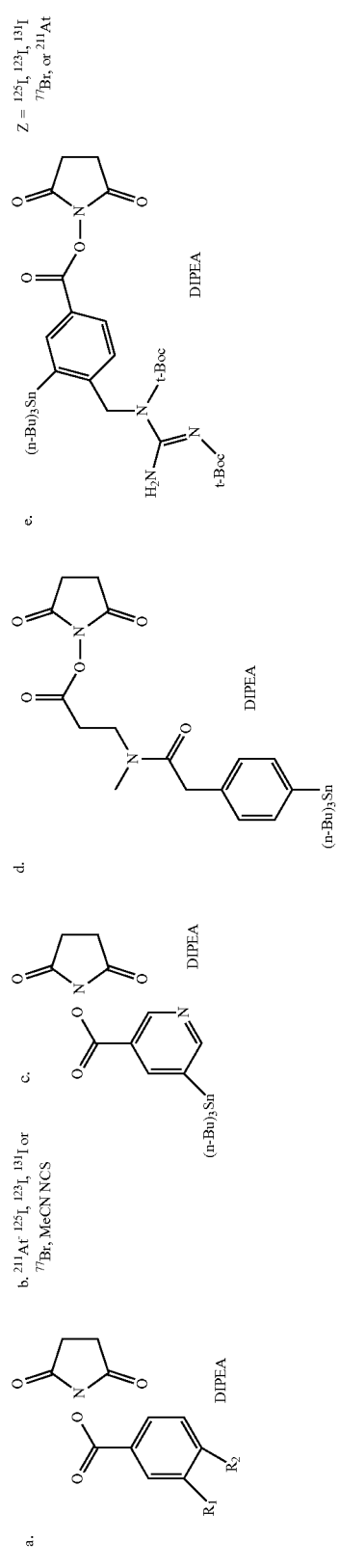

Synthesis of Radiohalogenated Glutamate-NPA Carbamate Compounds.

Glutamate-glutamate ureas have been used by others to conjugate bulky radiometal chelating agents, fluorescent molecule, and chemotherapeutics (Kularatne et al., 2009; International Patent Applications Nos. PCT/US2008/073375, PCT/US2009/061067, and PCT/US2011/026238). These compounds are too large to utilize the non-pharmacophore binding pocket and must utilize a void region to extend outside of the protein. A synthetic route to an analogous radiohalogenated glutamate-NPA carbamate is shown in Scheme 5.

Synthesis of Radiohalogenated Cysteine-NPA Carbamate Compound.

The cysteine-glutamate urea scaffold has been utilized by us for PSMA binding and imaging for over 10 years starting with C-11 labeled DCMC (Pomper et al., 2002; Foss et al., 2005), continuing with F-18 labeled DCFBC (Mease et al., 2008; Cho et al., 2012) both for PET imaging with the latter currently in use in patients, and I-125 labeled DCIBC (Dusich, 2008) for SPECT imaging and or radiotherapy (FIG. 11).

A synthetic route to analogous radiohalogenated cysteine-NPA carbamates is shown in Scheme 6.

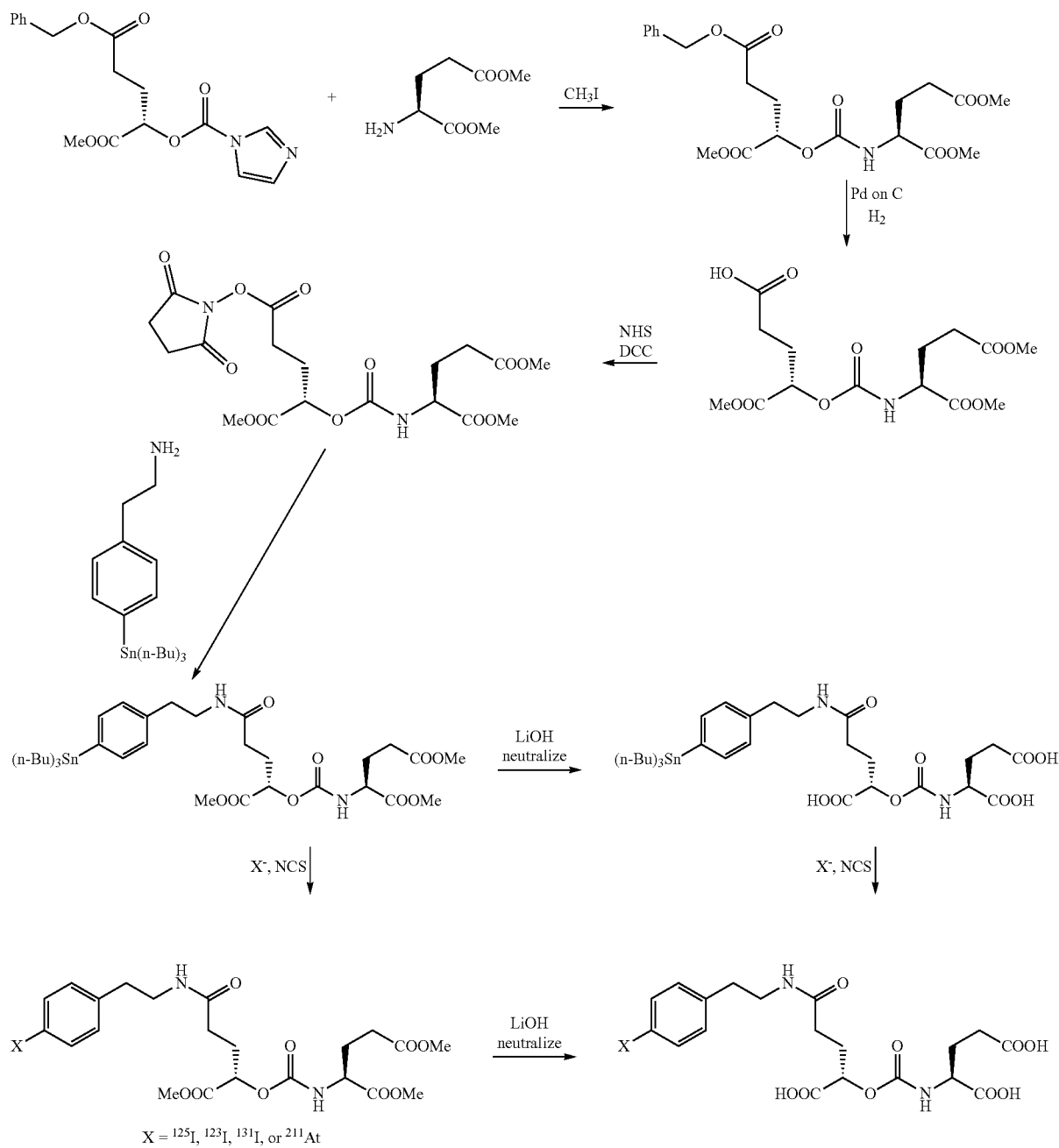

Scheme 6

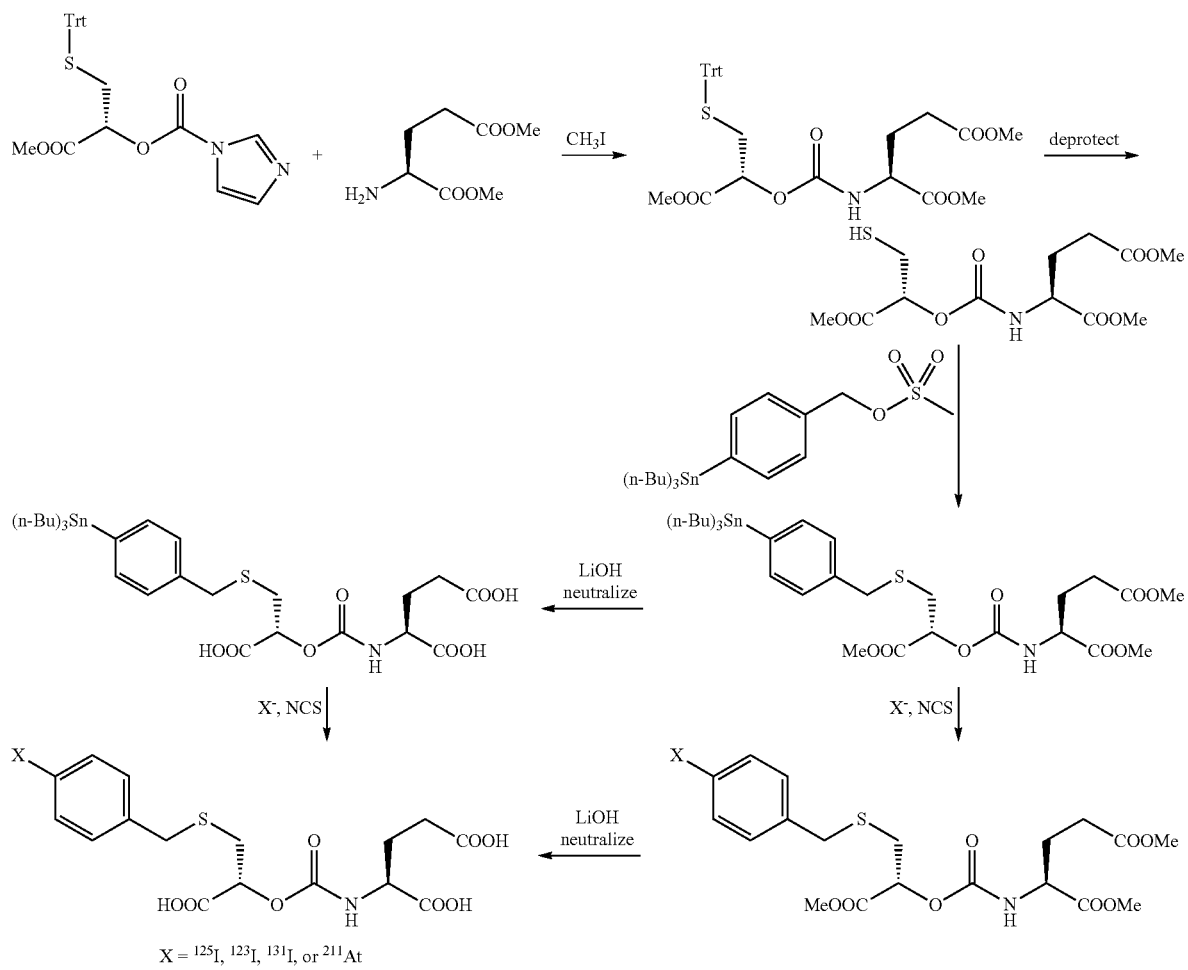

Homologs of the cysteine-NPA carbamates may have even higher binding affinity because the extended alkyl chain will permit a deeper penetration of the 4-halobenzyl group into the non-pharmacophore binding pocket. These compounds can be prepared analogously using Scheme 3 starting with commercial N$^\alpha$-Fmoc-S-trityl-L-homocysteine and L-5-[S-trityl]-[N-9-fluorenylmethyloxycarbonyl]-mercaptonorvaline.

Lysine glutamate ureas and glutamate-glutamate ureas linker conjugates have been used to attach bulky radiometal chelates or fluorescent molecules for PSMA specific imaging and radiotherapy, with a focus on the use of polyethylene glycol (PEG) and lysine-suberate linkers (Banerjee et al., 2008; Chen et al., 2012). The new PSMA binding scaffolds described herein can also be used to prepare radiolabeled linker conjugates. A route to the synthesis of a lysine-suberate-lysine-NPA carbamate and its use in preparing radiohalogenated linker NPA carbamates is shown in Scheme 7.

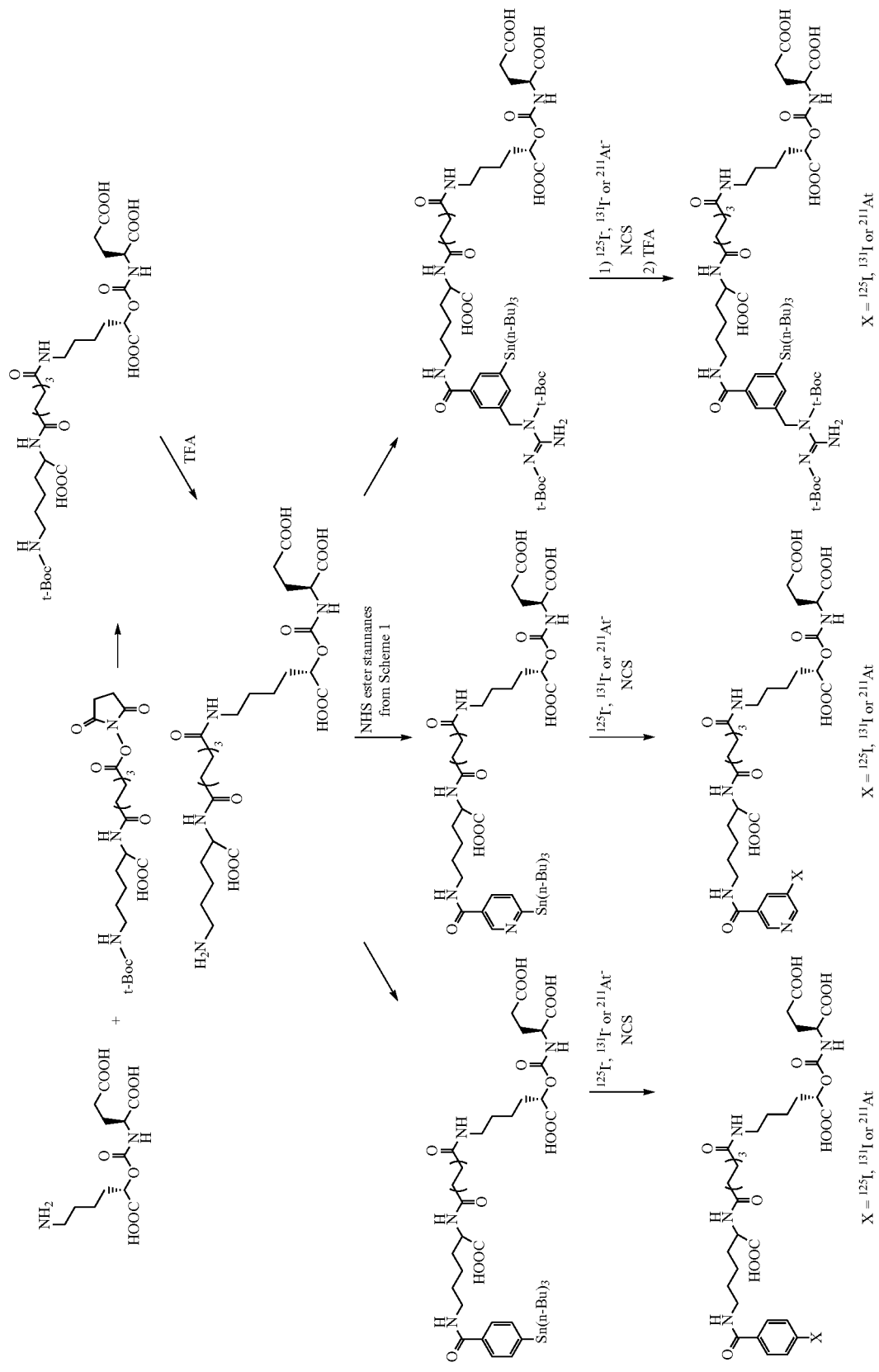

Example 4

PSMA Binding Carbamates Conjugated to Fluorescent Molecules for PSMA Targeted Imaging Guided Surgery and Photodynamic Therapy The preparation and use of PSMA binding ureas conjugated to fluorescent molecules via various linkers for imaging PSMA expressing tumors and tissues (Chen et al., 2009; Banerjee et al., 2011; Chen et al., 2012) and photodynamic therapy (PDT) have been previously described. Two specific examples of IR-Dye-800-CW-linker-ureas are shown in FIG. 13. PSMA inhibitors built upon lysine-carbamate scaffolds (NPA) including F-18 labeled analogs have been disclosed in the present application, and the F-18 labeled NPA compounds demonstrated selective uptake in PSMA positive tumor mouse xenografts. Various dyes and linkers previously disclosed in Patent Application No. PCT/US2010/028020 for use with ureas can be attached to the NPA scaffolds to provide novel optical agents for imaging prostate cancer. A route to the synthesis is shown in scheme 8.

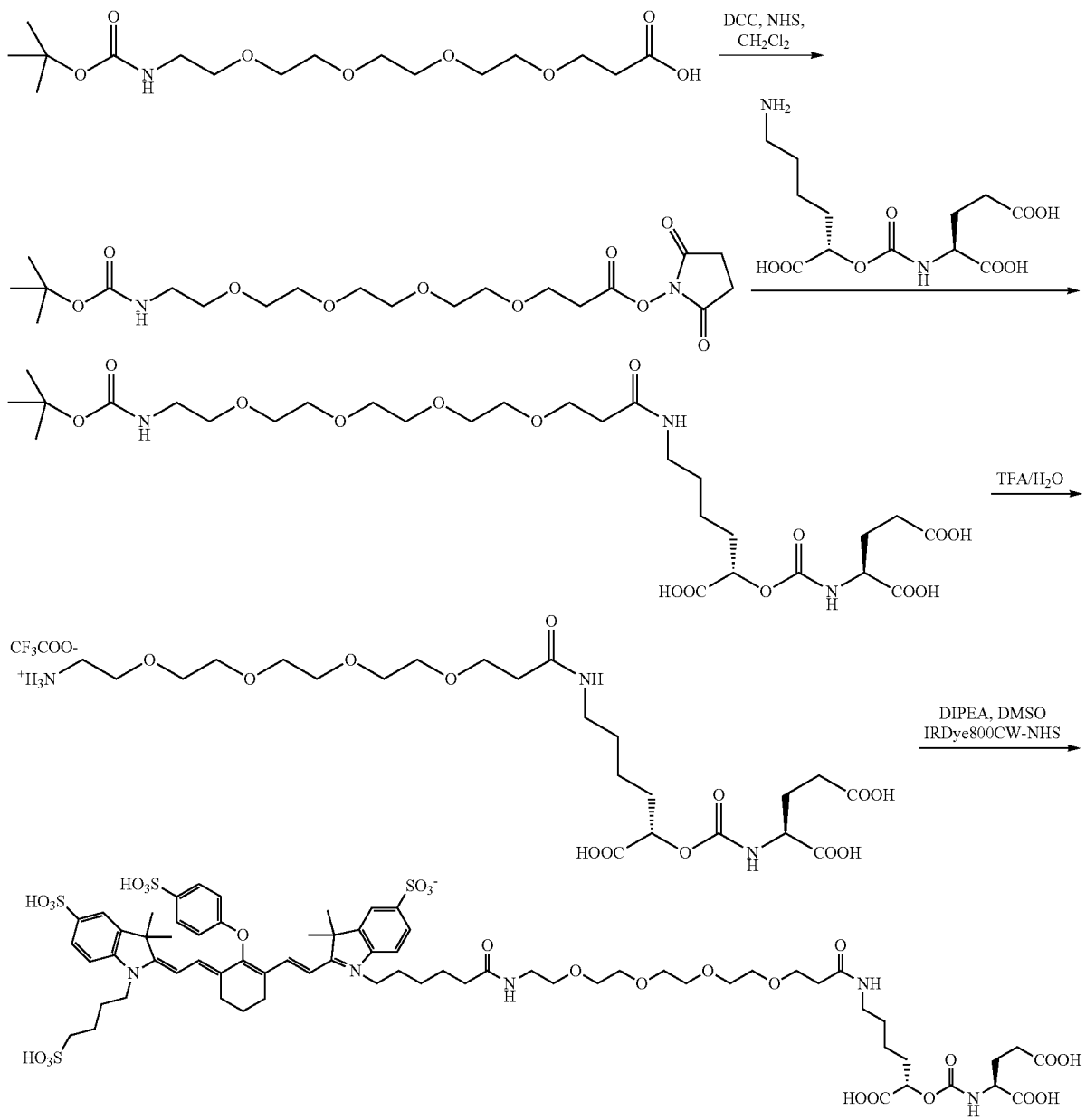

Scheme 8.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein International PCT Patent Application Publication No. PCT/US2008/073375 to Low PS, Kularatne SA. for PSMA binding ligand-linker conjugates and methods for using, published 2009 Feb. 26 (WO 2009/026177A1);

International PCT Patent Application Publication No. PCT/US2009/061067 to Low PS, Kularatne S A. for PSMA binding ligand-linker conjugates and methods for using, published 2010 Apr. 22 (WO 2010/045598 A2);

International PCT Patent Application Publication No. PCT/US2011/026238 to Low PS, Chelvam V, Kim Y. for PSMA binding ligand-linker conjugates and methods for using, published 2011 Sep. 1 (WO 2011/106639 A1);

International PCT Patent Application Publication No. PCT/US03/00680 to Pomper M G, Zhang J, Kozikowski A P, Musachio J L. for Imaging agents and methods of imaging NAALADase of PSMA, published 2003 Jul. 24 (WO 03/60523 A1);

International PCT Patent Application Publication No. PCT/US2008/007947 to Pomper, M. G., Ray, S., Mease, R. C., Foss, C. for Labeled inhibitors of prostate specific membrane antigen (PSMA), biological evaluation, and use as imaging agents, published 2008 Dec. 31 (WO 2009/002529 A2);

International PCT Patent Application Publication No. PCT/US2009/052456 to Pomper M G, Mease R C, Chen Y. for Preparation of glutamic acid heterodimer prostate-specific membrane antigen PSMA binding agents for therapeutic and imaging use, published 2010 Feb. 4 (WO 2010/014933 A2);

International PCT Patent Application Publication No. PCT/US2010/028020 to Pomper, Martin G.; Mease, Ronnie C.; Ray, Sangeeta; Chen, Ying. for PSMA-targeting compounds and uses thereof, published 2010 Sep. 23 (WO 2010/108125 A2);

International PCT Patent Application Publication No. PCT/US2012/067162 to Pomper, Martin G. Mease, Ronnie C., Ray, Sangeeta, Shallal, Hassan for Homomultivalent and heteromultivalent inhibitors of prostate specific membrane antigen (PSMA) and uses thereof, published 2013 Jun. 6 (WO2013/082338 A1)

International PCT Patent Application Publication No. PCT/US2011/026238 to Low P. S., Chelvam V., Kim Y. for PSMA binding ligand-linker conjugates and methods for using, published 2011 Sep. 1 (WO2011/106639);

International PCT Patent Application Publication No. PCT/US2009/061067 to Low P. S., Chelvam V., Kim Y. for PSMA binding ligand-linker conjugates and methods for using, published 2010 Apr. 22 (WO 2010/045598 A2)

International PCT Patent Application Publication No. PCT/US2008/073375 to Low P. S., Chelvam V., Kim Y. for PSMA binding ligand-linker conjugates and methods for using, published 209/02/26 (WO 2009/026177 A1);

U.S. Patent Application Publication No. US2004/0054190 A1 to Pomper M G, Zhang J, Kozikowski A P, Musachio J L. for Imaging agents and methods of imaging NAALADase of PSMA, Licensed to: Molecular Insight Pharmaceuticals, Inc. published 2004 Mar. 18 (Ser. No. 10/340,864);

U.S. Patent Application Publication No. US2008/0193381 A1 to Babich J W, Zimmerman C N, Maresca K P. for Heterodimers of glutamic acid, published 2008 Aug. 14 (Ser. No. 11/936,659);

U.S. Patent Application Publication No. US2013/0034494 A1 to Babich J W, Zimmerman C, Joyal J L, Lu G. for Radiolabeled prostate specific membrane antigen inhibitors, published 2013 Feb. 7 (Ser. No. 13/566,674); Afshar-Oromieh, A.; Haberkorn, U.; Eder, M.; Eisenhut, M.; Zechmann, C. M., [68Ga]Gallium-labelled PSMA ligand as superior PET tracer for the diagnosis of prostate cancer: comparison with 18F-FECH. *European journal of nuclear medicine and molecular imaging* 2012, 39 (6), 1085-6;

Afshar-Oromieh, A.; Malcher, A.; Eder, M.; Eisenhut, M.; Linhart, H. G.; Hadaschik, B. A.; Holland-Letz, T.; Giesel, F. L.; Kratochwil, C.; Haufe, S.; Haberkorn, U.; Zechmann, C. M., PET imaging with a [68Ga]gallium-labelled PSMA ligand for the diagnosis of prostate cancer: biodistribution in humans and first evaluation of tumour lesions. *European journal of nuclear medicine and molecular imaging* 2013, 40 (4), 486-95;

Afshar-Oromieh, A.; Haberkorn, U.; Hadaschik, B.; Habl, G.; Eder, M.; Eisenhut, M.; Schlemmer, H. P.; Roethke, M. C., PET/MRI with a 68Ga-PSMA ligand for the detection of prostate cancer. *European journal of nuclear medicine and molecular imaging* 2013, 40 (10), 1629-30;

Afshar-Oromieh, A.; Zechmann, C. M.; Malcher, A.; Eder, M.; Eisenhut, M.; Linhart, H. G.; Holland-Letz, T.; Hadaschik, B. A.; Giesel, F. L.; Debus, J.; Haberkorn, U., Comparison of PET imaging with a (68)Ga-labelled PSMA ligand and (18)F-choline-based PET/CT for the diagnosis of recurrent prostate cancer. *European journal of nuclear medicine and molecular imaging* 2014, 41 (1), 11-20;

Afshar-Oromieh, A.; Avtzi, E.; Giesel, F. L.; Holland-Letz, T.; Linhart, H. G.; Eder, M.; Eisenhut, M.; Boxler, S.; Hadaschik, B. A.; Kratochwil, C.; Weichert, W.; Kopka, K.; Debus, J.; Haberkorn, U., The diagnostic value of PET/CT imaging with the (68)Ga-labelled PSMA ligand HBED-CC in the diagnosis of recurrent prostate cancer. *European journal ofnuclear medicine and molecular imaging* 2015, 42 (2), 197-209;

Ai-Darwich, M. J., Plenevaux, A., Lemair3e, C., Fiore, G. D., Christianes, L., Comar, D., Luxen, A., Enantioselective synthesis of no-carrieradded (S)-4-chloro-2-[$^{18}$F] fluorophenylalanine and (S)-a-methyl)-4-chloro-2-[$^{18}$F] fluorophenylalanine. J. Fluor. Chem. 1996, 80, 117-124;

Bander, N. H.; Milowsky, M. I.; Nanus, D. M.; Kostakoglu, L.; Vallabhajosula, S.; Goldsmith, S. J., Phase I trial of 177lutetium-labeled J591, a monoclonal antibody to prostate-specific membrane antigen, in patients with androgen-independent prostate cancer. *Journal of clinical oncology: official journal of the American Society of Clinical Oncology* 2005, 23 (21), 4591-601;

Banerjee S R, Foss C A, Castanares M, Mease R C, Byun Y, Fox J J, Hilton J, Lupold S, Kozikowski A P, Pomper M G. Synthesis and evaluation of technetium-99m- and rhenium-labeled inhibitors of the prostate-specific membrane antigen (PSMA). J Med Chem 2008; 51:4504-4517;

Banerjee S R, Pullambhatla M, Byun Y, Nimmagadda S, Foss C A, Green G, Fox J J, Lupold S E, Mease R C, Pomper M G. Sequential SPECT and optical imaging of experimental models of prostate cancer with a dual modality inhibitor of the prostate-specific membrane antigen. Angew Chem Int Ed Engl 2011; 50:9167-70.

Banerjee S R, Pullambhatla M, Byun Y, Nimmagadda S, Green G, Fox J J, Horti A, Mease R C, Pomper M G. 68Ga-labeled inhibitors of prostate-specific membrane antigen (PSMA) for imaging prostate cancer. J Med Chem 2010, 53:5333-5341;

Banerjee, S. R, Pullambhatla, M., Foss, C. A., Nimmagadda, S. et al. 64Cu-labeled inhibitors of prostate-specific membrane antigen for PET imaging of prostate cancer. Journal of medicinal chemistry, 2014, 57(6), 2657-69;

Banerjee, S. R.; Foss, C. A.; Pullambhatla, M.; Wang, Y.; Srinivasan, S.; Hobbs, R.; Baidoo, K. E.; Brechbiel, M. W.; Nimmagadda, S.; Mease, R. C.; Sgouros, G.; Pomper, M. G., Preclinical Evaluation of 86Y-Labeled Inhibitors of Prostate-Specific Membrane Antigen for Dosimetry Estimates. *Journal of nuclear medicine: official publication, Society of Nuclear Medicine* 2015;

Barinka C, Byun Y, Dusich C L, Ray S, Chen Y, Castanares M, Kozikowski A P, Mease R C, Pomper M G, Lubkowski J. Interactions between Human Glutamate Carboxypeptidase II and Urea-based Inhibitors: Structural Characterization. J Med Chem, 2008; 51:7737-7743;

Barinka, C.; Sacha, P.; Sklenar, J.; Man, P.; Bezouska, K.; Slusher, B. S.; Konvalinka, J., Identification of the N-glycosylation sites on glutamate carboxypeptidase II necessary for proteolytic activity. *Protein science: a publication of the Protein Society* 2004, 13 (6), 1627-35;

Barrett, J. A.; Coleman, R. E.; Goldsmith, S. J.; Vallabhajosula, S.; Petry, N. A.; Cho, S.; Armor, T.; Stubbs, J. B.; Maresca, K. P.; Stabin, M. G.; Joyal, J. L.; Eckelman, W. C.; Babich, J. W., First-in-Man Evaluation of 2 High-Affinity PSMA-Avid Small Molecules for Imaging Prostate Cancer. *Journal of nuclear medicine: official publication, Society of Nuclear Medicine* 2013, 54 (3), 380-7;

Byun, Y., Mease, R. C., Lupold, S., Pomper, M. G., Drug Design of Zinc-Enzyme Inhibitors. Functional Structureal and Disease Applications. In *Recent Developments of Diagnostic and Therapeutic Agents Targeting Glutamate Carboxypeptidase II (GCPII)* Supuran, C. T., Winum, J. Y., Ed. John Wiley & Sons: Hoboken, 2009; pp 881-910;

Chang, S. S.; Reuter, V. E.; Heston, W. D.; Bander, N. H.; Grauer, L. S.; Gaudin, P. B., Five different anti-prostate-specific membrane antigen (PSMA) antibodies confirm PSMA expression in tumor-associated neovasculature. *Cancer Res* 1999, 59 (13), 3192-8;

Chang, S. S.; Reuter, V. E.; Heston, W. D.; Gaudin, P. B., Comparison of anti-prostate-specific membrane antigen antibodies and other immunomarkers in metastatic prostate carcinoma. *Urology* 2001, 57 (6), 1179-83;

Cheng, Y.; Prusoff, W. H., Relationship between the inhibition constate (K1) and the concentration of inhibitor which causes 50 percent inhibition (I50) of an enzymatic reaction. *Biochem Pharmcol* 1973, 22, 3099-3108;

Chen, Y.; Foss, C. A.; Byun, Y.; Nimmagadda, S.; Pullambhatla, M.; Fox, J. J.; Castanares, M.; Lupold, S. E.; Babich, J. W.; Mease, R. C.; Pomper, M. G., Radiohalogenated Prostate-Specific Membrane Antigen (PSMA)-Based Ureas as Imaging Agents for Prostate Cancer. *Journal of medicinal chemistry* 2008, 51 (24), 7933-7943;

Chen Y, Dhara S, Banerjee S, Byun Y, Pullambhatla M, Mease R C, Pomper M G. A low molecular weight PSMA-based fluorescent imaging agent for cancer. Biochem. Biophys Res. Commun. 390: 624-629 (2009);

Chen, Y.; Pullambhatla, M.; Banerjee, S. R.; Byun, Y.; Stathis, M.; Rojas, C.; Slusher, B. S.; Mease, R. C.; Pomper, M. G., Synthesis and biological evaluation of low molecular weight fluorescent imaging agents for the prostate-specific membrane antigen. Bioconjugate chemistry 2012, 23 (12), 2377-85;

Chen, Y.; Pullambhatla, M.; Foss, C. A.; Byun, Y.; Nimmagadda, S.; Senthamizhchelvan, S.; Sgouros, G.; Mease, R. C.; Pomper, M. G., 2-(3-{1-Carboxy-5-[(6-[18F] fluoro-pyridine-3-carbonyl)-amino]-pentyl}-ureido)-pen tanedioic acid, [18F]DCFPyL, a PSMA-based PET imaging agent for prostate cancer. *Clin Cancer Res* 2011, 17 (24), 7645-53;

Cho S Y, Gage K L, Mease R C, et al. Biodistribution, tumor detection, and radiation dosimetry of 18F-DCFBC, a low molecular weight inhibitor of PSMA, in patients with metastatic prostate cancer. J. Nucl. Med. 2012; 53:1883-1891.

Dekker B, Keen H, Shaw D, Disley L, Hastings D, Hadfield J, Reader A, Allan D, Julyan P, Watson A, Zweit J. Fundtional comparison of annexin V analogues labeled indirectly and directly with iodine-124. *Nuclear Medicine and Biology* 2005; 32:403-413;

Dusich C L. Imaging prostate cancer: Design, synthesis and biological evaluation of optical and radioactive prostate-specific membrane antigen (PSMA) inhibitors. PhD Thesis Johns Hopkins University 2008;

Eder, M.; Schafer, M.; Bauder-Wust, U.; Hull, W. E.; Wangler, C.; Mier, W.; Haberkorn, U.; Eisenhut, M., 68Ga-complex lipophilicity and the targeting property of a urea-based PSMA inhibitor for PET imaging. Bioconjugate chemistry 2012, 23 (4), 688-97;

Foss C A, Mease R C, Fan H, Wang Y, Ravert H T, Dannals R F, Olszewski R T, Heston W D, Kozikowski A P, Pomper M G. Radiolabeled small molecule ligands for prostate-specific membrane antigen: in vivo imaging in experimental models of prostate cancer. Clin Cancer Res 2005; 11:4022-4028;

Foss, C. A.; Mease, R. C.; Cho, S. Y.; Kim, H. J.; Pomper, M. G., GCPII imaging and cancer. *Current medicinal chemistry* 2012, 19 (9), 1346-59;

Garg S, Garg P K, Zalutsky M R. N-succinimidyl 5-(trialkylstannyl)-3-pyridinecarboxylates: a new class of reagents for protein radioiodination. *Bioconjugate Chem.* 1991; 2:50-56;

Ghosh, A.; Heston, W. D., Tumor target prostate specific membrane antigen (PSMA) and its regulation in prostate cancer. *Journal of cellular biochemistry* 2004, 91 (3), 528-39;

Glaser, M., Arstad, E., Luthra, S. K., Robins, E. G., Two-step radiosynthesis of [18F]N-succinimidyl-4-fluorobenzoate ([$^{18}$F]SFB. *J. Label. Compd. Radiopharm.* 2009, 52, 327-330;

Hillier S M, Maresca K P, Femia F J, Marquis J C, Foss C A, Nguyen N, Zimmerman C N, Barrett J A, Eckelman W C, Pomper M G, Joyal J L, Babich J W. Preclinical Evaluation of Novel Glutamate-Urea-Lysine Analogues That Target Prostate-Specific Membrane Antigen as Molecular Imaging Pharmaceuticals for Prostate Cancer. Cancer Res 2009; 69: 6932-40;

Hillier, S. M.; Maresca, K. P.; Lu, G.; Merkin, R. D.; Marquis, J. C.; Zimmerman, C. N.; Eckelman, W. C.; Joyal, J. L.; Babich, J. W., 99mTc-labeled small-molecule inhibitors of prostate-specific membrane antigen for molecular imaging of prostate cancer. *Journal of nuclear medicine: official publication, Society of Nuclear Medicine* 2013, 54 (8), 1369-76;

Jackson, P. F.; Cole, D. C.; Slusher, B. S.; Stetz, S. L.; Ross, L. E.; Donzanti, B. A.; Trainor, D. A., Design, synthesis, and biological activity of a potent inhibitor of the neuropeptidase N-acetylated alpha-linked acidic dipeptidase. *Journal of medicinal chemistry* 1996, 39 (2), 619-22;

Jackson, P. F.; Tays, K. L.; Maclin, K. M.; Ko, Y. S.; Li, W.; Vitharana, D.; Tsukamoto, T.; Stoermer, D.; Lu, X. C.; Wozniak, K.; Slusher, B. S., Design and pharmacological activity of phosphinic acid based NAALADase inhibitors. *Journal of medicinal chemistry* 2001, 44 (24), 4170-5;

Kabalka, G. W.; Mereddy, A. R., A facile no-carrier-added radioiodination procedure suitable for radiolabeling kits. *Nuclear medicine and biology* 2004, 31 (7), 935-8;

Kratochwil, C.; Giesel, F. L.; Eder, M.; Afshar-Oromieh, A.; Benesova, M.; Mier, W.;

Kopka, K.; Haberkorn, U., [Lu] Lutetium-labelled PSMA ligand-induced remission in a patient with metastatic prostate cancer. *European journal of nuclear medicine and molecular imaging* 2015;

Kularatne S A, Zhou Z, Yang J, Post C B, Low P S. Design, synthesis, and preclinical evaluation of prostate-specific membrane antigen (PSMA)-targeted-99mTc radioimaging agents. Molecular Pharmaceutics 2009; 6(3) 790-800;

Kurth M, Pelegrin A, Rose, K, Offord R E, Pochon S, Mach J-P, Buchegger F. Site-specific conjugation of a radioiodinated phenethylamine derivative to a monoclonal antibody results in increased radioactivity localization in tumor. J. Med. Chem. 1993; 36:1255-1261;

Kozikowski, A. P.; Nan, F.; Conti, P.; Zhang, J.; Ramadan, E.; Bzdega, T.; Wroblewska, B.; Neale, J. H.; Pshenichkin, S.; Wroblewski, J. T., Design of remarkably simple, yet potent urea-based inhibitors of glutamate carboxypeptidase II (NAALADase). *Journal of medicinal chemistry* 2001, 44 (3), 298-301;

Kozikowski, A. P.; Zhang, J.; Nan, F.; Petukhov, P. A.; Grajkowska, E.; Wroblewski, J. T.; Yamamoto, T.; Bzdega, T.; Wroblewska, B.; Neale, J. H., Synthesis of urea-based inhibitors as active site probes of glutamate carboxypeptidase II: efficacy as analgesic agents. *Journal of medicinal chemistry* 2004, 47 (7), 1729-38;

Lapi, S. E.; Wahnishe, H.; Pham, D.; Wu, L. Y.; Nedrow-Byers, J. R.; Liu, T.; Vejdani, K.; VanBrocklin, H. F.; Berkman, C. E.; Jones, E. F., Assessment of an 18F-labeled phosphoramidate peptidomimetic as a new prostate-specific membrane antigen-targeted imaging agent for prostate cancer. *Journal of nuclear medicine: official publication, Society of Nuclear Medicine* 2009, 50 (12), 2042-8;

Litosh, V. A. H., M. N.; Stupi, B. P.; Wu, W.; Metzker, M. L. Nucleotides and nucleosides and methods for their use in DNA sequencing. 2009;

Majer, P.; Jackson, P. F.; Delahanty, G.; Grella, B. S.; Ko, Y. S.; Li, W.; Liu, Q.; Maclin, K. M.; Polakova, J.; Shaffer, K. A.; Stoermer, D.; Vitharana, D.; Wang, E. Y.; Zakrzewski, A.; Rojas, C.; Slusher, B. S.; Wozniak, K. M.; Burak, E.; Limsakun, T.; Tsukamoto, T., Synthesis and biological evaluation of thiol-based inhibitors of glutamate carboxypeptidase II: discovery of an orally active GCP II inhibitor. *Journal of medicinal chemistry* 2003, 46 (10), 1989-96;

Makarasen, A., Nishikawa, T., Isobe, M., Synthesis of four lysine-linked cereulide analogues showing ionophoric activity towards potassium cations as lead compounds for emetic toxin detection by immunoassays. Synthesis 2009, 2184-2004;

Maresca, K. P.; Hillier, S. M.; Femia, F. J.; Keith, D.; Barone, C.; Joyal, J. L.; Zimmerman, C. N.; Kozikowski, A. P.; Barrett, J. A.; Eckelman, W. C.; Babich, J. W., A series of halogenated heterodimeric inhibitors of prostate specific membrane antigen (PSMA) as radiolabeled probes for targeting prostate cancer. Journal of medicinal chemistry 2009, 52 (2), 347-57;

Mease R C, Dusich C L, Foss C A, Ravert H T, Dannals R F, Seidel J, Prideaux A, Fox J J, Sgouros G, Kozikowski A P, Pomper M G. Synthesis and in vivo evaluation of N-[N-[(S)-1,3-dicarboxypropyl]carbamoyl]-4-[18F]fluorobenzyl-L-cysteine, [18F]DCFBC: anew imaging probe for prostate cancer. Clin Cancer Res 2008; 14:3036-3043;

Mease, R. C.; Foss, C. A.; Pomper, M. G., PET imaging in prostate cancer: focus on prostate-specific membrane antigen. Current topics in medicinal chemistry 2013, 13 (8), 951-62;

Mesters, J. R.; Barinka, C.; Li, W.; Tsukamoto, T.; Majer, P.; Slusher, B. S.; Konvalinka, J.; Hilgenfeld, R., Structure of glutamate carboxypeptidase II, a drug target in neuronal damage and prostate cancer. *Embo J* 2006, 25 (6), 1375-84;

Perner, S.; Hofer, M. D.; Kim, R.; Shah, R. B.; Li, H.; Moller, P.; Hautmann, R. E.;

Gschwend, J. E.; Kuefer, R.; Rubin, M. A., Prostate-specific membrane antigen expression as a predictor of prostate cancer progression. *Human pathology* 2007, 38 (5), 696-701;

Pinto, J. T.; Suffoletto, B. P.; Berzin, T. M.; Qiao, C. H.; Lin, S.; Tong, W. P.; May, F.; Mukherjee, B.; Heston, W. D., Prostate-specific membrane antigen: a novel folate hydrolase in human prostatic carcinoma cells. *Clin Cancer Res* 1996, 2 (9), 1445-51;

Maung, J.; Mallari, J. P.; Girtsman, T. A.; Wu, L. Y.; Rowley, J. A.; Santiago, N. M.; Brunelle, A. N.; Berkman, C. E., Probing for a hydrophobic a binding register in prostate-specific membrane antigen with phenylalkylphosphonamidates. *Bioorganic & medicinal chemistry* 2004, 12 (18), 4969-79;

Pomper M G, Musachio J L, Zhang J, Zhou Y, Scheffel U, Hilton J, Maini A, Dannals R F, Wong D F, Kozikowski A P. 11C-MCG: Synthesis, uptake selectivity and primate PET of a probe for glutamate carboxypeptidase II (NAALADase.) Mol Imaging 2002; 1:96-101;

Rajasekaran, A. K.; Anilkumar, G.; Christiansen, J. J., Is prostate-specific membrane antigen a multifunctional protein? *American journal of physiology. Cell physiology* 2005, 288 (5), C975-81;

Ray Banerjee, S.; Pullambhatla, M.; Foss, C. A.; Falk, A.; Byun, Y.; Nimmagadda, S.; Mease, R. C.; Pomper, M. G., Effect of chelators on the pharmacokinetics of (99m)Tc-labeled imaging agents for the prostate-specific membrane antigen (PSMA). *Journal of medicinal chemistry* 2013, 56 (15), 6108-21;

Reske, S. N.; Winter, G.; Baur, B.; Machulla, H. J.; Kull, T., Comment on Afshar-Oromieh et al.: PET imaging with a [68Ga]gallium-labelled PSMA ligand for the diagnosis of prostate cancer: biodistribution in humans and first evaluation of tumour lesions. *European journal of nuclear medicine and molecular imaging* 2013, 40 (6), 969-70;

Rowe, S. P. G., K. L.; Macura, K.; Guner, G.; Faraj, S. F.; Munari, E.; Rodriquez, R.; Han, M.; Blackford, A.; Netto, G.; Lodge, M.; Mease, R. C.; Pomper, M. G., Cho, S. Y., PSMA-based low molecular weight $^{18}$F-DCFBC PET/C T for detection and characterization of primary prostate cancer. *J. Nucl. Med.* 2015, In Press;

Rowe S P, Gorin M A, Hammers H J, Javadi M S, Hawasli H, Szabo Z, Cho S Y, Pomper M G, Allaf M E. Imaging of metastatic clear cell renal cell carcinoma with PSMA-target $^{18}$F-DCFPyL PET/C T;

Silver, D. A.; Pellicer, I.; Fair, W. R.; Heston, W. D.; Cordon-Cardo, C., Prostate-specific membrane antigen expression in normal and malignant human tissues. *Clin Cancer Res* 1997, 3 (1), 81-5;

Slusher, B. S.; Tsai, G.; Yoo, G.; Coyle, J. T., Immunocytochemical localization of the N-acetyl-aspartyl-glutamate (NAAG) hydrolyzing enzyme N-acetylated alpha-linked acidic dipeptidase (NAALADase). *The Journal of comparative neurology* 1992, 315 (2), 217-29;

Stoermer, D.; Vitharana, D.; Hin, N.; Delahanty, G.; Duvall, B.; Ferraris, D. V.; Grella, B. S.; Hoover, R.; Rojas, C.; Shanholtz, M. K.; Smith, K. P.; Stathis, M.; Wu, Y.; Wozniak, K. M.; Slusher, B. S.; Tsukamoto, T., Design, synthesis, and pharmacological evaluation of glutamate carboxypeptidase II (GCPII) inhibitors based on thioalkylbenzoic acid scaffolds. *Journal of medicinal chemistry* 2012, 55 (12), 5922-32;

Stoermer, D.; Liu, Q.; Hall, M. R.; Flanary, J. M.; Thomas, A. G.; Rojas, C.; Slusher, B. S.; Tsukamoto, T., Synthesis and biological evaluation of hydroxamate-Based inhibitors of glutamate carboxypeptidase II. *Bioorganic & medicinal chemistry letters* 2003, 13 (13), 2097-100;

Szabo, Z.; Mena, E.; Rowe, S. P.; Plyku, D.; Nidal, R.; Eisenberger, M. A.; Antonarakis, E. S.; Fan, H.; Dannals, R. F.; Chen, Y.; Mease, R. C.; Vranesic, M.; Bhatnagar, A.; Sgouros, G.; Cho, S. Y.; Pomper, M. G., Initial Evaluation of [F]DCFPyL for Prostate-Specific Membrane Antigen (PSMA)-Targeted PET Imaging of Prostate Cancer. *Molecular imaging and biology: MIB: the official publication of the Academy of Molecular Imaging* 2015;

Tsukamoto, T.; Wozniak, K. M.; Slusher, B. S., Progress in the discovery and development of glutamate carboxypeptidase II inhibitors. *Drug discovery today* 2007, 12 (17-18), 767-76

Tang, G., Zeng, W., Yu, M., Kabalka, G. Facile synthesis of N-succinimidyl-4-['F]fluorobenzoate ([18F]SFB for protein labeling. J Label Comp Radiopharm, 2008, 51, 68-71;

Talanov, V S, Garmestani K, Regino CAS, Milenic D E, Plascjak P S, Waldmann T A, Brechbiel M W. Preparation and in vivo evaluation of a novel stabilized linker for 211At labeling of protein. Nucl. Med. Biol. 2006; 33:469-480;

Vaidyanathan G, Zalutsky M R. Synthesis of N-succinimidyl 4-guanidinomethyl-3-[*I]iodobenzoate: a radio-iodination agent for labeling internalizing proteins and peptides. Nat Protoc 2007; 2:282-286;

Vallabhajosula, S.; Nikolopoulou, A.; Babich, J. W.; Osborne, J. R.; Tagawa, S. T.; Lipai, I.; Solnes, L.; Maresca, K. P.; Armor, T.; Joyal, J. L.; Crummet, R.; Stubbs, J. B.; Goldsmith, S. J., 99mTc-labeled small-molecule inhibitors of prostate-specific membrane antigen: pharmacokinetics and biodistribution studies in healthy subjects and patients with metastatic prostate cancer. *Journal of nuclear medicine: official publication, Society of Nuclear Medicine* 2014, 55 (11), 1791-8;

Vargas, H. A.; Grimm, J.; O, F. D.; Sala, E.; Hricak, H., Molecular imaging of prostate cancer: translating molecular biology approaches into the clinical realm. *European radiology* 2015

Wang, H.; Byun, Y.; Barinka, C.; Pullambhatla, M.; Bhang, H. E.; Fox, J. J.; Lubkowski, J.; Mease, R. C.; Pomper, M. G., Bioisosterism of urea-based GCPII inhibitors: Synthesis and structure-activity relationship studies. *Bioorganic & medicinal chemistry letters* 2010, 20 (1), 392-7;

Wang, E. K., H. C.; Szardenings, A. K., Liu, C.; Walsh, J. C.; Chen, G.; Sinha, A.; Kasi, D.; Gangadharmath, U. B.; Yu, C.; Zhang, W.; Zhao, T.; Mocharla, V. P. PSMA Imaging Agents. 28 Feb. 2013, 2013;

Weineisen, M. S., J.; Schottelius, M.; Schwaiger, M.; Wester, H-J., Synthesis and preclinical evaluation of DOTAGA-conjugated PSMA ligands for functional imaging and endoradiotherapy of prostate cancer. *EJNMMI*2014, 4 (63);

Winkler, J. W.; Uddin, J.; Serhan, C. N.; Petasis, N. A., Stereocontrolled total synthesis of the potent anti-inflammatory and pro-resolving lipid mediator resolvin D3 and its aspirin-triggered 17R-epimer. Organic letters 2013, 15 (7), 1424-7;

Zalutsky, M. R.; Narula, A. S., A method for the radiohalogenation of proteins resulting in decreased thyroid uptake of radioiodine. *Int J Rad Appl Instrum Part A* 1987, 38 (1051-1055);

Zechmann, C. M.; Afshar-Oromieh, A.; Armor, T.; Stubbs, J. B.; Mier, W.; Hadaschik, B.; Joyal, J.; Kopka, K.; Debus, J.; Babich, J. W.; Haberkorn, U., Radiation dosimetry and first therapy results with a (124)I/(131)I-labeled small molecule (MIP-1095) targeting PSMA for prostate cancer therapy. *European journal of nuclear medicine and molecular imaging* 2014, 41 (7), 1280-92;

Zhong, C.; Zhao, X.; Sarva, J.; Kozikowski, A.; Neale, J. H.; Lyeth, B. G., NAAG peptidase inhibitor reduces acute neuronal degeneration and astrocyte damage following lateral fluid percussion TBI in rats. J Neurotrauma 2005, 22 (2), 266-76;

Zhou J, Neale J H, Pomper M G, Kozikowski A P. NAAG Peptidase inhibitors and their potential for diagnosis and therapy. Nat Rev Drug Discovery 2005; 4:1015-1026.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (Ia'):

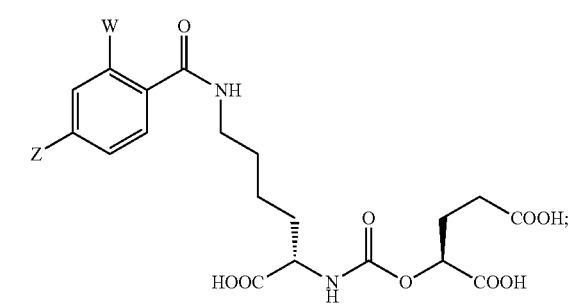

(Ia')

wherein:
W is selected from H and F; and
Z is selected from Br, F, I, $^{125}$I and $^{18}$F.

2. The compound of claim 1, wherein Z is selected from Br, I, and F.

3. The compound of claim 1, wherein Z is selected from $^{18}F$ and $^{125}I$.
4. The compound of claim 1, wherein the compound of formula (Ia') is selected from:
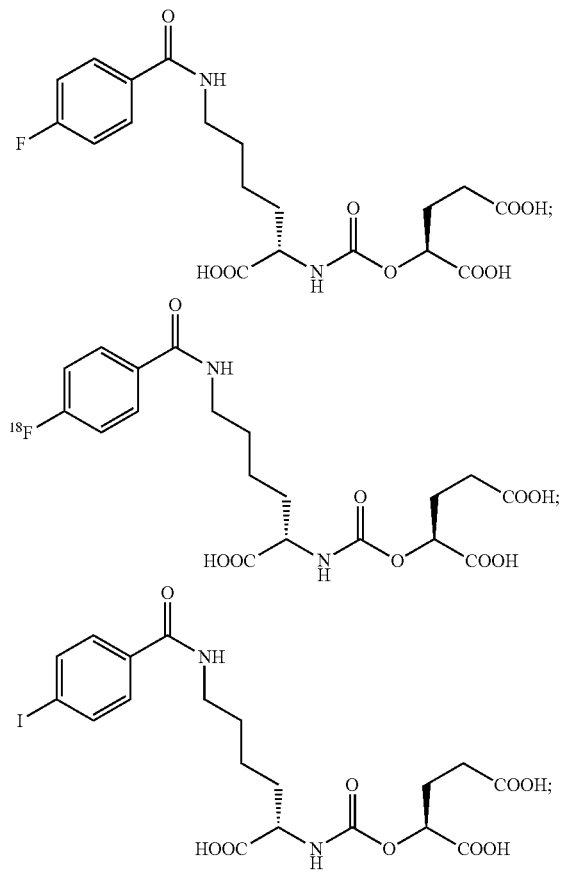
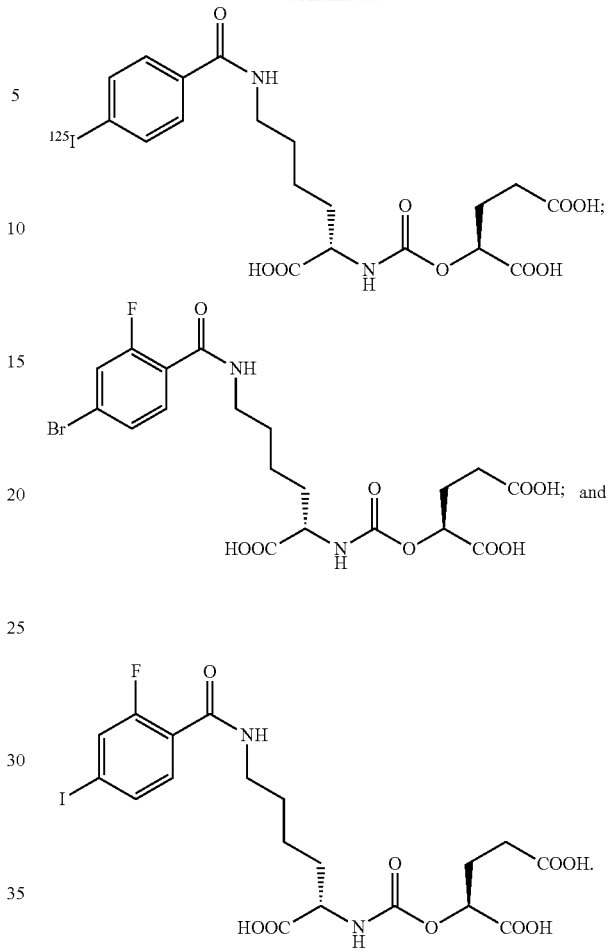
* * * * *